(12) United States Patent  (10) Patent No.: US 8,603,726 B2
Nakahara et al.  (45) Date of Patent: Dec. 10, 2013

(54) RADIATION-SENSITIVE RESIN COMPOSITION, POLYMER AND COMPOUND

(75) Inventors: Kazuo Nakahara, Tokyo (JP); Mitsuo Sato, Tokyo (JP); Yusuke Asano, Tokyo (JP)

(73) Assignee: JSR Corporation, Tokyo (JP)

( * ) Notice: Subject to any disclaimer, the term of this patent is extended or adjusted under 35 U.S.C. 154(b) by 81 days.

(21) Appl. No.: 13/243,046

(22) Filed: Sep. 23, 2011

(65) Prior Publication Data

US 2012/0082934 A1 Apr. 5, 2012

(30) Foreign Application Priority Data

Sep. 29, 2010 (JP) ................. 2010-219857

(51) Int. Cl.
  *G03F 7/00* (2006.01)
  *G03F 7/004* (2006.01)
  *G03F 7/028* (2006.01)
(52) U.S. Cl.
  USPC ....................... 430/270.1; 430/913
(58) Field of Classification Search
  USPC ....................... 430/270.1
  See application file for complete search history.

(56) References Cited

U.S. PATENT DOCUMENTS

| 8,088,553 B2* | 1/2012 | Shimizu et al. | 430/270.1 |
| 8,221,956 B2* | 7/2012 | Shiono et al. | 430/270.1 |
| 2009/0186300 A1* | 7/2009 | Furuya et al. | 430/285.1 |
| 2009/0197204 A1* | 8/2009 | Shiono et al. | 430/286.1 |
| 2012/0094236 A1* | 4/2012 | Shiono et al. | 430/285.1 |

FOREIGN PATENT DOCUMENTS

| JE | 2008-088343 | 4/2008 |
| JP | 05-188598 | 7/1993 |
| JP | 06-012452 | 2/1994 |
| JP | 2005-352384 | 12/2005 |
| JP | 2007-204385 | 8/2007 |
| JP | 2007-304537 | 11/2007 |
| JP | 2008-111103 | 5/2008 |
| JP | 2008111103 A * | 5/2008 |
| JP | 2009-019199 | 1/2009 |
| JP | 2009-074085 | 4/2009 |
| JP | 2009-134088 | 6/2009 |
| JP | 2010-032994 | 2/2010 |
| JP | 2010-066503 | 3/2010 |
| JP | 2010197413 A * | 9/2010 |
| WO | WO 2006/035790 | 4/2006 |
| WO | WO 2007/116664 | 10/2007 |
| WO | WO 2009/041270 | 4/2009 |
| WO | WO 2009/051088 | 4/2009 |

OTHER PUBLICATIONS

Nishikubo et al., "Convenient Syntheses of Cyclic Carbonates by New Reaction of Oxiranes with β-Butyrolactone", Tetrahedron Letters, 1986, pp. 3741-3744, vol. 27, No. 32.
Vincenzo Calò et al., "Cyclic Carbonate Formation from Carbon Dioxide and Oxiranes in Tetrabutylammonium Halides as Solvents and Catalysts", Organic Letters, 2002, pp. 2561-2563, vol. 4, No. 15.

* cited by examiner

*Primary Examiner* — Amanda C. Walke
(74) *Attorney, Agent, or Firm* — Ditthavong Mori & Steiner, P.C.

(57) ABSTRACT

A radiation-sensitive resin composition including (A) a polymer that includes a repeating unit (a1) and a fluorine atom, and (B) a photoacid generator, the repeating unit (a1) including a group shown by any of the following formulas (1-1) to (1-3).

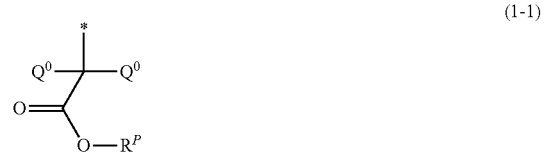

(1-1)

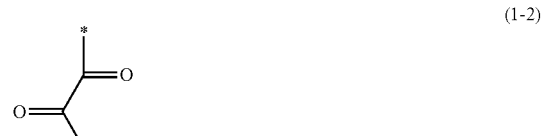

(1-2)

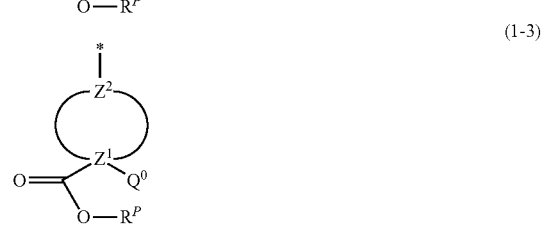

(1-3)

11 Claims, No Drawings

RADIATION-SENSITIVE RESIN COMPOSITION, POLYMER AND COMPOUND

CROSS-REFERENCE TO RELATED APPLICATIONS

The present application claims priority under 35 U.S.C. §119 to Japanese Patent Application No. 2010-219857, filed Sep. 29, 2010. The contents of this application are incorporated herein by reference in their entirety.

TECHNICAL FIELD

The invention relates to a radiation-sensitive resin composition, a polymer, and a compound.

BACKGROUND ART

In the field of microfabrication such as production of integrated circuit devices, a fine resist pattern may be formed by forming a resist film on a substrate using a resin composition that includes a polymer that contains an acid-labile group that dissociates due to an acid, exposing the resist film by applying short-wavelength radiation (e.g., excimer laser light) to the resist film via a mask pattern, and removing the exposed area using an alkaline developer. This process may utilize a chemically-amplified resist that includes a photoacid generator that generates an acid upon irradiation (exposure), and exhibits improved sensitivity due to the acid.

In recent years, liquid immersion lithography that exposes a resist film in a state in which an immersion liquid (e.g., purified water or fluorine-containing inert liquid) is provided between the lens and the resist film has become widespread as a method that can form a fine resist pattern having a line width of about 60 nm or less. The numerical aperture (NA) of the lens can be increased when using liquid immersion lithography. Moreover, the depth of focus decreases to only a small extent, and high resolution can be obtained even when increasing the NA of the lens.

It is preferable that the resist film used for liquid immersion lithography exhibit high surface hydrophobicity during liquid immersion lithography from the viewpoint of improving the scan speed resistance, and suppressing elution of the resist film composition into the immersion liquid, occurrence of defects due to droplets that remain on the surface of the film, and the like. In recent years, a method that improves the hydrophobicity of the surface of the resist film has been studied, and a resin composition that contains a fluorine-containing polymer that exhibits high hydrophobicity has been proposed (see Japanese Patent Application Publication (KOKAI) No. 2010-32994 and WO2007/116664, for example).

Japanese Patent Application Publication (KOKAI) No. 2010-32994 discloses a resin composition that includes a fluorine-containing polymer that includes a fluoroalkyl group as an alkali-labile group that dissociates under alkaline conditions. The fluoroalkyl group dissociates during alkali development via a reaction with the developer to produce a carboxylic acid, so that the surface of the resist film exhibits hydrophilicity. WO2007/116664 discloses a resin composition that includes a fluorine-containing polymer that contains an acid-labile group. The acid-labile group dissociates upon exposure to produce a polar group, so that the fluorine-containing polymer present in the exposed area exhibits improved solubility in the developer.

According to the invention, a radiation-sensitive resin composition includes (A) a polymer that includes a repeating unit (a1) and a fluorine atom, and (B) a photoacid generator, the repeating unit (a1) including a group shown by any of formulas (1-1) to (1-3),

[Chemical Formula 1]

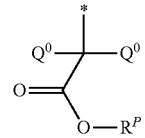

(1-1)

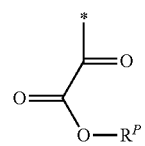

(1-2)

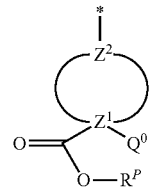

(1-3)

wherein $R^P$ represents a monovalent organic group, $Z^1$ represents a carbon atom, $Z^2$ represents a trivalent group that forms a cyclic hydrocarbon group together with $Z^1$, $Q^0$ in the formula (1-1) individually represent a hydrogen atom or a monovalent group, provided that at least one of $Q^0$ represents a monovalent organic group that includes an electron-withdrawing group, $Q^0$ in the formula (1-3) represents a monovalent organic group that includes an electron-withdrawing group, provided that a case where all of $Q^0$ in the formula (1-1) represent a fluorine atom or a fluorine-substituted hydrocarbon group is excluded, and "*" indicates a bonding hand.

The composition makes it possible to form a resist film that can suppress occurrence of development defects as much as possible.

According to the invention, a polymer includes a fluorine atom and at least one repeating unit among repeating units shown by the following formulas (P-1) to (P-3).

[Chemical Formula 5]

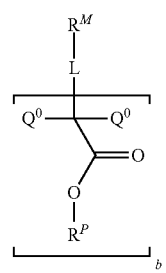

(P-1)

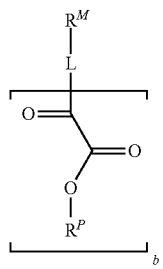

(P-2)

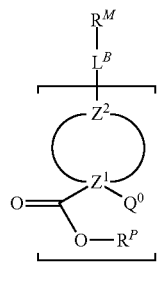

(P-3)

wherein L represents a (b+1)-valent linking group, $L^B$ represents a single bond or a (b+1)-valent linking group, $R^P$ represents a monovalent organic group, $Z^1$ represents a carbon atom, $Z^2$ represents a trivalent group that forms a cyclic hydrocarbon group together with $Z^1$, $Q^0$ in the formula (P-1) individually represent a hydrogen atom or a monovalent group, provided that at least one of $Q^0$ represents a monovalent organic group that includes an electron-withdrawing group, $Q^0$ in the formula (P-3) represents a monovalent organic group that includes an electron-withdrawing group, provided that a case where all of $Q^0$ in the formula (P-1) represent a fluorine atom or a fluorine-substituted hydrocarbon group is excluded, and b in the formulas (P-1) and (P-2) is an integer from 1 to 5, provided that a plurality of $R^P$ and a plurality of $Q^0$ may respectively be either the same or different when b is an integer from 2 to 5, b in the formula (P-3) is 1 when $L^B$ represents a single bond, and is an integer from 1 to 5 when $L^B$ does not represent a single bond, provided that a plurality of $R^P$, a plurality of $Z^2$, and a plurality of $Q^0$ may respectively be either the same or different when b is an integer from 2 to 5.

$R^M$ represents any of groups shown by the following formulas.

[Chemical Formula 6]

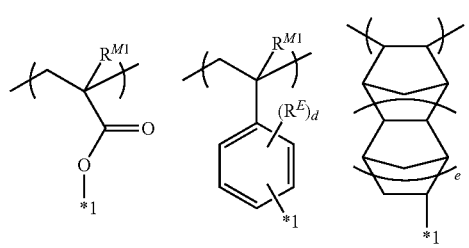

wherein $R^{M1}$ represents a hydrogen atom, a fluorine atom, an alkyl group having 1 to 5 carbon atoms, or a fluoroalkyl group having 1 to 5 carbon atoms, $R^E$ represents a substituent, d is an integer from 0 to 4, provided that a plurality of $R^E$ may be either the same or different when d is an integer from 2 to 4, e is 0 or 1, and "*1" indicates a bonding hand bonded to L or $L^B$.

According to the invention, a compound includes a fluorine atom and is shown by any of the following formulas (M-1) to (M-3).

[Chemical Formula 7]

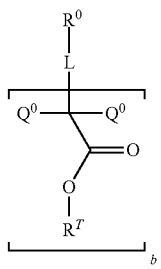

(M-1)

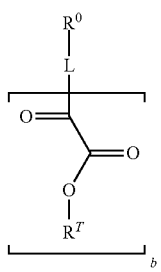

(M-2)

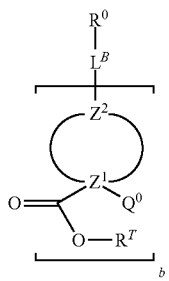

(M-3)

wherein L represents a (b+1)-valent linking group, $L^B$ represents a single bond or a (b+1)-valent linking group, $R^T$ represents a hydrogen atom or a monovalent organic group, $Z^1$ represents a carbon atom, $Z^2$ represents a trivalent group that forms a cyclic hydrocarbon group together with $Z^1$, $Q^0$ in the formula (M-1) individually represent a hydrogen atom or a monovalent group, provided that at least one of $Q^0$ represents a monovalent organic group that includes an electron-withdrawing group, $Q^0$ in the formula (M-3) represents a monovalent organic group that includes an electron-withdrawing group, provided that a case where all of $Q^0$ in the formula (M-1) represent a fluorine atom or a fluorine-substituted hydrocarbon group is excluded, b in the formulas (M-1) and (M-2) is an integer from 1 to 5, provided that a plurality of $R^T$ and a plurality of $Q^0$ may respectively be either the same or different when b is an integer from 2 to 5, b in the formula (M-3) is 1 when $L^B$ represents a single bond, and is an integer from 1 to 5 when $L^B$ does not represent a single bond, provided that a plurality of $R^T$, a plurality of $Z^2$, and a plurality of $Q^0$ may respectively be either the same or different when b is an integer from 2 to 5.

$R^0$ represents any of groups shown by the following formulas.

[Chemical Formula 8]

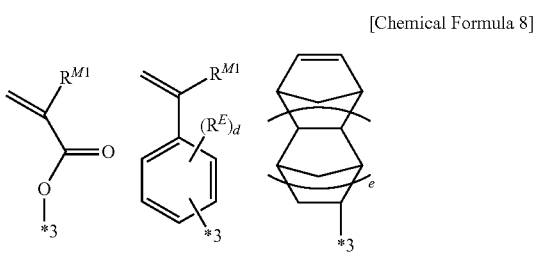

wherein $R^{M1}$ represents a hydrogen atom, a fluorine atom, an alkyl group having 1 to 5 carbon atoms, or a fluoroalkyl group having 1 to 5 carbon atoms, $R^E$ represents a substituent, d is an integer from 0 to 4, provided that a plurality of $R^E$ may be either the same or different when d is an integer from 2 to 4, e is 0 or 1, and "*3" indicates a bonding hand bonded to L or $L^B$.

DESCRIPTION OF THE EMBODIMENTS

According to the invention, a radiation-sensitive resin composition includes (A) a polymer that includes a repeating unit (a1) and a fluorine atom, and (B) a photoacid generator, the repeating unit (a1) including a group shown by any of formulas (1-1) to (1-3),

[Chemical Formula 1]

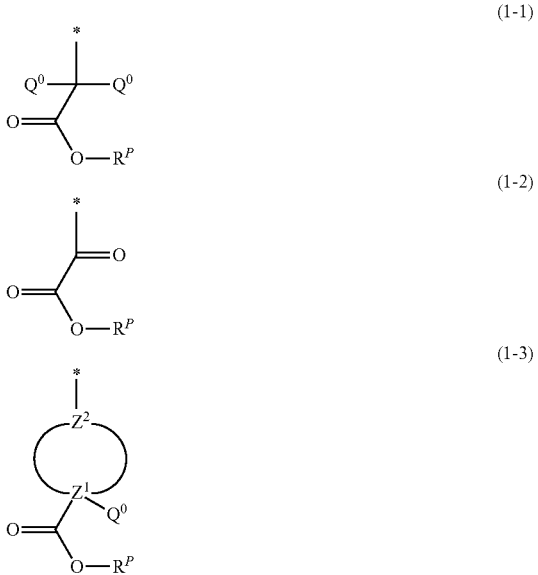

wherein $R^P$ represents a monovalent organic group, $Z^1$ represents a carbon atom, $Z^2$ represents a trivalent group that forms a cyclic hydrocarbon group together with $Z^1$, $Q^0$ in the formula (1-1) individually represent a hydrogen atom or a monovalent group, provided that at least one of $Q^0$ represents a monovalent organic group that includes an electron-withdrawing group, $Q^0$ in the formula (1-3) represents a monovalent organic group that includes an electron-withdrawing group, provided that a case where all of $Q^0$ in the formula (1-1) represent a fluorine atom or a fluorine-substituted hydrocarbon group is excluded, and "*" indicates a bonding hand.

In the polymer (A), a unit that includes an electron-withdrawing group is bonded to the carbon atom (e.g., $Z^1$ in the formula (1-3)) at the α-position with respect to the ester group. Therefore, the ester group included in the polymer (A) exhibits high reactivity, so that the monovalent organic group —$R^P$ dissociates promptly in the presence of an acid or under alkaline conditions, so that a carboxylic acid is produced. When forming a resist film using the composition that includes the polymer (A), the surface of the resist film exhibits hydrophobicity due to the fluorine atom included in the polymer (A), and a carboxylic acid is promptly produced in the presence of an acid or under alkaline conditions. When the monovalent organic group —$R^P$ is an acid-labile group, the resist film exhibits excellent solubility in a developer after exposure, and the exposed area rarely remains undeveloped. As a result, defects such as bridge defects can be advantageously suppressed. When the monovalent organic group —$R^P$ is an alkali-labile group, impurities (e.g., development residue) rarely adhere to the surface of the film during alkali development. Moreover, since the alkaline developer is promptly spread over the surface of the resist film when the alkaline developer has come in contact with the surface of the resist film, the resist film can be advantageously developed. Therefore, the composition makes it possible to form a resist film that can suppress occurrence of development defects as much as possible.

The monovalent organic group that includes an electron-withdrawing group represented by $Q^0$ may be a group shown by the following formula ($Q^0$-1).

[Chemical Formula 2]

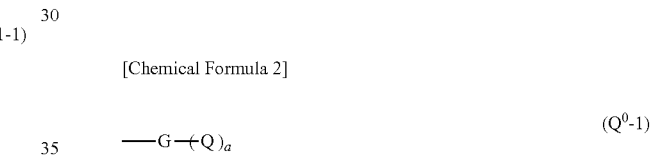

wherein Q represents a monovalent electron-withdrawing group, G represents a single bond or an (a+1)-valent linking group, and a is 1 when G represents a single bond, and is an integer from 1 to 4 when G does not represent a single bond, provided that a plurality of Q that are bonded to G may be either the same or different when a is an integer from 2 to 4.

The polymer (A) preferably includes at least one repeating unit among repeating units shown by the following formulas (1p) to (3p) as the repeating unit (a1).

[Chemical Formula 3]

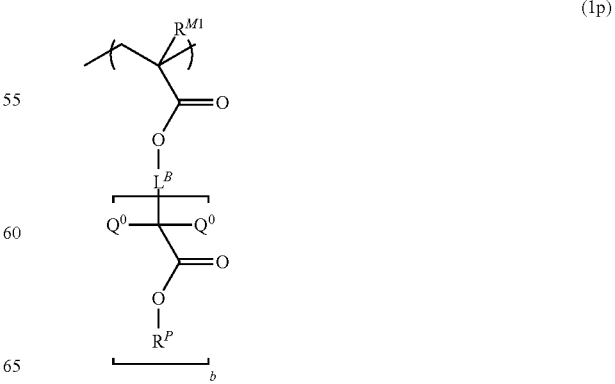

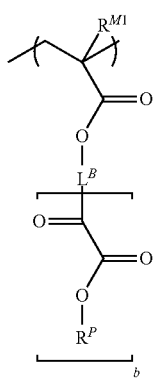

(2p)

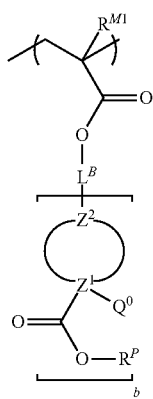

(3p)

wherein $R^{M1}$ represents a hydrogen atom, a fluorine atom, an alkyl group having 1 to 5 carbon atoms, or a fluoroalkyl group having 1 to 5 carbon atoms, $L^B$ represents a single bond or a (b+1)-valent linking group, $R^P$ represents a monovalent organic group, $Z^1$ represents a carbon atom, $Z^2$ represents a trivalent group that forms a cyclic hydrocarbon group together with $Z^1$, $Q^0$ in the formula (1p) individually represent a hydrogen atom or a monovalent group, provided that at least one of $Q^0$ represents a monovalent organic group that includes an electron-withdrawing group, $Q^0$ in the formula (3p) represents a monovalent organic group that includes an electron-withdrawing group, provided that a case where all of $Q^0$ in the formula (1p) represent a fluorine atom or a fluorine-substituted hydrocarbon group is excluded, and b is 1 when $L^B$ represents a single bond, and is an integer from 1 to 5 when $L^B$ does not represent a single bond, provided that a plurality of $R^P$, a plurality of $Z^2$, and a plurality of $Q^0$ may respectively be either the same or different when b is an integer from 2 to 5.

In this case, light absorption can be reduced when using ArF excimer laser light in an exposure step of a resist pattern-forming method. Moreover, production can be facilitated. When $L^B$ represents a (b+1)-valent linking group, $R^P$ is isolated from the main chain of the polymer (A) due to the (b+1)-valent linking group. Therefore, reactivity when $R^P$ dissociates can be improved.

The repeating unit (a1) preferably includes at least one electron-withdrawing group (excluding a fluorine atom and a fluorine-substituted hydrocarbon group) as $Q^0$, the at least one electron-withdrawing group being bonded directly to a carbon atom at an α-position with respect to an ester group. When an electron-withdrawing group is bonded directly to the carbon atom at the α-position, the reactivity of the ester group can be further improved.

The polymer (A) preferably includes at least one repeating unit among repeating units shown by the following formulas (1p-1) to (1p-3) and (2p) as the repeating unit (a1).

[Chemical Formula 4]

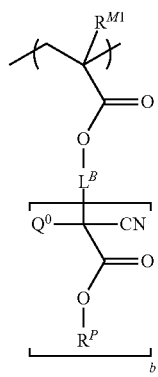

(1p-1)

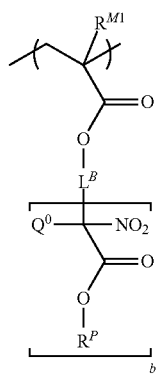

(1p-2)

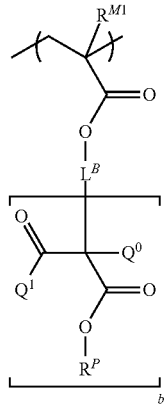

(1p-3)

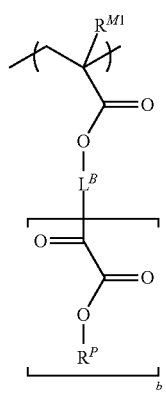

(2p)

wherein $R^{M1}$ represents a hydrogen atom, a fluorine atom, an alkyl group having 1 to 5 carbon atoms, or a fluoroalkyl group having 1 to 5 carbon atoms, $L^B$ represents a single bond or a (b+1)-valent linking group, $R^P$ represents a monovalent organic group, $Q^0$ represents a hydrogen atom or a monovalent group, $Q^1$ represents a hydrogen atom or a monovalent hydrocarbon group, and b is 1 when $L^B$ represents a single bond, and is an integer from 1 to 5 when $L^B$ does not represent a single bond, provided that a plurality of $R^P$, a plurality of $Q^0$, and a plurality of $Q^1$ may respectively be either the same or different when b is an integer from 2 to 5.

In this case, the reactivity of the ester group can be advantageously improved.

It is preferable that $R^P$ represent a monovalent hydrocarbon group that includes a fluorine atom so that a decrease in hydrophobicity upon dissociation of $R^P$ increases. In particular, when $R^P$ represents an alkali-labile group, a decrease in hydrophobicity upon dissociation of $R^P$ can be increased while improving reactivity when $R^P$ dissociates when $R^P$ represent a monovalent hydrocarbon group that includes a fluorine atom.

It is preferable that $R^P$ represent a monovalent aromatic hydrocarbon group that may include a fluorine atom so that $R^P$ easily dissociates under alkaline conditions.

It is preferable that the radiation-sensitive resin composition further include (C) a polymer that has a fluorine atom content lower than that of the polymer (A), and the polymer (C) include an acid-labile group. In this case, the repeating unit (a1) and the fluorine atom are unevenly distributed in the surface layer of the resulting resist film. This ensures that the surface of the resist film exhibits hydrophobicity during liquid immersion lithography, and makes it possible to advantageously form a resist pattern. Moreover, since the group —$R^P$ dissociates promptly in the presence of an acid or under alkaline conditions so that a carboxylic acid is produced, development defects can be advantageously suppressed.

According to the invention, a polymer includes a fluorine atom and at least one repeating unit among repeating units shown by the following formulas (P-1) to (P-3).

[Chemical Formula 5]

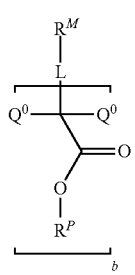

(P-1)

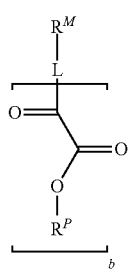

(P-2)

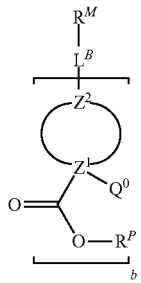

(P-3)

wherein L represents a (b+1)-valent linking group, $L^B$ represents a single bond or a (b+1)-valent linking group, $R^P$ represents a monovalent organic group, $Z^1$ represents a carbon atom, $Z^2$ represents a trivalent group that forms a cyclic hydrocarbon group together with $Z^1$, $Q^0$ in the formula (P-1) individually represent a hydrogen atom or a monovalent group, provided that at least one of $Q^0$ represents a monovalent organic group that includes an electron-withdrawing group, $Q^0$ in the formula (P-3) represents a monovalent organic group that includes an electron-withdrawing group, provided that a case where all of $Q^0$ in the formula (P-1) represent a fluorine atom or a fluorine-substituted hydrocarbon group is excluded, and b in the formulas (P-1) and (P-2) is an integer from 1 to 5, provided that a plurality of $R^P$ and a plurality of $Q^0$ may respectively be either the same or different when b is an integer from 2 to 5, b in the formula (P-3) is 1 when $L^B$ represents a single bond, and is an integer from 1 to 5 when $L^B$ does not represent a single bond, provided that a plurality of $R^P$, a plurality of $Z^2$, and a plurality of $Q^0$ may respectively be either the same or different when b is an integer from 2 to 5.

$R^M$ represents any of groups shown by the following formulas.

[Chemical Formula 6]

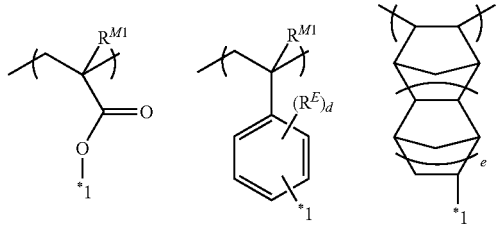

wherein $R^{M1}$ represents a hydrogen atom, a fluorine atom, an alkyl group having 1 to 5 carbon atoms, or a fluoroalkyl group having 1 to 5 carbon atoms, $R^E$ represents a substituent, d is an integer from 0 to 4, provided that a plurality of $R^E$ may be either the same or different when d is an integer from 2 to 4, e is 0 or 1, and "*1" indicates a bonding hand bonded to L or $L^B$.

According to the invention, a compound includes a fluorine atom and is shown by any of the following formulas (M-1) to (M-3).

[Chemical Formula 7]

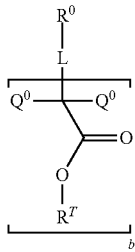
(M-1)

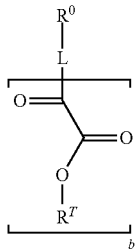
(M-2)

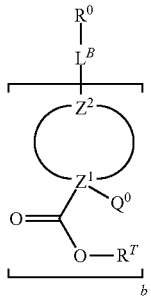
(M-3)

wherein L represents a (b+1)-valent linking group, $L^B$ represents a single bond or a (b+1)-valent linking group, $R^T$ represents a hydrogen atom or a monovalent organic group, $Z^1$ represents a carbon atom, $Z^2$ represents a trivalent group that forms a cyclic hydrocarbon group together with $Z^1$, $Q^0$ in the formula (M-1) individually represent a hydrogen atom or a monovalent group, provided that at least one of $Q^0$ represents a monovalent organic group that includes an electron-withdrawing group, $Q^0$ in the formula (M-3) represents a monovalent organic group that includes an electron-withdrawing group, provided that a case where all of $Q^0$ in the formula (M-1) represent a fluorine atom or a fluorine-substituted hydrocarbon group is excluded, b in the formulas (M-1) and (M-2) is an integer from 1 to 5, provided that a plurality of $R^T$ and a plurality of $Q^0$ may respectively be either the same or different when b is an integer from 2 to 5, b in the formula (M-3) is 1 when $L^B$ represents a single bond, and is an integer from 1 to 5 when $L^B$ does not represent a single bond, provided that a plurality of $R^T$, a plurality of $Z^2$, and a plurality of $Q^0$ may respectively be either the same or different when b is an integer from 2 to 5.

$R^0$ represents any of groups shown by the following formulas.

[Chemical Formula 8]

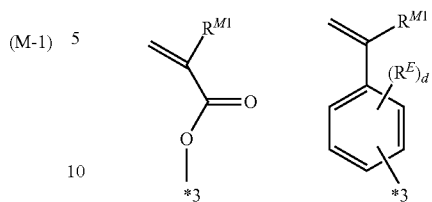

wherein $R^{M1}$ represents a hydrogen atom, a fluorine atom, an alkyl group having 1 to 5 carbon atoms, or a fluoroalkyl group having 1 to 5 carbon atoms, $R^E$ represents a substituent, d is an integer from 0 to 4, provided that a plurality of $R^E$ may be either the same or different when d is an integer from 2 to 4, e is 0 or 1, and "*3" indicates a bonding hand bonded to L or $L^B$.

The term "electron-withdrawing group" used herein refers to a substituent that draws electrons from the atom bonded thereto as compared with a hydrogen atom.

The term "acid-labile group" used herein refers to a group that substitutes a hydrogen atom of a polar functional group (e.g., hydroxyl group or carboxyl group), and dissociates in the presence of an acid.

The term "alkali-labile group" used herein refers to a group that substitutes a hydrogen atom of a polar functional group (e.g., hydroxyl group or carboxyl group), and dissociates under alkaline conditions (e.g., in a 2.38 mass % tetramethylammonium hydroxide aqueous solution (23° C.)).

The term "hydrocarbon group" used herein includes a chain-like hydrocarbon group, an alicyclic hydrocarbon group, and an aromatic hydrocarbon group. The hydrocarbon group may be a saturated hydrocarbon group or an unsaturated hydrocarbon group.

The term "chain-like hydrocarbon group" used herein refers to a hydrocarbon group that does not include a cyclic structure, but includes only a chain-like structure. The term "chain-like hydrocarbon group" used herein includes a linear hydrocarbon group and a branched hydrocarbon group.

The term "aliphatic hydrocarbon group" used herein refers to a hydrocarbon group that does not include an aromatic ring structure. The term "aliphatic hydrocarbon group" used herein includes a linear hydrocarbon group, a branched hydrocarbon group, and an alicyclic hydrocarbon group.

The term "alicyclic hydrocarbon group" used herein refers to a hydrocarbon group that includes only an alicyclic hydrocarbon structure as a cyclic structure, and does not include an aromatic ring structure. Note that the alicyclic hydrocarbon group need not necessarily include only an alicyclic hydrocarbon structure, but may also include a chain-like structure.

The term "aromatic hydrocarbon group" used herein refers to a hydrocarbon group that includes an aromatic ring structure. Note that the aromatic hydrocarbon group need not necessarily include only an aromatic ring structure, but may also include a chain structure or an alicyclic hydrocarbon structure.

A radiation-sensitive resin composition according to the invention includes (A) a polymer that includes a fluorine atom as a polymer component. The composition also includes (B) a photoacid generator. The composition also includes (C) a polymer that has a fluorine atom content lower than that of the polymer (A) as an additional polymer component, the polymer (C) changing in solubility in a developer due to an acid. The composition may include (D) an acid diffusion controller, (E) a solvent, (F) an additive, and the like as preferable optional components. Each component is described below.

<Polymer (A)>
<Repeating Unit (a1)>

The polymer (A) includes a repeating unit (a1) that includes a group shown by any of the following formulas (1-1) to (1-3).

[Chemical Formula 9]

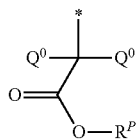

(1-1)

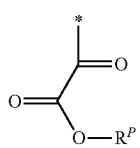

(1-2)

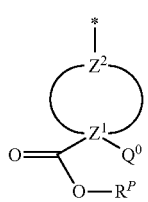

(1-3)

wherein $R^P$ represents a monovalent organic group, $Z^1$ represents a carbon atom, $Z^2$ represents a trivalent group that forms a cyclic hydrocarbon group together with $Z^1$, $Q^0$ in the formula (1-1) individually represent a hydrogen atom or a monovalent group, provided that at least one of $Q^0$ represents a monovalent organic group that includes an electron-withdrawing group, $Q^0$ in the formula (1-3) represents a monovalent organic group that includes an electron-withdrawing group, provided that a case where all of $Q^0$ in the formula (1-1) represent a fluorine atom or a fluorine-substituted hydrocarbon group is excluded, and "*" indicates a bonding hand.

Specific examples of the monovalent organic group that includes an electron-withdrawing group represented by $Q^0$ in the formulas (1-1) and (1-3) include a group shown by the following formula ($Q^0$-1).

[Chemical Formula 10]

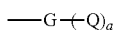

($Q^0$-1)

wherein Q represents a monovalent electron-withdrawing group, G represents a single bond or an (a+1)-valent linking group, and a is 1 when G represents a single bond, and is an integer from 1 to 4 when G does not represent a single bond, provided that a plurality of Q that are bonded to G may be either the same or different when a is an integer from 2 to 4.

When $Q^0$ in the formulas (1-1) and (1-3) represents the group shown by the formula ($Q^0$-1), at least one of the monovalent electron-withdrawing groups represented by Q is preferably a group other than a fluorine atom and a fluorine-substituted hydrocarbon group. Specific examples of the monovalent electron-withdrawing group represented by Q include —$CCl_3$, —$NO_2$, —CN, —CO-$Q^1$, —COO-$Q^1$, —$SO_2$-$Q^1$, —$^+N(Q^2)_3$, —$SO_3H$, Cl, Br, I, —$CH_2Cl$, —CH=$CHNO_2$, and the like.

When at least one of the monovalent electron-withdrawing groups is a group other than a fluorine atom and a fluorine-substituted hydrocarbon group, affinity to a developer after dissociation of $R^P$ can be improved as compared with the case where all of the electron-withdrawing groups are either a fluorine atom or a fluorine-substituted hydrocarbon group. When a plurality of Q (i.e., monovalent electron-withdrawing groups) are present, some of the plurality of monovalent electron-withdrawing groups may be a fluorine atom or a fluorine-substituted hydrocarbon group (e.g., —$CF(Q^1)_2$, —$CF_2$-$Q^1$, —$CF_3$, or F).

Note that $Q^1$ represents a hydrogen atom or a monovalent substituted or unsubstituted hydrocarbon group. The monovalent substituted or unsubstituted hydrocarbon group is preferably a chain-like hydrocarbon group having 1 to 6 carbon atoms that includes a fluorine atom, or an alicyclic hydrocarbon group having 3 to 10 carbon atoms that includes a fluorine atom. $Q^1$ preferably represents a hydrogen atom. $Q^2$ individually represent a hydrogen atom or a substituted or unsubstituted linear or branched alkyl group, provided that a plurality of $Q^2$ that represent a hydrocarbon group may form a ring together with the nitrogen atom bonded to the plurality of $Q^2$. $Q^2$ preferably represents a hydrogen atom.

The reactivity of the ester group can be improved due to the electron-withdrawing group. The electron-withdrawing group is preferably —$NO_2$, —CN, —CO-$Q^1$, or —COO-$Q^1$. Since these groups exhibit a high electron-withdrawing capability, the reactivity of the ester group can be improved. The electron-withdrawing group more preferably does not include a fluorine atom. In this case, a fluorine atom is not bonded to the carbon atom (e.g., $Z^1$ in the formula (1-3)) at the α-position with respect to the ester group (hereinafter may be referred to as "specific α-position carbon"). As a result, affinity to a developer after dissociation of $R^P$ can be further improved. This makes it possible to suppress development defects. Moreover, the resist pattern obtained by development has an excellent shape due to an increase in solubility in an alkaline developer. The electron-withdrawing group is preferably —$NO_2$ or —CN in order to improve the reactivity of the ester group, and is more preferably —CN in order to provide the ester group with moderate stability.

G in the formula ($Q^0$-1) represents a single bond or an (a+1)-valent linking group. Specific examples of the (a+1)-valent linking group represented by G include an (a+1)-valent chain-like hydrocarbon group, an (a+1)-valent alicyclic hydrocarbon group, and an (a+1)-valent aromatic ring group.

Examples of the (a+1)-valent chain-like hydrocarbon group represented by G include a group obtained by removing (a+1) hydrogen atoms from a linear or branched hydrocarbon having 1 to 30 carbon atoms. The number of carbon atoms of the linear or branched hydrocarbon is preferably 1 to 6, and more preferably 1 to 3.

Examples of the (a+1)-valent alicyclic hydrocarbon group represented by G include a group obtained by removing (a+1) hydrogen atoms from an alicyclic hydrocarbon having 3 to 30 carbon atoms. The number of carbon atoms of the alicyclic hydrocarbon is preferably 3 to 12. Specific examples of the (a+1)-valent alicyclic hydrocarbon group represented by G include a group obtained by removing (a+1) hydrogen atoms from a monocycloalkane or a polycycloalkane (e.g., bicycloalkane or tricycloalkane). The (a+1)-valent alicyclic hydrocarbon group represented by G is more preferably a group obtained by removing (a+1) hydrogen atoms from a cyclopentane group or a cyclohexane group. The (a+1)-valent alicyclic hydrocarbon group may be a group obtained by substituting an alicyclic hydrocarbon with a monovalent chain-like hydrocarbon group having 1 to 6 carbon atoms. The chain-like hydrocarbon group may be present between the specific α-position carbon and Q, and an aliphatic ring may branch from the chain-like hydrocarbon group.

Examples of the (a+1)-valent aromatic ring group represented by G include a group obtained by removing (a+1) hydrogen atoms from an aromatic hydrocarbon having 6 to 30 carbon atoms. The number of carbon atoms of the aromatic hydrocarbon is preferably 6 to 10. Specific examples of the (a+1)-valent aromatic ring group represented by G include a group obtained by removing (a+1) hydrogen atoms from a benzene ring or a naphthalene ring. The (a+1)-valent aromatic ring group may be a group obtained by substituting an aromatic hydrocarbon with a monovalent chain-like hydrocarbon group having 1 to 6 carbon atoms or a monovalent alicyclic hydrocarbon group having 3 to 10 carbon atoms. The chain-like hydrocarbon group or the alicyclic hydrocarbon group may be present between the specific α-position carbon and Q, and an aromatic ring may branch from the chain-like hydrocarbon group.

When the alicyclic hydrocarbon group is present between the specific α-position carbon and Q (electron-withdrawing group), the number of carbon atoms of the site of the alicyclic hydrocarbon group that is bonded to the specific α-position carbon and the electron-withdrawing group represented by Q is preferably 1 or 2 so that the electron-withdrawing group represented by Q exhibits the electron-withdrawing effect on the ester group.

Specific examples of the (a+1)-valent linking group represented by G that is bonded to the electron-withdrawing group represented by Q include the following groups.

[Chemical Formula 11]

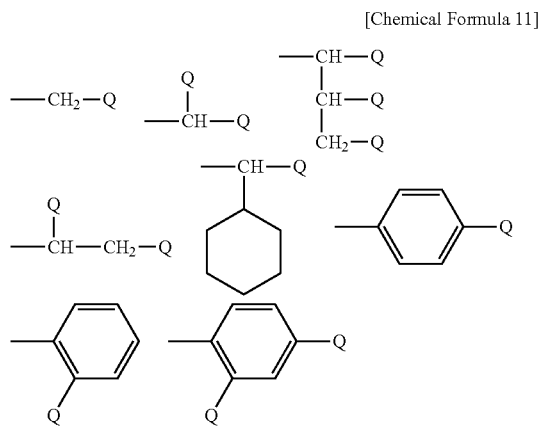

When G does not represent a single bond, a is preferably 1 or 2, and more preferably 1. G preferably represents a single bond so that the reactivity of the ester group is improved.

Examples of the monovalent group represented by $Q^0$ in the formula (1-1) that does not include an electron-withdrawing group include monovalent chain-like saturated hydrocarbon groups having 1 to 10 carbon atoms, monovalent alicyclic saturated hydrocarbon groups having 3 to 20 carbon atoms, monovalent aromatic hydrocarbon groups having 6 to 30 carbon atoms, and the like.

These monovalent hydrocarbon groups may be substituted with a substituent. Examples of the substituent include a hydroxyl group, a carboxyl group, and the like. The monovalent hydrocarbon groups may be substituted with one or more of one type of substituent, or may be substituted with one or more of each of a plurality of types of substituent. The monovalent group represented by $Q^0$ that does not include an electron-withdrawing group is preferably an alkyl group having 1 to 10 carbon atoms, more preferably an alkyl group having 1 to 6 carbon atoms, and still more preferably an alkyl group having 1 to 3 carbon atoms (e.g., methyl group, ethyl group, 1-propyl group, or 2-propyl group).

It is preferable that both $Q^0$ in the formula (1-1) represent a monovalent organic group that includes an electron-withdrawing group when it is desired to improve the reactivity. When it is desired to facilitate production while achieving moderate stability, it is preferable that one of $Q^0$ represent a monovalent organic group that includes an electron-withdrawing group, and the other of $Q^0$ represent a hydrogen atom or a monovalent group that does not include an electron-withdrawing group (more preferably a hydrogen atom).

The cyclic hydrocarbon group formed by $Z^1$ and $Z^2$ in the formula (1-3) may be an alicyclic hydrocarbon group or an aromatic hydrocarbon group. Specific examples of the cyclic hydrocarbon group formed by $Z^1$ and $Z^2$ include a group obtained by removing three hydrogen atoms from adamantane, norbornane, perhydroanthracene, perhydronaphthalene, tricyclo[5.2.1.0$^{2,6}$]decane, cyclopentane, cyclohexane, bicyclohexane, spiro[4,4]nonane, spiro[4,5]decane, or a derivative thereof. Among these, an alicyclic hydrocarbon group having 3 to 12 carbon atoms is preferable. More specifically, a group obtained by removing three hydrogen atoms from norbornane or a derivative thereof, or a group obtained by removing three hydrogen atoms from cyclohexane or a derivative thereof, are preferable.

Examples of the monovalent organic group represented by $R^P$ in the formulas (1-1) to (1-3) include an acid-labile group and an alkali-labile group. When $R^P$ represents an acid-labile group, an area exposed in an exposure step of a resist pattern-forming method described later exhibits improved solubility in an alkaline developer. When $R^P$ represents an alkali-labile group, the solubility in an alkaline developer can be improved, and the hydrophobicity of the surface of the resist film after development can be further reduced.

Specific examples of the acid-labile group represented by $R^P$ include a t-butoxycarbonyl group, a tetrahydropyranyl group, a tetrahydrofuranyl group, a (thiotetrahydropyranylsulfanyl)methyl group, a (thiotetrahydrofuranylsulfanyl)methyl group, an alkoxy-substituted methyl group, an alkylsulfanyl-substituted methyl group, and the like. Examples of the alkoxy group (substituent) of the alkoxy-substituted methyl group include alkoxy groups having 1 to 4 carbon atoms. Examples of the alkyl group (substituent) of the alkylsulfanyl-substituted methyl group include alkyl groups having 1 to 4 carbon atoms. A group shown by the following formula ($R^P$-1) is preferable as the acid-labile group represented by $R^P$.

[Chemical Formula 12]

wherein $R^{P1}$ represents an alkyl group having 1 to 4 carbon atoms or a monovalent alicyclic hydrocarbon group having 4 to 20 carbon atoms, and $R^{P2}$ and $R^{P3}$ individually represent an alkyl group having 1 to 4 carbon atoms or a monovalent alicyclic hydrocarbon group having 4 to 20 carbon atoms, or bond to each other to form a divalent alicyclic hydrocarbon group having 4 to 20 carbon atoms together with the carbon atom bonded to $R^{P2}$ and $R^{P3}$.

Examples of the alkyl group having 1 to 4 carbon atoms represented by $R^{P1}$ to $R^{P3}$ in the formula ($R^P$-1)) include a methyl group, an ethyl group, an n-propyl group, an i-propyl group, an n-butyl group, a 2-methylpropyl group, a 1-methylpropyl group, a t-butyl group, and the like.

Examples of the monovalent alicyclic hydrocarbon group having 4 to 20 carbon atoms represented by $R^{P1}$ to $R^{P3}$ or the divalent alicyclic hydrocarbon group having 4 to 20 carbon atoms formed by $R^{P2}$ and $R^{P3}$ together with the carbon atom bonded to $R^{P2}$ and $R^{P3}$ include groups having a bridged skeleton (e.g., adamantane skeleton or norbornane skeleton) or a cycloalkane skeleton (e.g., cyclopentane skeleton or cyclohexane skeleton), and groups obtained by substituting these groups with at least one linear or branched alkyl group having 1 to 10 carbon atoms (e.g., methyl group, ethyl group, n-propyl group, or i-propyl group) or alicyclic hydrocarbon group. Among these, a group having a cycloalkane skeleton is preferable since the shape of the resist pattern obtained by development can be further improved. Specific examples of the group shown by the formula ($R^P$-1) include groups shown by the following formulas ($R^P$-1-1) to ($R^P$-1-4).

[Chemical Formula 13]

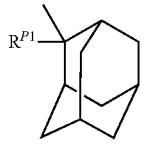

($R^P$-1-1)

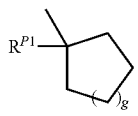

($R^P$-1-2)

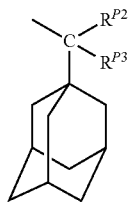

($R^P$-1-3)

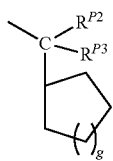

($R^P$-1-4)

wherein g is an integer from 1 to 3.

Specific examples of the alkali-labile group represented by $R^P$ include groups shown by the following formulas (Z-1) to (Z-3).

[Chemical Formula 14]

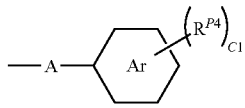

(Z-1)

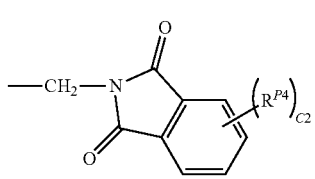

(Z-2)

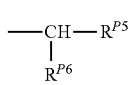

(Z-3)

wherein the following formula represents an aromatic hydrocarbon group,

[Chemical Formula 15]

A represents a single bond or —$CH_2$—, $R^{P4}$ represents a substituent that may include a fluorine atom, provided that a plurality of $R^{P4}$ may be either the same or different when a plurality of $R^{P4}$ are present, C1 is an integer from 0 to 5, C2 is an integer from 0 to 4, provided that a plurality of $R^{P4}$ may be either the same or different when C1 is an integer from 2 to 5 or C2 is an integer from 2 to 4, and $R^{P5}$ and $R^{P6}$ individually represent a hydrogen atom, a fluorine atom, or an alkyl group having 1 to 10 carbon atoms that may be substituted with a fluorine atom, provided that $R^{P5}$ and $R^{P6}$ may bond to each other to form a monovalent alicyclic hydrocarbon group having 4 to 20 carbon atoms that may be substituted with a fluorine atom together with the carbon atom bonded to $R^{P5}$ and $R^{P6}$.

The number of carbon atoms of the ring skeleton of the aromatic hydrocarbon group (see the following formula) in the formula (Z-1) is preferably 6 to 15. Specific examples of such a ring skeleton include a benzene ring, a naphthalene ring, a phenanthrene ring, an anthracene ring, and the like.

[Chemical Formula 16]

A carbocation eliminated from the ester group is stabilized due to the aromatic ring, so that the reactivity of the elimination reaction can be improved. A benzene ring is preferable from the viewpoint of reactivity.

Examples of the substituent represented by $R^{P4}$ in the formulas (Z-1) and (Z-2) include —$R^{P41}$, —$R^{P42}$—O—$R^{P41}$, —$R^{P42}$—CO—$R^{P41}$, —$R^{P42}$—CO—O$R^{P41}$, —$R^{P42}$—O—CO—$R^{P41}$, —$R^{P42}$—OH, —$R^{P42}$—CN, and —$R^{P42}$—COOH.

Note that $R^{P41}$ represents a monovalent chain-like saturated hydrocarbon group having 1 to 10 carbon atoms, a monovalent alicyclic saturated hydrocarbon group having 3 to 20 carbon atoms, or a monovalent aromatic hydrocarbon group having 6 to 30 carbon atoms. These groups may be substituted with one or more of one type of substituent, or may be substituted with one or more of each of a plurality of types of substituent. Examples of the substituent include a halogen atom (fluorine atom, chlorine atom, bromine atom, or iodine atom) and alkyl halide groups. Among these, a fluorine atom is preferable.

$R^{P42}$ represents a single bond, a divalent chain-like saturated hydrocarbon group having 1 to 10 carbon atoms, a divalent alicyclic saturated hydrocarbon group having 3 to 20 carbon atoms, or a divalent aromatic hydrocarbon group having 6 to 30 carbon atoms. These groups may be substituted with one or more of one type of substituent, or may be substituted with one or more of each of a plurality of types of substituent. Examples of the substituent include a halogen atom (fluorine atom, chlorine atom, bromine atom, or iodine atom) and alkyl halide groups. Among these, a fluorine atom is preferable.

The alkali-labile group represented by $R^P$ is preferably the alkali-labile group shown by the formula (Z-1) or (Z-3) from the viewpoint of ease of production.

The alkali-labile group shown by the formula (Z-1) is preferably a substituted phenyl group that includes a fluorine atom or a substituted benzyl group that includes a fluorine atom. The hydrophobicity can be significantly reduced upon dissociation of $R^P$ due to a fluorine atom while achieving improved hydrophobicity during liquid immersion lithography.

The substituted phenyl group that includes a fluorine atom is preferably a group obtained by substituting one hydrogen atom of a phenyl group with —$CF_3$. It is more preferable that —$CF_3$ is bonded at the para position.

The substituted benzyl group that includes a fluorine atom preferably includes a fluorine atom that substitutes the benzene ring instead of the hydrogen atom of the methylene group. Therefore, the reactivity of the ester group can be improved by bonding a unit that includes an electron-withdrawing group to the specific α-position carbon in the formulas (1-1) to (1-3) while suppressing an excessive increase in reactivity, so that a situation in which $R^P$ dissociates during liquid immersion lithography can be prevented. Moreover, the storage stability can be improved. The substituted benzyl group that includes a fluorine atom is more preferably a group obtained by substituting one hydrogen atom of a benzene ring with —$CF_3$. It is still more preferable that —$CF_3$ is bonded at the para position.

The alkali-labile group shown by the formula (Z-3) is preferably an alkyl group having 1 to 10 carbon atoms, and more preferably an alkyl group having 1 to 6 carbon atoms (e.g., methyl group, ethyl group, 1-propyl group, 2-propyl group, 1-butyl group, or 2-butyl group). The alkali-labile group shown by the formula (Z-3) is still more preferably an alkyl group having 1 to 3 carbon atoms. It is preferable that the alkyl group be substituted with a fluorine atom. The hydrophobicity can be significantly reduced upon dissociation of $R^P$ due to a fluorine atom while achieving improved hydrophobicity during liquid immersion lithography. When the alkyl group is substituted with a fluorine atom, it is preferable that the alkyl group has 2 or more carbon atoms, and the fluorine atom is bonded to the carbon atom other than that at the α-position, from the viewpoint of suppressing an excessive increase in reactivity.

Specific examples of the repeating unit (a1) that includes a group shown by any of the formulas (1-1) to (1-3) include repeating units shown by the following formulas (P-1) to (P-3).

[Chemical Formula 17]

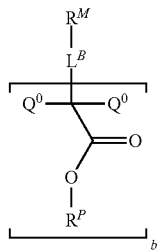
(P-1)

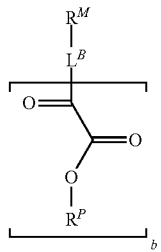
(P-2)

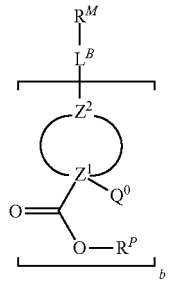
(P-3)

wherein $R^M$ represents any of groups shown by the following formulas,

[Chemical Formula 18]

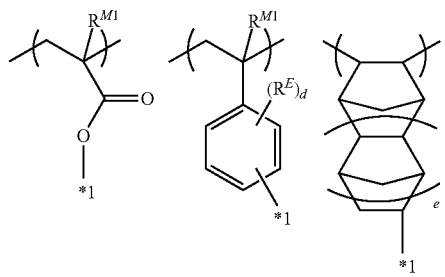

wherein $R^{M1}$ represents a hydrogen atom, a fluorine atom, an alkyl group having 1 to 5 carbon atoms, or a fluoroalkyl group having 1 to 5 carbon atoms, $R^E$ represents a substituent, d is an integer from 0 to 4, provided that a plurality of $R^E$ may be either the same or different when d is an integer from 2 to 4, e is 0 or 1, "*1" indicates a bonding hand bonded to $L^B$, $L^B$ represents a single bond or a (b+1)-valent linking group, b is 1 when $L^B$ represents a single bond, and is an integer from 1 to 5 when $L^B$ does not represent a single bond, provided that a plurality of $R^P$, a plurality of $Z^2$, and a plurality of $Q^0$ may respectively be either the same or different when b is an integer from 2 to 5, and $R^P$, $Q^0$, $Z^1$, and $Z^2$ are the same as defined for the formulas (1-1) to (1-3). Examples of the substituent represented by $R^E$ include those mentioned above in connection with $R^{P4}$. d is preferably an integer from 0 to 2, and more preferably 0, from the viewpoint of ease of production.

Repeating units shown by the following formulas (1p) to (3p) are preferable as the repeating units shown by the formulas (P-1) to (P-3) from the viewpoint of ease of production and light absorption when using ArF excimer laser light in an exposure step of a resist pattern-forming method described later.

$R^{M1}$ preferably represents a hydrogen atom or an alkyl group, and more preferably a hydrogen atom or a methyl group.

Specific examples of the repeating units shown by the formulas (1p) and (3p) include repeating units shown by the following formulas (1p-1) to (1p-5) and (3p-1) to (3p-4).

[Chemical Formula 19]

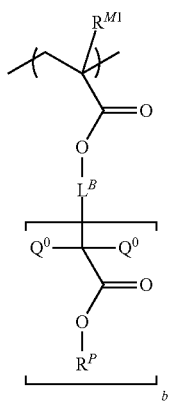
(1p)

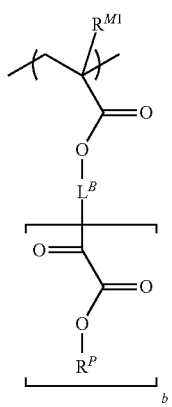
(2p)

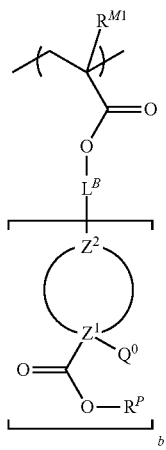
(3p)

wherein $R^{M1}$, $L^B$, $Q^0$, $Z^1$, $Z^2$, b, and $R^P$ are the same as defined for the formulas (P-1) to (P-3).

[Chemical Formula 20]

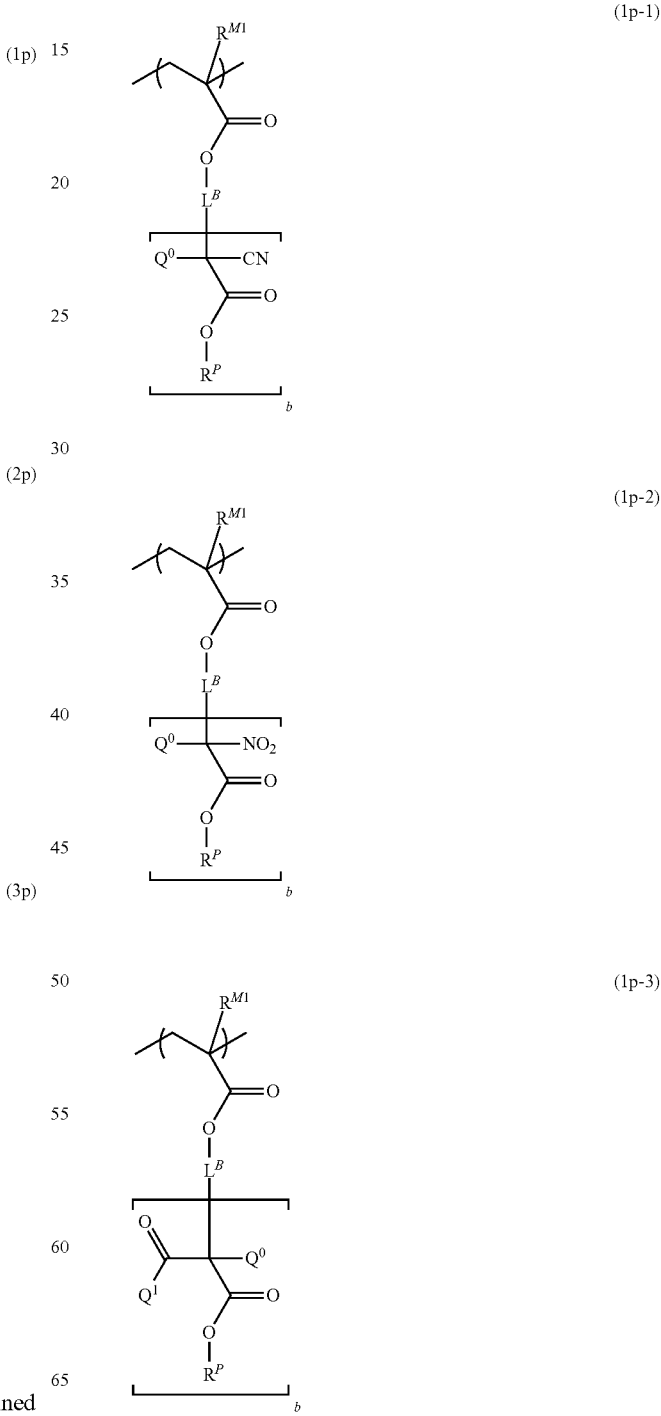

(1p-4)

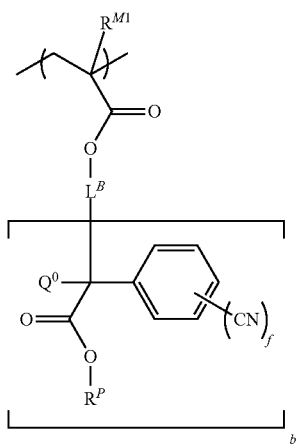

(1p-5)

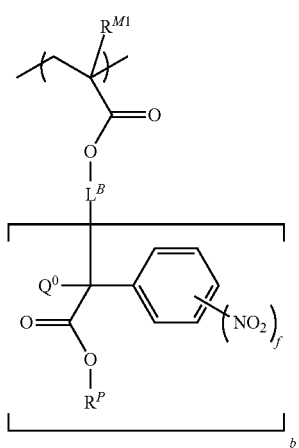

[Chemical Formula 21]

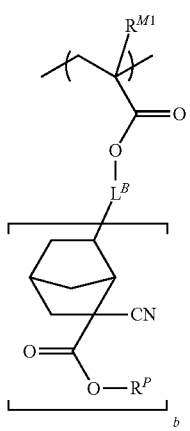

(3p-1)

(3p-2)

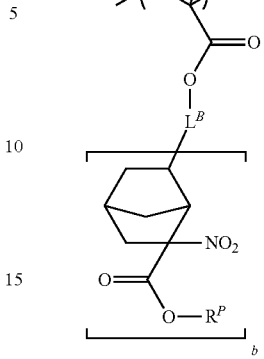

(3p-3)

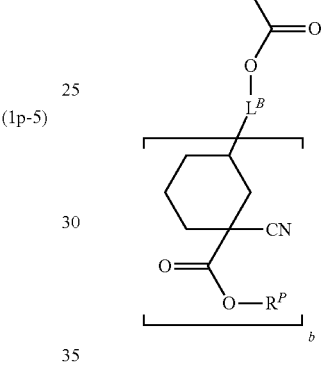

(3p-4)

wherein $Q^1$ represents a hydrogen atom or a monovalent hydrocarbon group (refer to the above description), f is an integer from 1 to 5, preferably 1 or 2, and more preferably 1, and $R^{M1}$, $Q^0$, $R^P$, and $L^B$ are the same as defined for the formulas (1p) to (3p).

Examples of the (b+1)-valent linking group (L) represented by $L^B$ include (b+1)-valent hydrocarbon group having 1 to 20 carbon atoms. The methylene group of the (b+1)-valent hydrocarbon group having 1 to 20 carbon atoms may be substituted with an oxygen atom, a sulfur atom, —NR'— (wherein R' represents a hydrogen atom or a monovalent organic group), a carbonyl group, —CO—O—, or —CO—NH—. The (b+1)-valent linking group represented by $L^B$ may include a lactone structure. The (b+1)-valent hydrocarbon group represented by $L^B$ may be a chain-like hydrocarbon group, an alicyclic hydrocarbon group, an aromatic hydrocarbon group, or a combination thereof. The (b+1)-valent hydrocarbon group represented by $L^B$ may be saturated or unsaturated.

$L^B$ in the formulas (1p) and (2p) preferably represents a (b+1)-valent linking group (L) rather than a single bond. When $L^B$ represents a (b+1)-valent linking group, $R^P$ is isolated from the main chain of the polymer (A) due to the (b+1)-valent linking group. Therefore, reactivity when $R^P$ dissociates can be improved. When $L^B$ represents a divalent linking group (L), the number of carbon atoms present between the oxygen atom bonded to the main chain and the carbon atom at the α-position with respect to the end ester group is preferably 1 to 6, and more preferably 1 to 3. If the number of carbon atoms is within the above range, a situation in which the distance between the main chain of the polymer (A) and $R^P$ increases to a large extent can be prevented. This makes it possible to prevent an excessive decrease in the glass transition temperature (Tg) of the polymer (A). In this case, the lithographic performance is advantageously improved.

The divalent linking group represented by $L^B$ is preferably a chain-like saturated hydrocarbon group having 1 to 6 carbon atoms or an aliphatic saturated hydrocarbon group having 3 to 6 carbon atoms, and more preferably an alkanediyl group having 1 to 3 carbon atoms (e.g., methanediyl group, ethanediyl group, n-propanediyl group, or i-propanediyl group).

$L^B$ in the formula (3p) preferably represents a single bond. Since the cyclic hydrocarbon group is present between the ester group and the main chain in the formula (3p), a situation in which the distance between the main chain of the polymer (A) and $R^P$ increases to a large extent can be prevented when $L^B$ represents a single bond.

Among the repeating units shown by the formulas (1p-1) to (1p-5), (2p), and (3p-1) to (3p-4), the repeating units shown by the formulas (1p-1) to (1p-3) and (2p) are preferable from the viewpoint of an improvement in reactivity of the ester group and ease of production.

b in the formulas (1p) to (3p), (1p-1) to (1p-5), (2p), and (3p-1) to (3p-4) is preferably 1 or 2, and more preferably 1.

Specific examples of the repeating unit (a1) wherein b is 1 and $L^B$ represents a preferable structure include repeating units shown by the following formulas (1p-1-1) to (1p-1-7), (1p-2-1) to (1p-2-7), (1p-3-1) to (1p-3-3), (2p-1) to (2p-3), and (3p-1-1) to (3p-3-1).

[Chemical Formula 22]

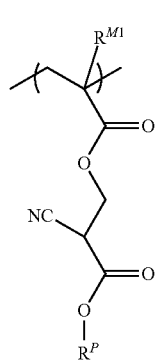
(1p-1-1)

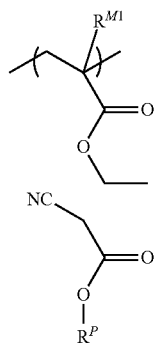
(1p-1-2)

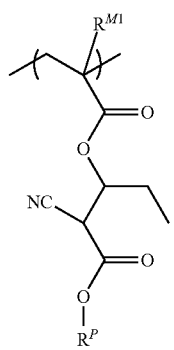
(1p-1-3)

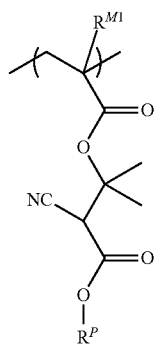
(1p-1-4)

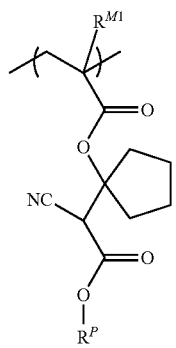
(1p-1-5)

(1p-1-6)
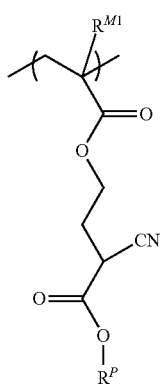
(1p-1-7)
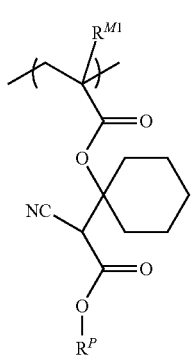
(1p-2-1)
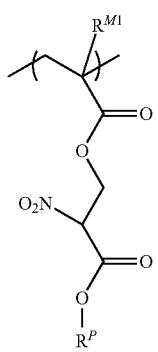
(1p-2-2)
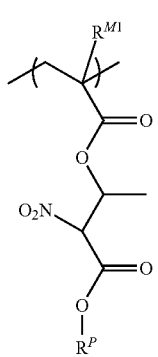
(1p-2-3)
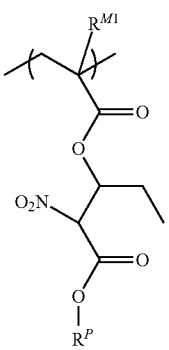
(1p-2-4)
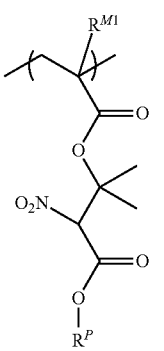
(1p-2-5)
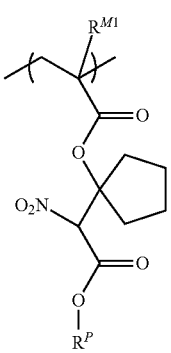
(1p-2-6)
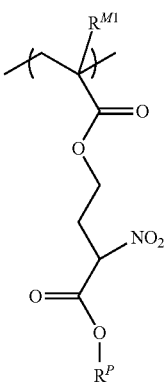

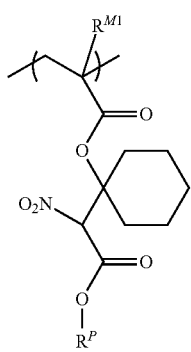 (1p-2-7)
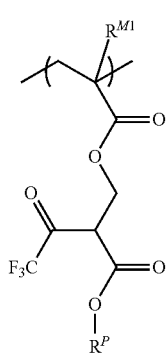 (1p-3-1)
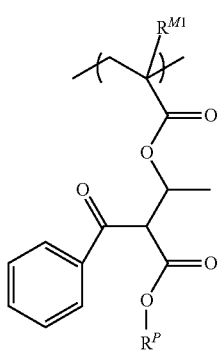 (1p-3-2)
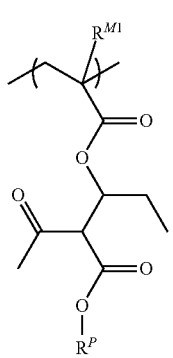 (1p-3-3)
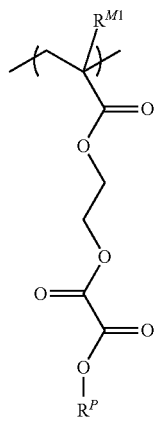 (2p-1)
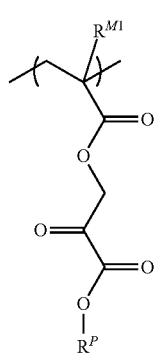 (2p-2)
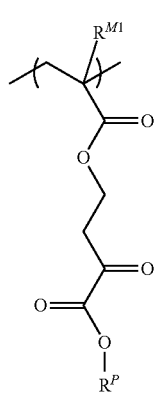 (2p-3)
[Chemical Formula 23]
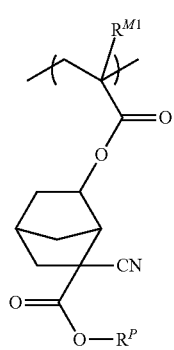 (3p-1-1)

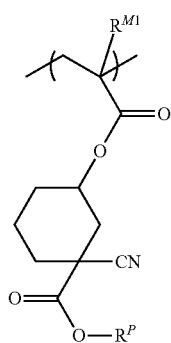

wherein $R^{M1}$ and $R^P$ are the same as defined for the formulas (1p) to (3p).

Among these, the repeating units shown by the formulas (1p-1-1) to (1p-1-6) and (1p-2-6) are preferable from the viewpoint of improving the reactivity of the ester group. Specific examples of the repeating units shown by the formulas (1-1-1) to (1p-1-5) and (1p-2-6) wherein $R^P$ represents an alkali-labile group include repeating units shown by the following formulas.

[Chemical Formula 24]

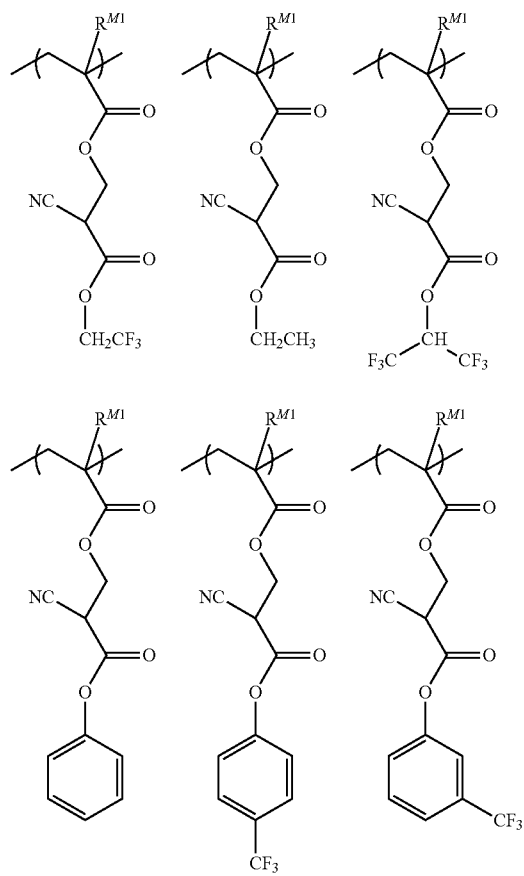

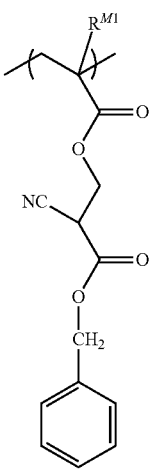
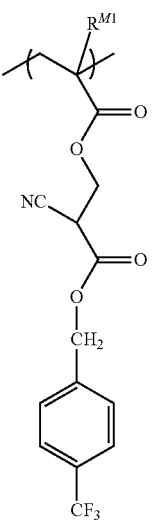
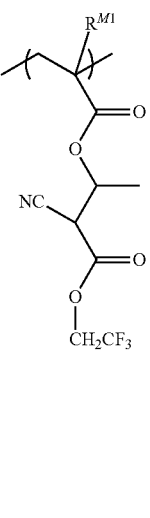

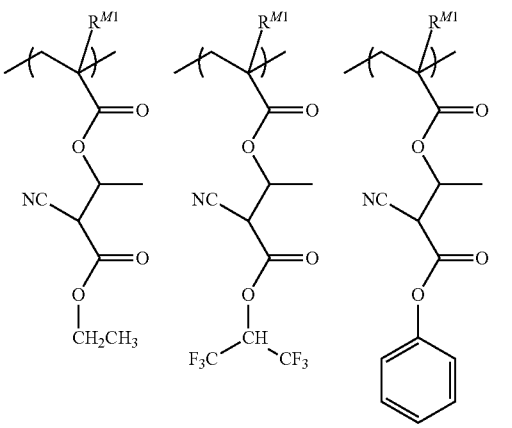

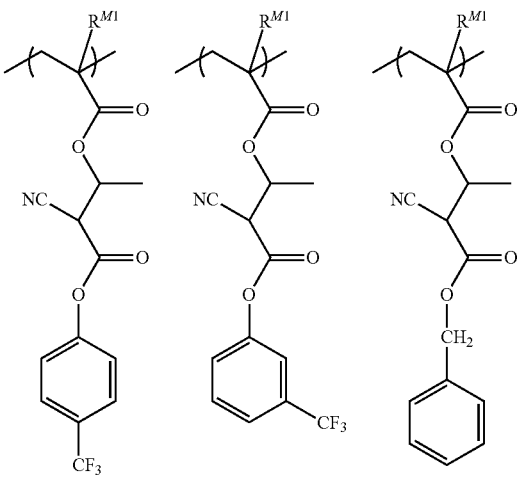

[Chemical Formula 25]
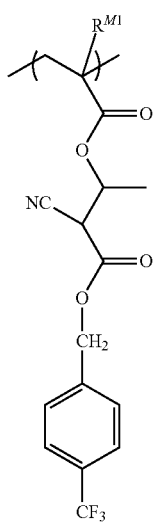
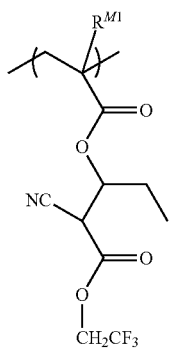
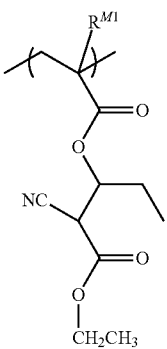
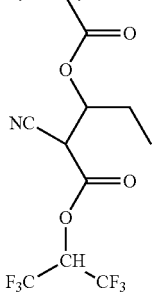
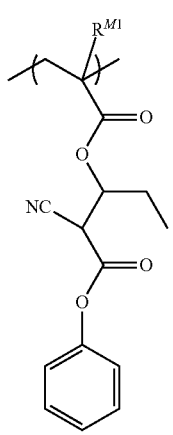
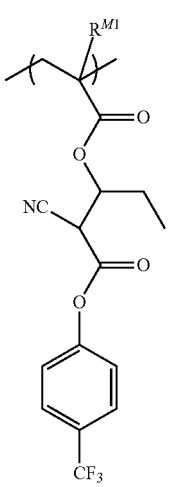
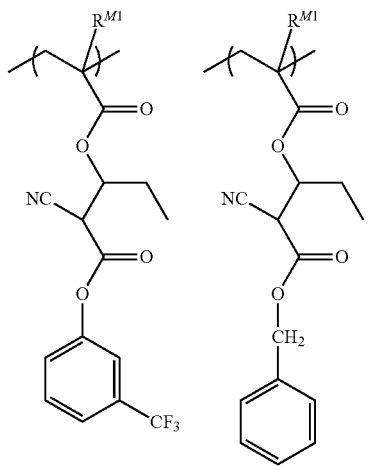
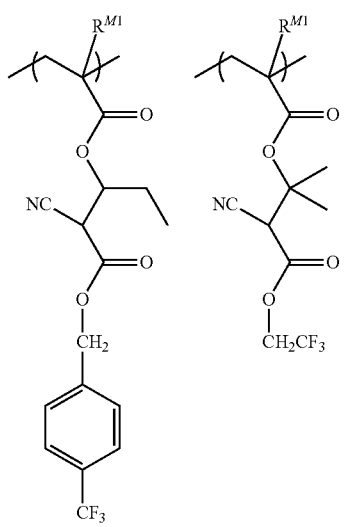
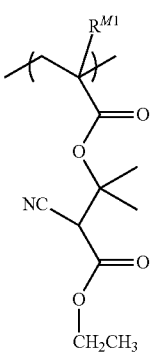
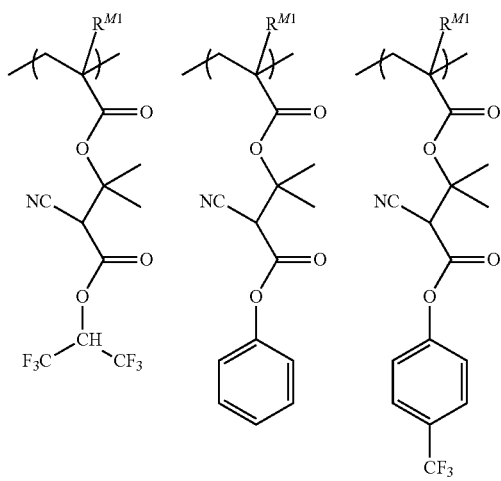

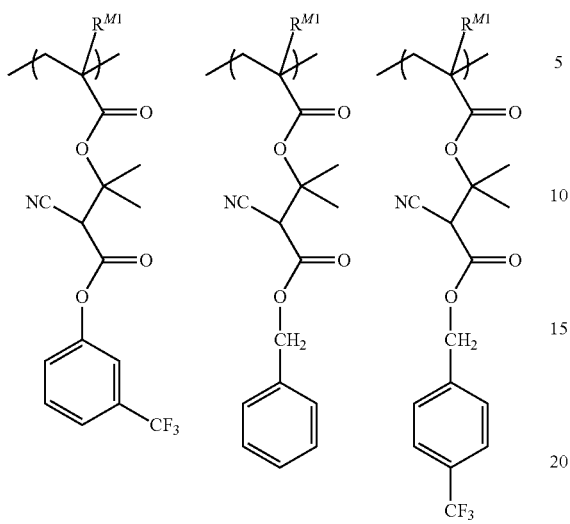
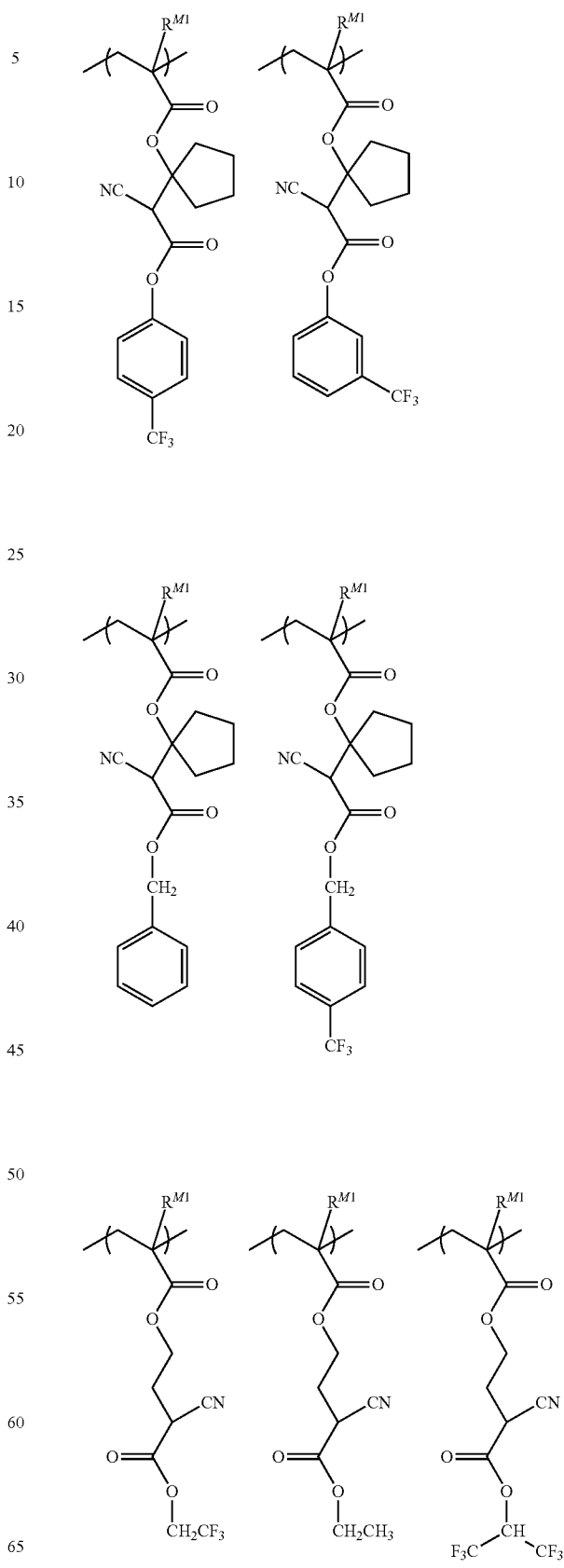

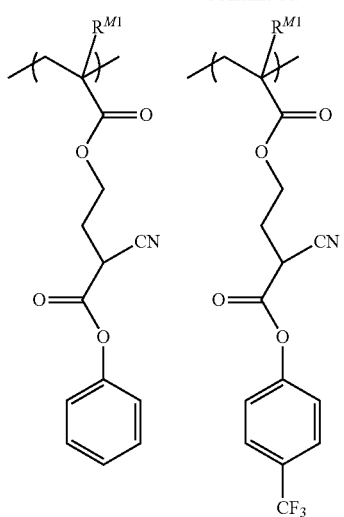
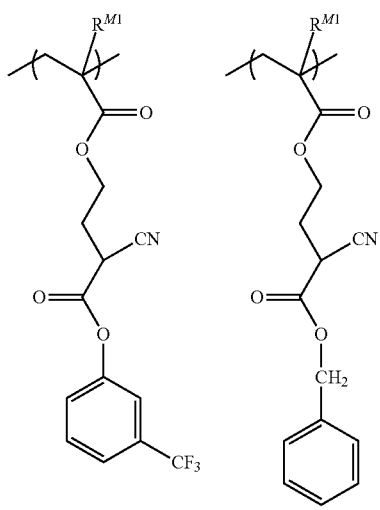
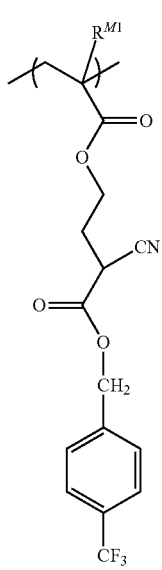
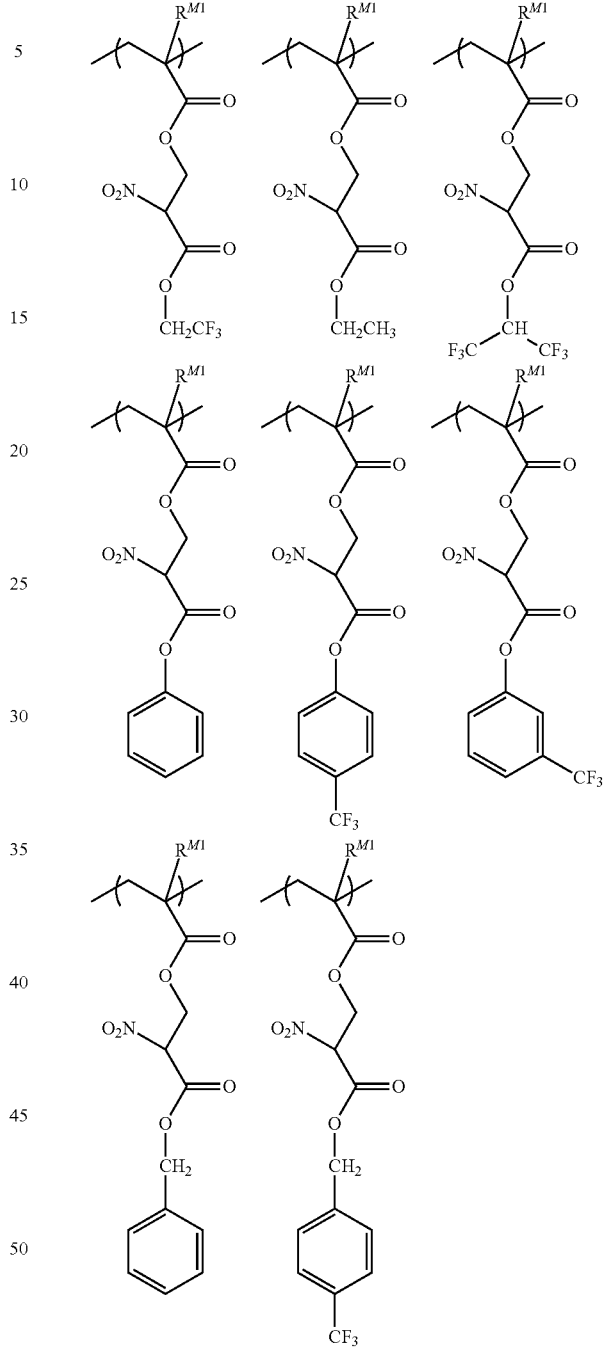

wherein $R^{M1}$ is the same as defined for the formulas (1p) to (3p).

The content of the repeating unit (a1) in the polymer (A) is preferably 20 to 100 mol %, and more preferably 30 to 100 mol %, based on the total repeating units included in the polymer (A). If the content of the repeating unit (a1) is within the above range, a sufficient number (amount) of carboxylic acid units are formed in the exposed area of the polymer (A) when $R^P$ represents an acid-labile group, so that the exposed area of the polymer (A) can be sufficiently dissolved in a developer. When $R^P$ represents an alkali-labile group, the surface of the resist film exhibits moderate hydrophobicity during liquid immersion lithography, and the hydrophobicity of the surface of the resist film promptly decreases before development. The polymer (A) may include only one type of repeating unit (a1), or may include two or more types of repeating unit (a1).

Examples of a monomer that produces the repeating unit (a1) include monomers shown by the following formulas (M-1) to (M-3).

[Chemical Formula 27]

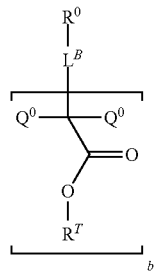

(M-1)

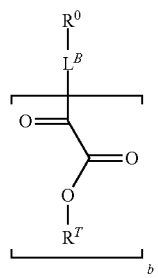

(M-2)

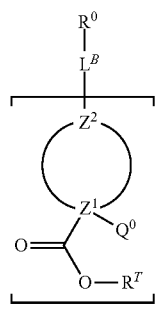

(M-3)

wherein $R^0$ represents any of groups shown by the following formulas,

[Chemical Formula 28]

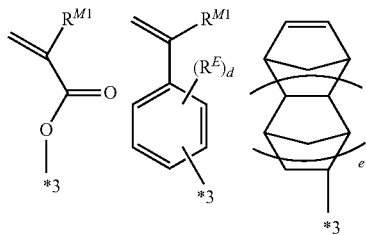

"*3" indicates a bonding hand bonded to $L^B$, $R^T$ represents a hydrogen atom or a monovalent organic group, and $R^{M1}$, $L^B$, $Q^0$, $Z^1$, $Z^2$, $R^E$, d, and e are the same as defined for the formulas (P-1) to (P-3).

Examples of the monovalent organic group represented by $R^T$ in the formulas (M-1) to (M-3) include those mentioned above in connection with $R^P$. The carboxylic acid compound wherein $R^T$ represents a hydrogen atom may be used as a precursor that produces the compound wherein $R^T$ represents a monovalent organic group. It is preferable that the monomers shown by the formulas (M-1) to (M-3) include a fluorine atom so that the resist film exhibits hydrophobicity during liquid immersion lithography due to the repeating unit (a1). It is preferable that $L^B$ represent a (b+1)-valent linking group (L) from the viewpoint of improving the reactivity of the repeating unit (a1).

The polymer (A) must include a fluorine atom so that the surface of the resist film exhibits high hydrophobicity during liquid immersion lithography. The repeating unit (a1) may or may not include a fluorine atom. When the repeating unit (a1) does not include a fluorine atom, the polymer (A) must include any of fluorine-containing repeating units (a2) to (a6) described below. The polymer (A) may include any of the fluorine-containing repeating units (a2) to (a6) even if the repeating unit (a1) includes a fluorine atom. The polymer (A) may also include any of additional repeating units (a7) to (a9) described below. The repeating units (a2) to (a9) are described below.

<Fluorine-Containing Repeating Unit>
<Repeating Unit (a2)>

The polymer (A) may include a repeating unit shown by the following formula (2) as the repeating unit (a2).

[Chemical Formula 29]

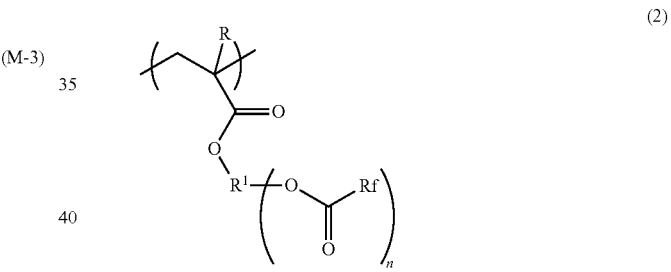

(2)

wherein R represents a hydrogen atom, a fluorine atom, a methyl group, or a trifluoromethyl group, $R^1$ represents an (n+1)-valent linking group, Rf represents a monovalent hydrocarbon group that includes a fluorine atom, and n is an integer from 1 to 3, provided that a plurality of Rf may be either the same or different when n is 2 or 3.

—CO—Rf in the formula (2) functions as an alkali-labile group. Therefore, when the polymer (A) includes the repeating unit (a2), the solubility of the polymer (A) in an alkaline developer can be improved, and the hydrophobicity of the surface of the resist film after development can be reduced.

Examples of the (n+1)-valent linking group represented by $R^1$ in the formula (2) include those mentioned above in connection with the (b+1)-valent linking group (L) represented by $L^B$ in the formulas (1p) to (3p).

Examples of the monovalent chain-like hydrocarbon group having 1 to 30 carbon atoms that includes a fluorine atom represented by Rf in the formula (2) include groups obtained by substituting 1 to 10 hydrogen atoms of a chain-like hydrocarbon group having 1 to 30 carbon atoms with a fluorine atom.

Examples of the monovalent alicyclic hydrocarbon group having 3 to 30 carbon atoms that includes a fluorine atom represented by Rf in the formula (2) include a group obtained by substituting 1 to 10 hydrogen atoms of an alicyclic hydrocarbon group having 3 to 30 carbon atoms with a fluorine atom.

The group represented by Rf is preferably a perfluoroalkyl group having 1 to 4 carbon atoms, a monoperfluoroalkylmethyl group having 2 to 5 carbon atoms, or a diperfluoroalkylmethyl group having 3 to 5 carbon atoms, and particularly preferably a trifluoromethyl group or a perfluoropropyl group, since the surface of the resulting resist film has a high receding contact angle before development.

Specific examples of the repeating unit (a2) include repeating units shown by the following formulas (2-1) to (2-6).

[Chemical Formula 30]

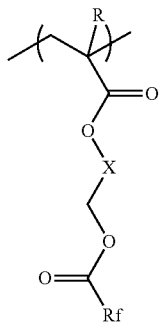
(2-1)

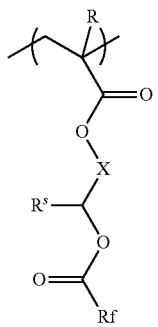
(2-2)

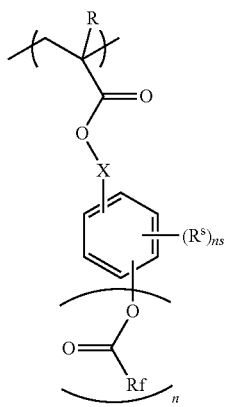
(2-3)

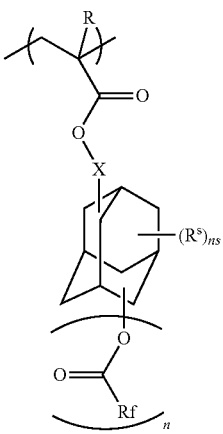
(2-4)

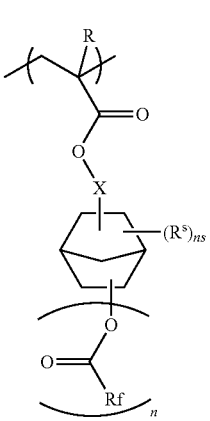
(2-5)

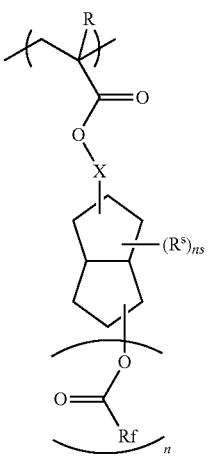
(2-6)

wherein R, Rf, and n are the same as defined above, X represents a divalent linking group, $R^S$ represents a substituent, and ns is an integer from 0 to 3.

Examples of the divalent linking group represented by X include divalent chain-like hydrocarbon groups having 1 to 30 carbon atoms, divalent alicyclic hydrocarbon groups having 3 to 30 carbon atoms, divalent aromatic hydrocarbon groups having 6 to 30 carbon atoms, and divalent groups formed by any of these groups and an ether group, an ester group, a carbonyl group, an imino group, or an amide group. The divalent linking group may be substituted with a substituent. Specific examples of the substituent include those mentioned above in connection with $R^{P4}$ in the formulas (Z-1) and (Z-2).

Examples of the substituent represented by $R^S$ include those mentioned above in connection with $R^{P4}$ in the formulas (Z-1) and (Z-2).

Specific examples of the repeating units shown by the formulas (2-1) to (2-6) include repeating units shown by the following formulas (2p-1) to (2p-8).

[Chemical Formula 31]

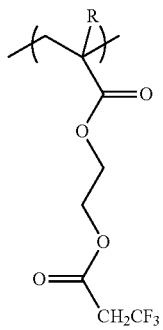

(2p-1)

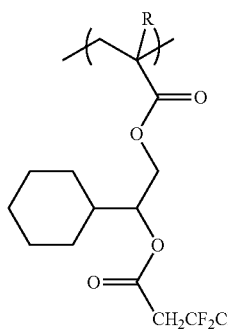

(2p-2)

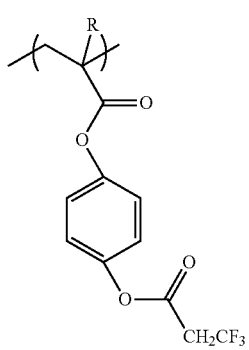

(2p-3)

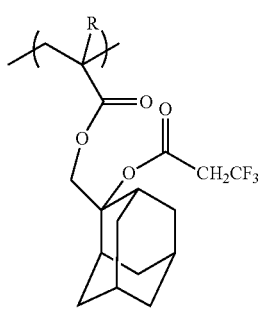

(2p-4)

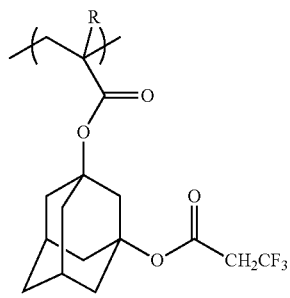

(2p-5)

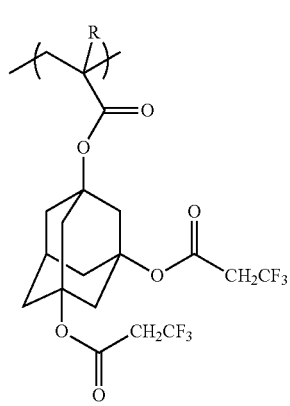

(2p-6)

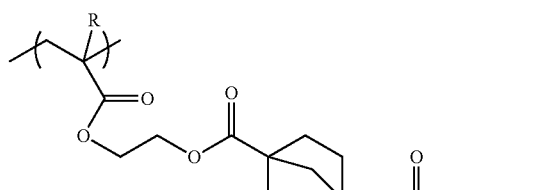

(2p-7)

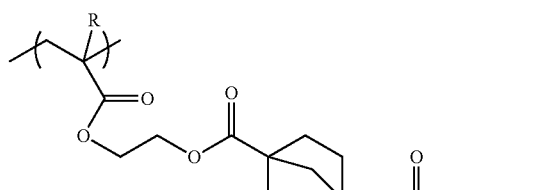

(2p-8)

wherein R is the same as defined for the formula (2-1).

The content of the repeating unit (a2) in the polymer (A) is preferably 0 to 50 mol %, more preferably 0 to 30 mol %, and particularly preferably 0 to 20 mol %, based on the total repeating units included in the polymer (A). The polymer (A) may include only one type of repeating unit (a2), or may include two or more types of repeating unit (a2).

<Repeating Unit (a3)>

The polymer (A) may include a repeating unit shown by the following formula (3) as the repeating unit (a3).

[Chemical Formula 32]

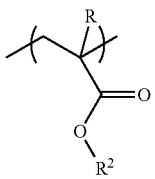

(3)

wherein R and $R^2$ are the same as defined for R and Rf in the formula (2).

Specific examples of the monovalent hydrocarbon group represented by $R^2$ in the formula (3) include those mentioned above in connection with Rf in the formula (2). $R^2$ preferably represents a chain-like hydrocarbon group having 1 to 6 carbon atoms that includes a fluorine atom, or an alicyclic hydrocarbon group having 4 to 20 carbon atoms that includes a fluorine atom.

Specific examples of the repeating unit (a3) include the repeating units disclosed in paragraphs [0214] and [0215] of Japanese Patent Application Publication (KOKAI) No. 2007-304537, and repeating units shown by the following formulas.

[Chemical Formula 33]

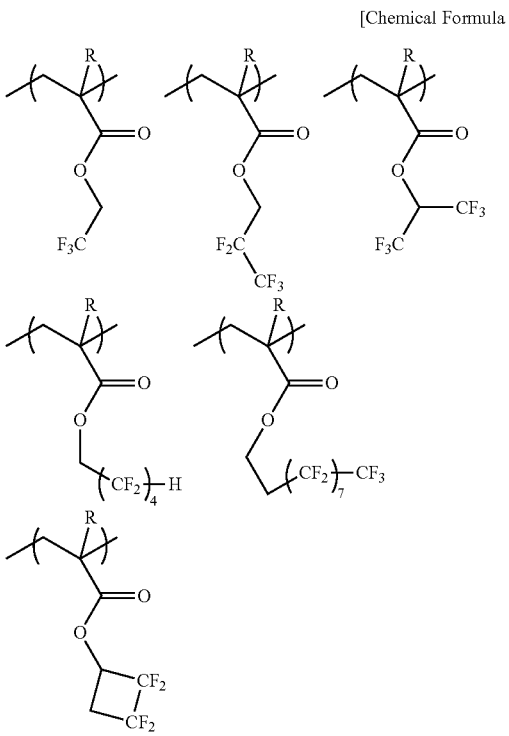

wherein R is the same as defined for the formula (3).

The content of the repeating unit (a3) in the polymer (A) is preferably 0 to 50 mol %, more preferably 0 to 30 mol %, and particularly preferably 0 to 25 mol %, based on the total repeating units included in the polymer (A). The polymer (A) may include only one type of repeating unit (a3), or may include two or more types of repeating unit (a3).

<Repeating Unit (a4)>

The polymer (A) may include a repeating unit shown by the following formula (4) as the repeating unit (a4).

[Chemical Formula 34]

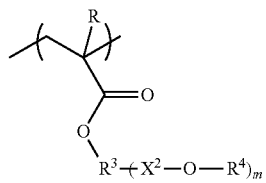

(4)

wherein R is the same as defined for the formula (2), $R^3$ represents an (m+1)-valent linking group, $X^2$ represents a divalent linking group that includes at least one fluorine atom, $R^4$ represents a hydrogen atom or a monovalent organic group, and m is an integer from 1 to 3, provided that a plurality of $X^2$ and a plurality of $R^4$ may respectively be either the same or different when m is 2 or 3.

Specific examples of the linking group represented by $R^3$ in the formula (4) include those mentioned above in connection with $R^1$ in the formula (2). When the linking group represented by $R^3$ is a hydrocarbon group, an oxygen atom, a sulfur atom, —NR'— (wherein R' represents a hydrogen atom or a monovalent organic group), a carbonyl group, —CO—O—, or —CO—NH— may be bonded to the end of the linking group represented by $R^3$ that is bonded to $X^2$.

When $R^4$ in the formula (4) represents a hydrogen atom, the solubility of the polymer (A) in an alkaline developer can be improved.

Examples of the monovalent organic group represented by $R^4$ in the formula (4) include an acid-labile group, an alkali-labile group, and a substituted or unsubstituted hydrocarbon group having 1 to 30 carbon atoms.

Specific examples of the acid-labile group include those mentioned above in connection with $R^P$ in the formulas (1-1) to (1-3).

Specific examples of the alkali-labile group include a group shown by the following formula (W-1).

[Chemical Formula 35]

(W-1)

wherein Rf is the same as defined for the formula (2).

$X^2$ in the formula (4) preferably represents a divalent chain-like hydrocarbon group having 1 to 20 carbon atoms that includes at least one fluorine atom. Specific examples of the divalent chain-like hydrocarbon group represented by $X^2$ include the groups shown by the following formulas (X2-1) to (X2-6).

[Chemical Formula 36]

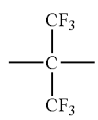

(X2-1)

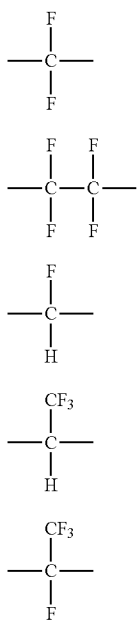

X² preferably represents the group shown by the formula (X2-1).

m in the formula (4) is an integer from 1 to 3. Therefore, the repeating unit (a4) includes one, two, or three R⁴. A plurality of R⁴ and a plurality of X² may respectively be either the same or different when m is 2 or 3. Specifically, a plurality of R⁴ may have either the same or a different structure when m is 2 or 3. When m is 2 or 3, a plurality of X² may be bonded to an identical carbon atom included in the linking group represented by R³, or may be bonded to different carbon atoms included in the linking group represented by R³.

Specific examples of the repeating unit (a4) include the repeating units disclosed in Japanese Patent Application Publication (KOKAI) No. 2007-204385 (particularly repeating units derived from the monomers described in paragraphs [0040], [0041], [0061], and [0077]).

Specific examples of the repeating unit (a4) are shown below.

[Chemical Formula 37]

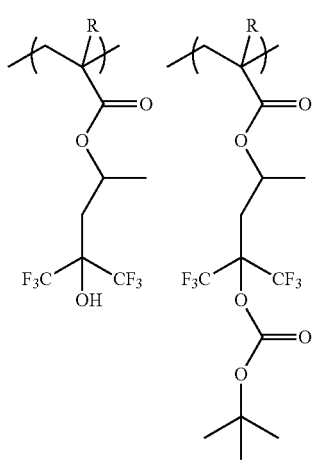

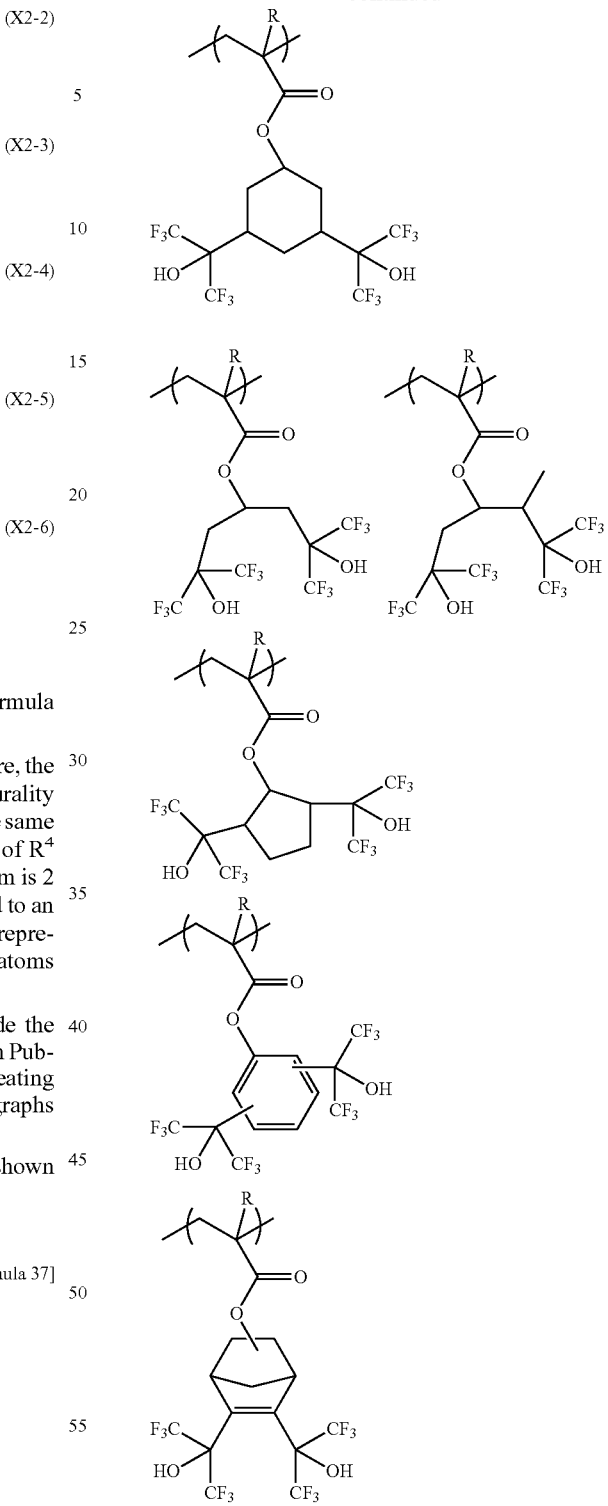

wherein R is the same as defined for the formula (4).

The content of the repeating unit (a4) in the polymer (A) is preferably 0 to 50 mol %, more preferably 5 to 40 mol %, and particularly preferably 0 to 30 mol %, based on the total repeating units included in the polymer (A). The polymer (A) may include only one type of repeating unit (a4), or may include two or more types of repeating unit (a4).

<Repeating Unit (a5)>

The polymer (A) may include a repeating unit shown by the following formula (5) as the repeating unit (a5).

[Chemical Formula 38]

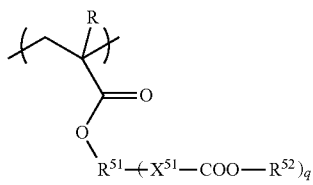
(5)

wherein R is the same as defined for the formula (2), $X^{51}$ and $R^{52}$ are the same as defined for $X^2$ and $R^4$ in the formula (2), $R^{51}$ represents a (q+1)-valent linking group, and q is an integer from 1 to 3, provided that a plurality of $X^{51}$ and a plurality of $R^{52}$ may respectively be either the same or different when q is 2 or 3.

Specific examples of the linking group represented by $R^{51}$ in the formula (5) include those mentioned above in connection with $R^3$ in the formula (4).

Examples of the monovalent organic group represented by $R^{52}$ in the formula (5) include an acid-labile group, an alkali-labile group, and a substituted or unsubstituted hydrocarbon group having 1 to 30 carbon atoms.

Specific examples of the acid-labile group include those mentioned above in connection with $R^P$ in the formulas (1-1) to (1-3). The acid-labile group is preferably the group shown by the formula ($R^P$-1).

Specific examples of the alkali-labile group include those mentioned above in connection with $R^P$ in the formulas (1-1) to (1-3).

$R^{52}$ in the formula (5) preferably represents a hydrogen atom. In this case, the solubility of the polymer (A) in an alkaline developer can be improved.

Specific examples of the linking group represented by $X^{51}$ in the formula (5) include those mentioned above in connection with $X^2$ in the formula (4). $X^{51}$ preferably represents a divalent chain-like hydrocarbon group having 1 to 20 carbon atoms that includes at least one fluorine atom, more preferably any of the groups shown by the formulas (X2-2) to (X2-6), and still more preferably the group shown by the formula (X2-2).

q in the formula (5) is an integer from 1 to 3. Therefore, the repeating unit (a5) includes one, two, or three $R^{52}$. A plurality of $R^{52}$ and a plurality of $X^{51}$ may respectively be either the same or different when q is 2 or 3. Specifically, a plurality of $R^{52}$ may have either the same or a different structure when q is 2 or 3. When q is 2 or 3, a plurality of $X^{51}$ may be bonded to an identical carbon atom included in the linking group represented by $R^{51}$, or may be bonded to different carbon atoms included in the linking group represented by $R^{51}$.

Specific examples of the repeating unit (a5) include the repeating units disclosed in Japanese Patent Application Publication (KOKAI) No. 2009-019199, the repeating units disclosed in Japanese Patent Application Publication (KOKAI) No. 2009-074085, repeating units shown by the following formulas (5-1a) and (5-1b), and the like.

[Chemical Formula 39]

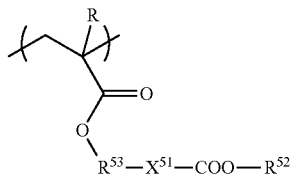
(5-1a)

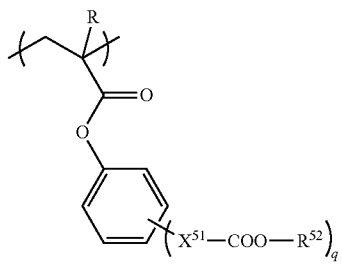
(5-1b)

wherein $R^{53}$ represents a divalent linear, branched, or cyclic saturated or unsaturated hydrocarbon group having 1 to 20 carbon atoms, and $X^{51}$, $R^{52}$, and q are the same as defined for the formula (5), provided that a plurality of $X^{51}$ and a plurality of $R^{52}$ may respectively be either the same or different when q is 2 or 3.

Specific examples of the repeating units shown by the formulas (5-1a) and (5-1b) include compounds shown by the following formulas (5p-1) to (5p-7)

[Chemical Formula 40]

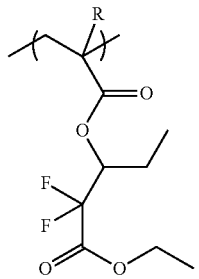
(5p-1)

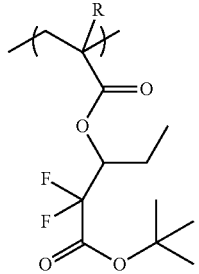
(5p-2)

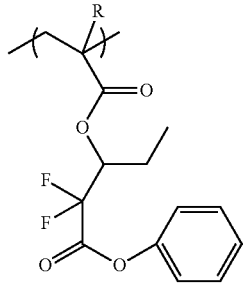
(5p-3)

(5p-4)

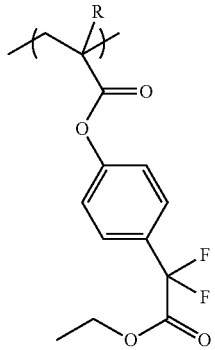

(5p-5)

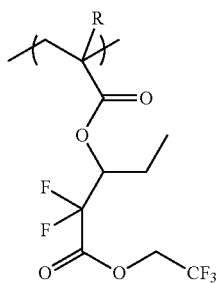

(5p-6)

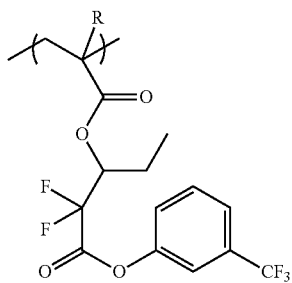

(5p-7)

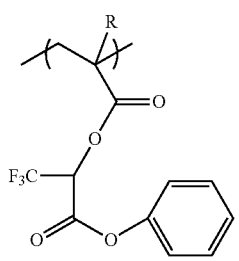

wherein R is the same as defined for the formula (5).

The content of the repeating unit (a5) in the polymer (A) is preferably 0 to 70 mol %, and more preferably 0 to 60 mol %, based on the total repeating units included in the polymer (A). The polymer (A) may include only one type of repeating unit (a5), or may include two or more types of repeating unit (a5).

<Repeating Unit (a6)>

The polymer (A) may include a repeating unit shown by the following formula (6) as the repeating unit (a6).

[Chemical Formula 41]

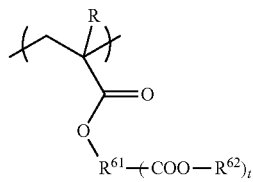

(6)

wherein R and $R^{62}$ are the same as defined for R and Rf in the formula (2). $R^{61}$ represents a (t+1)-valent linking group, and t is an integer from 1 to 3, provided that a plurality of $R^{62}$ may be either the same or different when t is 2 or 3.

Specific examples of the linking group represented by $R^{61}$ in the formula (6) include those mentioned above in connection with $R^3$ in the formula (4).

Specific examples of the monovalent hydrocarbon group represented by $R^{62}$ in the formula (6) include those mentioned above in connection with Rf in the formula (2). $R^{62}$ preferably represents a chain-like hydrocarbon group having 1 to 6 carbon atoms that includes a fluorine atom, or an alicyclic hydrocarbon group having 4 to 20 carbon atoms that includes a fluorine atom. $R^{62}$ included in the repeating unit (a6) functions as an alkali-labile group. Therefore, when the polymer (A) includes the repeating unit (a6), the solubility of the polymer (A) in an alkaline developer can be improved, and the hydrophobicity of the surface of the resist film obtained by development can be reduced.

t in the formula (6) is an integer from 1 to 3. Therefore, the repeating unit (a6) includes one, two, or three $R^{62}$. A plurality of $R^{62}$ may be either the same or different when t is 2 or 3. Specifically, a plurality of $R^{62}$ may have either the same or a different structure when t is 2 or 3. When t is 2 or 3, a plurality of —COO—$R^{62}$ may be bonded to an identical carbon atom included in the hydrocarbon group represented by $R^{62}$, or may be bonded to different carbon atoms included in the hydrocarbon group represented by $R^{62}$.

Specific examples of the repeating unit (a6) include the repeating units disclosed in Japanese Patent Application Publication (KOKAI) No. 2010-032994 (particularly (c-1-3) in paragraph [0152], and paragraphs [0155] and [0159] to [0162]), the repeating units disclosed in paragraphs [0063] to [0071] of Japanese Patent Application Publication (KOKAI) No. 2008-111103, repeating units shown by the following formulas (6-1a) and (6-1b), and the like.

[Chemical Formula 42]

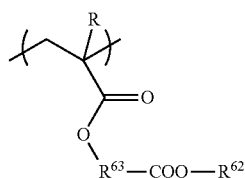

(6-1a)

-continued

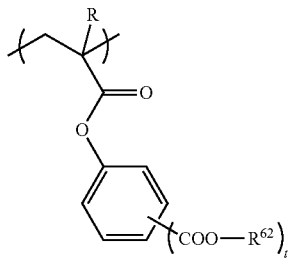
(6-1b)

wherein $R^{63}$ represents a divalent linear, branched, or cyclic saturated or unsaturated hydrocarbon group having 1 to 20 carbon atoms, and $R^{62}$ and t are the same as defined for the formula (6), provided that a plurality of $R^{62}$ may be either the same or different when t is 2 or 3.

Specific examples of the repeating units shown by the formulas (6-1a) and (6-1b) include repeating units shown by the following formulas (6p-1) to (6p-7)

[Chemical Formula 43]

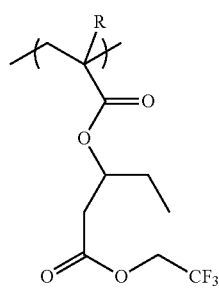
(6p-1)

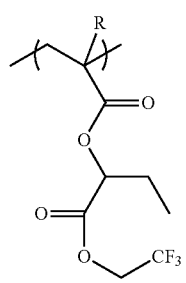
(6p-2)

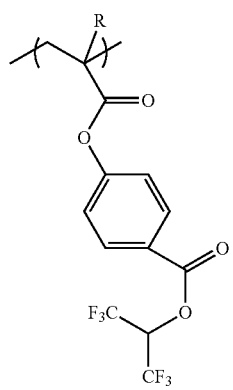
(6p-3)

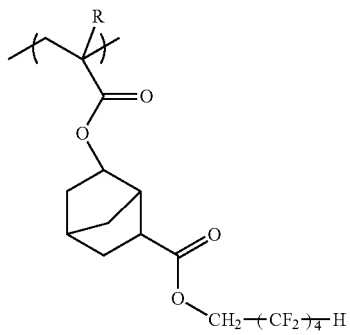
(6p-4)

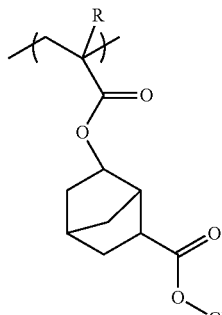
(6p-5)

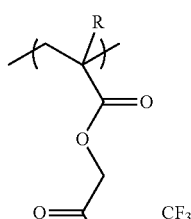
(6p-6)

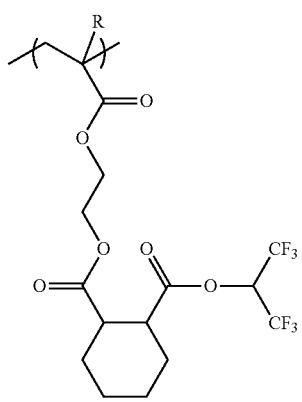
(6p-7)

wherein R is the same as defined for the formula (6).

The content of the repeating unit (a6) in the polymer (A) is preferably 0 to 50 mol %, more preferably 0 to 40 mol %, and particularly preferably 0 to 30 mol %, based on the total repeating units included in the polymer (A). The polymer (A) may include only one type of repeating unit (a6), or may include two or more types of repeating unit (a6).

<Additional Repeating Unit>

<Repeating unit (a7)>

The polymer (A) may include the repeating unit (a7) shown by the following formula (7).

[Chemical Formula 44]

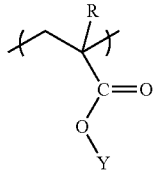
(7)

wherein R is the same as defined for the formula (2), and Y represents an acid-labile group.

Examples of the acid-labile group represented by Y include the group shown by the formula ($R^P$-1). Specific examples of the repeating unit (a7) include repeating units shown by the following formulas (7-1) to (7-4).

[Chemical Formula 45]

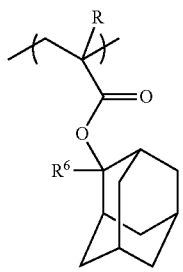
(7-1)

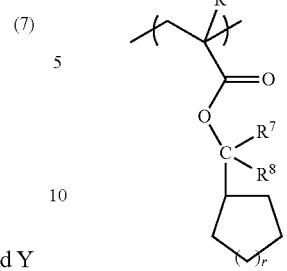
(7-2)

(7-3)

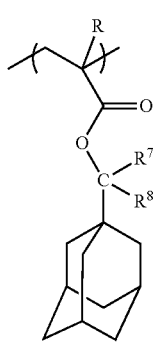

(7-4)

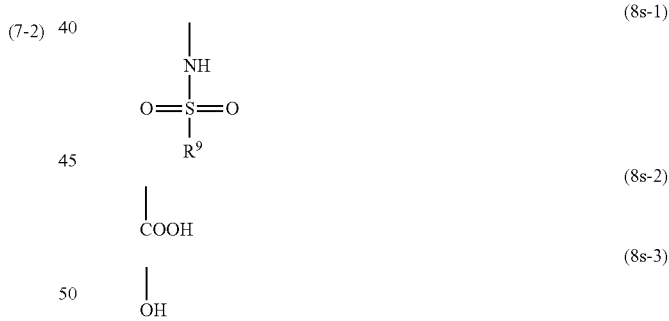

wherein R is the same as defined for the formula (7), $R^6$ to $R^8$ are respectively the same as defined for $R^{P1}$ to $R^{P3}$ in the formulas ($R^P$-1-1) to ($R^P$-1-4), provided that $R^7$ and $R^8$ may bond to each other to form a divalent alicyclic hydrocarbon group having 4 to 20 carbon atoms together with the carbon atom bonded to $R^7$ and $R^8$, and r is an integer from 1 to 3.

The content of the repeating unit (a7) in the polymer (A) is preferably 50 mol % or less, and more preferably 0 to 40 mol %, based on the total repeating units included in the polymer (A). The polymer (A) may include only one type of repeating unit (a7), or may include two or more types of repeating unit (a7).

<Repeating Unit (a8)>

The polymer (A) may include the repeating unit (a8) that includes an alkali-soluble group. The alkali-soluble group included in the repeating unit (a8) is preferably a functional group that includes a hydrogen atom having a pKa of 4 to 11 from the viewpoint of an improvement in solubility in a developer. Specific examples of such a functional group include functional groups shown by the following formulas (8s-1) to (8s-3), and the like.

[Chemical Formula 46]

$$\begin{array}{c} | \\ NH \\ | \\ O=S=O \\ | \\ R^9 \end{array}$$
(8s-1)

$$\begin{array}{c} | \\ COOH \end{array}$$
(8s-2)

$$\begin{array}{c} | \\ OH \end{array}$$
(8s-3)

wherein $R^9$ represents a hydrocarbon group having 1 to 10 carbon atoms that includes at least one fluorine atom.

The hydrocarbon group having 1 to 10 carbon atoms that includes at least one fluorine atom represented by $R^9$ in the formula (8s-1) is not particularly limited as long as the hydrocarbon group is obtained by substituting some or all of the hydrogen atoms of a hydrocarbon group having 1 to 10 carbon atoms with a fluorine atom. For example, $R^9$ preferably represents a trifluoromethyl group or the like.

Specific examples of the repeating unit (a8) include a structural unit derived from (meth)acrylic acid, the repeating units disclosed in paragraphs [0018] to [0022] of WO2009/041270, the repeating units disclosed in paragraph [0034] of WO2009/041270, and the repeating units disclosed in paragraph [0015] of WO2006/035790

The content of the repeating unit (a8) in the polymer (A) is normally 50 mol % or less, preferably 0 to 30 mol %, and more preferably 0 to 20 mol %, based on the total repeating units included in the polymer (A). The polymer (A) may include only one type of repeating unit (a8), or may include two or more types of repeating unit (a8).

<Repeating Unit (a9)>

The polymer (A) may include the repeating unit (a9) shown by the following formula (9). If the polymer (A) includes the repeating unit (a9), affinity to a developer can be improved.

[Chemical Formula 47]

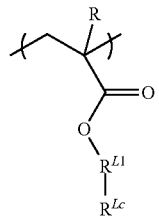

(9)

wherein R is the same as defined for the formula (2), $R^{L1}$ represents a single bond or a divalent linking group, and $R^{Lc}$ represents a monovalent organic group having a lactone structure or a monovalent organic group having a cyclic carbonate structure.

Specific examples of the divalent linking group ($R^{L1}$) included in the formula (9) include those mentioned above in connection with the divalent linking group (X) included in the repeating unit (a2), and the like.

Specific examples of the monovalent organic group having a lactone structure represented by $R^{LC}$ in the formula (9) include groups shown by the following formulas (Lc-1) to (Lc-6).

[Chemical Formula 48]

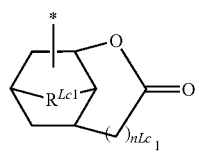

(Lc-1)

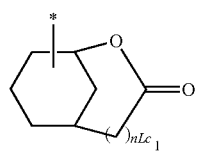

(Lc-2)

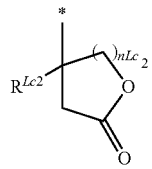

(Lc-3)

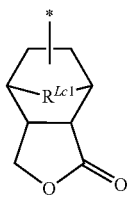

(Lc-4)

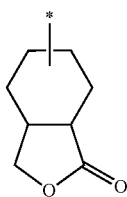

(Lc-5)

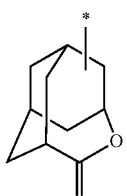

(Lc-6)

wherein $R^{Lc1}$ represents an oxygen atom or a methylene group, $R^{Lc2}$ represents a hydrogen atom or an alkyl group having 1 to 4 carbon atoms, $nLc_1$ is 0 or 1, $nLc_2$ is an integer from 0 to 3, and "*" indicates a bonding hand bonded to $R^{L1}$ in the formula (9). Note that the groups shown by the formulas (Lc-1) to (Lc-6) may be substituted with a substituent.

Examples of a substituent that may substitute the groups shown by the formulas (Lc-1) to (Lc-6) include the substituents mentioned above in connection with $R^C$ in the formula (1).

Specific examples of the repeating unit (a9) include the structural units disclosed in paragraphs [0054] to [0057] of Japanese Patent Application Publication (KOKAI) No. 2007-304537, the structural units disclosed in paragraphs [0086] to [0088] of Japanese Patent Application Publication (KOKAI) No. 2008-088343, and structural units shown by the following formulas (9-1a) to (9-1j).

[Chemical Formula 49]

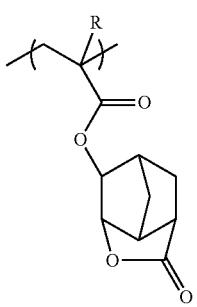

(9-1a)

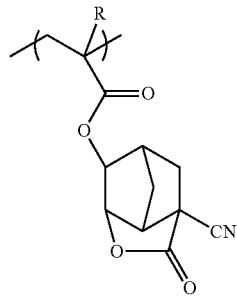 (9-1b)
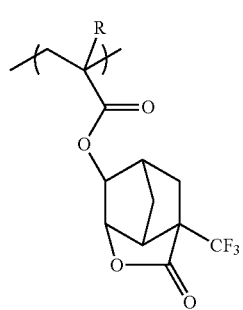 (9-1c)
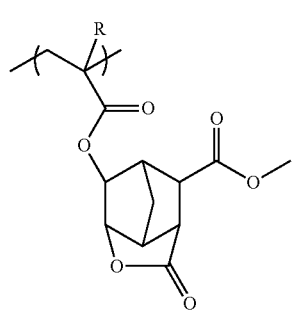 (9-1d)
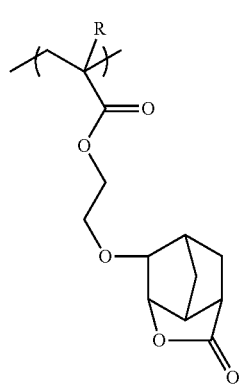 (9-1e)
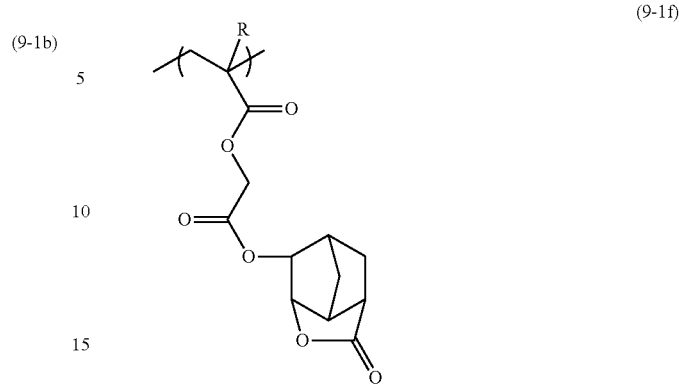 (9-1f)
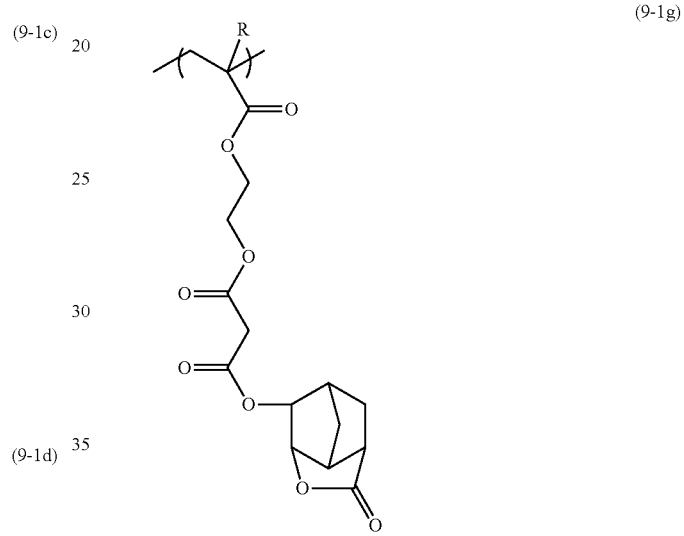 (9-1g)
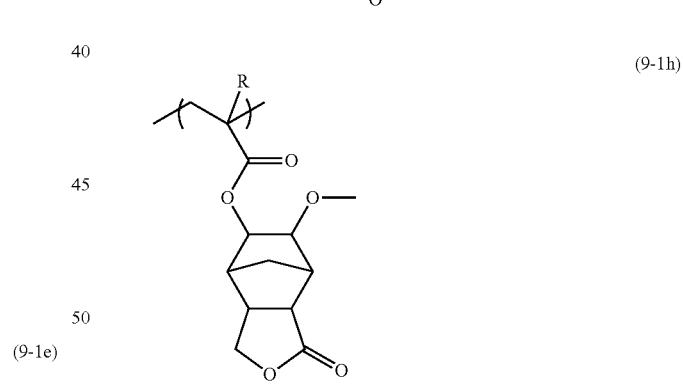 (9-1h)
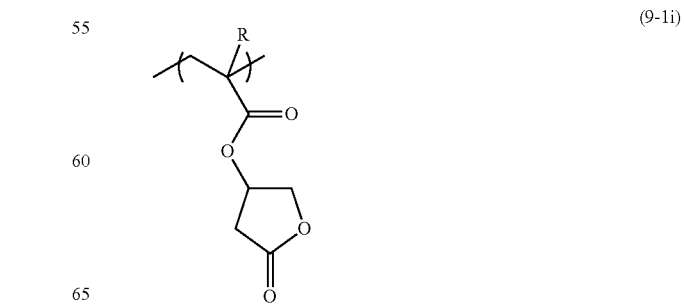 (9-1i)

(9-1j)

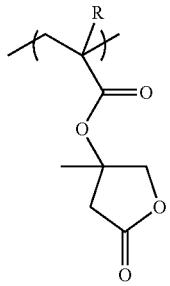

wherein R is the same as defined for the formula (9).

The polymer (A) may include only one type of repeating unit (a9), or may include two or more types of repeating unit (a9). Examples of a preferable monomer that produces the repeating unit (a9) include the monomers disclosed in paragraph [0043] of WO2007/116664.

Examples of the repeating unit (a9) having a cyclic carbonate structure include a structural unit shown by the following formula (9-2a).

[Chemical Formula 50]

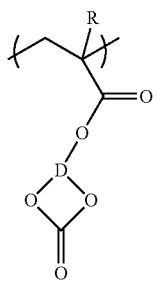

(9-2a)

wherein R is the same as defined for the formula (9), and D represents a trivalent chain-like hydrocarbon group having 1 to 30 carbon atoms, a trivalent alicyclic hydrocarbon group having 3 to 30 carbon atoms, or a trivalent aromatic hydrocarbon group having 6 to 30 carbon atoms. Note that the group represented by D may include an oxygen atom, a carbonyl group, or —NH— in the skeleton, and may be substituted with a substituent.

Examples of a substituent that may substitute the group represented by D include those mentioned above in connection with $R^{P4}$ in the formulas (Z-1) and (Z-2).

The monomer that produces the repeating unit shown by the formula (9-2a) may be synthesized by the method disclosed in Tetrahedron Letters, Vol. 27, No. 32, p. 3741 (1986), Organic Letters, Vol. 4, No. 15, p. 2561 (2002), or the like.

Examples of a preferable repeating unit shown by the formula (9-2a) include the repeating units disclosed in paragraph [0020] of Japanese Patent Application Publication (KOKAI) No. 2010-66503. Examples of a more preferable repeating unit shown by the formula (9-2a) include repeating units shown by the following formulas (9-2a-1) and (9-2a-2).

[Chemical Formula 51]

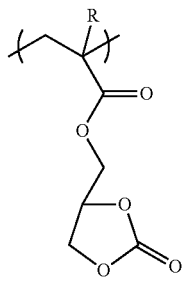

(9-2a-1)

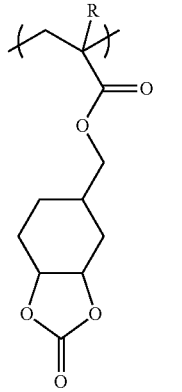

(9-2a-2)

wherein R is the same as defined for the formula (9).

The content of the repeating unit (a9) in the polymer (A) is normally 50 mol % or less, preferably 0 to 40 mol %, and more preferably 0 to 20 mol %, based on the total repeating units included in the polymer (A). The polymer (A) may include only one type of repeating unit (a9), or may include two or more types of repeating unit (a9).

The content of the polymer (A) in the radiation-sensitive resin composition is preferably 0.1 to 20 mass % based on the total amount of the radiation-sensitive resin composition. If the content of the polymer (A) is 0.1 mass % or more, the repeating unit (a1) is uniformly dispersed in the surface layer of a resist film formed using the composition. As a result, the surface of the resist film exhibits uniform hydrophobicity during liquid immersion lithography, and exhibits uniform surface wettability during alkali development. If the content of the polymer (A) is 20 mass % or less, a pattern can be advantageously formed. The content of the polymer (A) is more preferably 1 to 10 mass %, and still more preferably 3.0 to 8.0 mass %. The polymer (A) is preferably used in an amount of 20 parts by mass or less, and more preferably 0.1 to 10 parts by mass, based on 100 parts by mass of the polymer (C).

The polystyrene-reduced weight average molecular weight (hereinafter may be referred to as "Mw") of the polymer (A) determined by gel permeation chromatography (GPC) is not particularly limited, but is preferably 1000 to 50,000. If the Mw of the polymer (A) is 1000 or more, the polymer (A) exhibits excellent dry etching resistance. If the Mw of the polymer (A) is 50,000 or less, the polymer (A) can be easily dissolved in a solvent. The Mw of the polymer (A) is more preferably 2000 to 30,000, and still more preferably 5000 to 15,000.

The ratio (Mw/Mn) of the Mw to the polystyrene-reduced number average molecular weight (hereinafter may be referred to as "Mn") of the polymer (A) determined by GPC is preferably 1.0 to 5.0, more preferably 1.0 to 3.0, and still more preferably 1.0 to 2.0.

The fluorine atom content (mass %) in the polymer (A) is preferably 1 to 40 mass % based on the mass of the polymer (A). If the fluorine atom content is 1 mass % or more, the surface of the resist film exhibits excellent hydrophobicity during liquid immersion lithography. If the fluorine atom content is 40 mass % or less, a pattern can be advantageously formed. The fluorine atom content is more preferably 1.5 to 30 mass %, and still more preferably 2.0 to 28 mass %.

<Method of Producing Monomer that Produces Repeating Unit (a1)>

A monomer that includes a group shown by any of the formulas (1-1) to (1-3) may be produced by a known method, for example. For example, the monomer may be produced by reacting a compound (V1) shown by the following formula (V-1) with a compound (V2) shown by the following formula (V-2).

[Chemical Formula 52]

The compound (V1) shown by the formula (V-1) is obtained by substituting a hydrogen atom of the compound shown by any of the formulas (M-1) to (M-3) wherein $R^T$ represents a hydrogen atom with a leaving group (Xh).

The compounds (V1) and (V2) may be obtained via synthesis, or commercially available products may be used as the compounds (V1) and (V2).

A solvent used when reacting the compound (V1) with the compound (V2) is not particularly limited as long as the compounds (V1) and (V2) can be dissolved therein. Examples of the solvent include tetrahydrofuran (THF), acetone, dimethylformamide (DMF), dimethylacetamide, dimethyl sulfoxide (DMSO), acetonitrile, dichloromethane, and the like.

Examples of a base include organic bases such as triethylamine, 4-dimethylaminopyridine (DMAP), and pyridine; inorganic bases such as sodium hydride, $K_2CO_3$, and $Cs_2CO_3$; and the like.

Examples of a condensation agent include carbodiimide reagents such as ethyldiisopropylaminocarbodiimide hydrochloride (EDCI), dicyclohexylcarboxylmide (DCC), diisopropylcarbodiimide, and carbodiimidazole, tetraethyl pyrophosphate, benzotriazole-N-hydroxytrisdimethylaminophosphonium hexafluorophosphate (Bop reagent), and the like. These condensation agents may be used either individually or in combination.

The compounds (V1) and (V2) are preferably used so that the molar ratio of the compound (V2) to the compound (V1) is 1 to 3, and more preferably 1 to 2.

The reaction temperature may be determined depending on the reaction method and the like, but is preferably −20 to 40° C., and more preferably 0 to 30° C. The reaction time may be determined depending on the reactivity, the reaction temperature, and the like, but is preferably 30 minutes to 8 hours, and more preferably 60 minutes to 6 hours.

<Method of Producing Polymer (A)>

The polymer (A) may be synthesized by radical polymerization or the like. For example, the polymer (A) is preferably synthesized by (1) adding a solution containing a monomer and a radical initiator dropwise to a reaction solvent or a solution containing a monomer to effect polymerization, (2) adding a solution containing a monomer and a solution containing a radical initiator dropwise to a reaction solvent or a solution containing a monomer to effect polymerization, or (3) adding a plurality of solutions respectively containing a monomer and a solution containing a radical initiator dropwise to a reaction solvent or a solution containing a monomer to effect polymerization.

The reaction temperature may be appropriately determined depending on the type of initiator. The reaction temperature is normally 30 to 150° C., preferably 40 to 150° C., and more preferably 50 to 140° C. The dropwise addition time is determined depending on the reaction temperature, the type of initiator, the type of monomer, and the like, but is preferably 30 minutes to 8 hours, and more preferably 1 to 6 hours. The total reaction time including the dropwise addition time is determined depending on the above conditions, but is normally 30 minutes to 12 hours, preferably 45 minutes to 12 hours, and more preferably 1 to 10 hours.

Examples of the radical initiator used for polymerization include azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), dimethyl 2,2'-azobis(2-methylpropionate), and 4,4'-azobis(4-cyanovaleric acid) (V-501); peroxide radical initiators such as benzoyl peroxide, t-butyl hydroperoxide, and cumene hydroperoxide; and the like. These radical initiators may be used either individually or in combination. It is preferable to use AIBN or V-501.

A solvent that is not a solvent that hinders polymerization (e.g., nitrobenzene which has a polymerization inhibiting effect or a mercapto compound which has a chain transfer effect) and can dissolve the monomers may be used as the polymerization solvent. Examples of such a solvent include alcohols, ethers, ketones, amides, ester-lactones, nitriles, a mixture thereof, and the like. These solvents may be used either individually or in combination.

The polymer obtained by polymerization is preferably collected by re-precipitation. Specifically, the polymer solution is poured into a re-precipitation solvent after completion of polymerization to collect the target polymer as a powder. An alcohol, an alkane, and the like may be used as the re-precipitation solvent either individually or in combination. The polymer may also be collected by removing low-molecular-weight components (e.g., monomer and oligomer) by a separation operation, a column operation, ultrafiltration, or the like.

<Acid Generator (B)>

Examples of the acid generator (B) included in the radiation-sensitive resin composition include onium salt compounds (e.g., sulfonium salts and iodonium salts), organic halogen compounds, and sulfone compounds (e.g., disulfones and diazomethanesulfones). The acid generator (B) may be included in the radiation-sensitive resin composition as a compound (described below) and/or an acid-generating group included in the polymer (A), the polymer (C) (described later), or the like.

Specific examples of a preferable acid generator (B) include the compounds disclosed at paragraphs [0080] to [0113] of Japanese Patent Application Publication (KOKAI) No. 2009-134088, and the like.

Specific examples of a preferable acid generator (B) include diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl) iodonium nonafluoro-n-butanesulfonate, bis(4-t- butylphenyl)iodonium perfluoro-n-octanesulfonate, triphenylsulfonium trifluoromethanesulfonate, triphenylsulfonium nonafluoro-n-butanesulfonate, triphenylsulfonium perfluoro-n-octanesulfonate, cyclohexyl.2-oxocyclohexyl-.methylsulfonium trifluoromethanesulfonate, dicyclohexyl.2-oxocyclohexylsulfonium trifluoromethanesulfonate, 2-oxocyclohexyldimethylsulfonium trifluoromethanesulfonate, 4-hydroxy-1-naphthyldimethylsulfonium trifluoromethanesulfonate, 4-hydroxy-1-naphthyltetrahydrothiophenium trifluoromethanesulfonate, 4-hydroxy-1-naphthyltetrahydrothiophenium nonafluoro-n-butanesulfonate, 4-hydroxy-1-naphthyltetrahydrothiophenium perfluoro-n-octanesulfonate, 1-(1-naphthylacetomethyl)tetrahydrothiophenium trifluoromethanesulfonate, 1-(1-naphthylacetomethyl)tetrahydrothiophenium nonafluoro-n-butanesulfonate, 1-(1-naphthylacetomethyl)tetrahydrothiophenium perfluoro-n-octanesulfonate, 1-(3,5-dimethyl-4-hydroxyphenyl)tetrahydrothiophenium trifluoromethanesulfonate, 1-(3,5-dimethyl-4-hydroxy phenyl)tetrahydrothiophenium nonafluoro-n-butanesulfonate, 1-(3,5-dimethyl-4-hydroxyphenyl)tetrahydrothiophenium perfluoro-n-octanesulfonate, 4-cyclohexylphenyldiphenylsulfonium perfluoro-n-butanesulfonate, triphenylsulfonium 2-(adamantan-1-yl)-1,1-difluoroethane-1-sulfonate, triphenylsulfonium 6-(adamantan-1-ylcarbonyloxy)-1,1,2,2-tetrafluorohexane-1-sulfonate, triphenylsulfonium 2-bicyclo[2.2.1]hept-2-yl)-1,1,2,2-tetrafluoroethanesulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarb odiimide, perfluoro-n-octanesulfonylbicyclo[2.2.1]hept-5-ene-2,3-dicarbodiimide, N-hydroxysuccinimidetrifluoromethanesulfonate, N-hydroxysuccinimidenonafluoro-n-butanesulfonate, N-hydroxysuccinimideperfluoro-n-octanesulfonate, and 1,8-naphthalenedicarboxylic acid imide trifluoromethanesulfonate.

These compounds may be used either individually or in combination as the acid generator (B). The acid generator (B) is preferably used in an amount of 0.1 to 30 parts by mass, and more preferably 0.1 to 20 parts by mass, based on 100 parts by mass of the polymers included in the radiation-sensitive resin composition, so that the resulting resist exhibits excellent sensitivity and developability. If the amount of the acid generator is less than 0.1 parts by mass, a decrease in sensitivity and developability may occur. If the amount of the acid generator exceeds 30 parts by mass, a rectangular resist pattern may not be obtained due to a decrease in transparency to radiation.

<Polymer (C)>

The radiation-sensitive resin composition preferably includes the polymer (C) that includes an acid-labile group in addition to the polymer (A). The polymer that includes an acid-labile group is insoluble or scarcely soluble in an alkali, but becomes alkali-soluble upon dissociation (elimination) of the acid-labile group due to an acid generated by the acid generator (B) or the like. The expression "insoluble or scarcely soluble in an alkali" means that a film (thickness: 100 nm) that is formed only of the polymer has a thickness equal to or more than 50% of the initial thickness when developed under alkaline conditions employed when forming a resist pattern using a resist film that is formed using the radiation-sensitive resin composition.

When the polymer (A) included in the radiation-sensitive resin composition does not include an acid-labile group, a resist pattern can be formed from a resist film formed using the composition when the composition includes the polymer (C).

It is preferable that the polymer (A) have a fluorine atom content higher than that of the polymer (C). In this case, the polymer (A) tends to be unevenly distributed in the surface layer of a resist film formed using the radiation-sensitive resin composition that includes the polymers (A) and (C). The fluorine atom content may be determined by $^{13}$C-NMR analysis.

When the polymer (C) does not include a fluorine atom, the polymer (A) preferably has the above fluorine atom content. When the polymer (C) includes a fluorine atom, the ratio of the fluorine atom content of the polymer (A) to the fluorine atom content of the polymer (C) is preferably 1.1 to 5.0. If the ratio of the fluorine atom content of the polymer (A) to the fluorine atom content of the polymer (C) is 1.1 or more, the surface of the resulting resist film exhibits excellent hydrophobicity during liquid immersion lithography. If the ratio of the fluorine atom content of the polymer (A) to the fluorine atom content of the polymer (C) is 5.0 or less, a pattern can be advantageously formed due to excellent dry etching resistance. The ratio of the fluorine atom content of the polymer (A) to the fluorine atom content of the polymer (C) is more preferably 1.2 to 4.5, and still more preferably 1.5 to 4.

The structure of the polymer (C) is not particularly limited as long as the polymer (C) has the above properties. It is preferable that the polymer (C) include the repeating unit (a9) shown by the formula (9). It is also preferable that the polymer (C) further include the repeating unit (a4) shown by the formula (4) or the repeating unit (a8) shown by the formula (8).

The content of the repeating unit (a4) in the polymer (C) is preferably 0 to 30 mol %, and more preferably 0 to 15 mol %, based on the total repeating units included in the polymer (C).

The content of the repeating unit (a8) in the polymer (C) is preferably 0 to 30 mol %, and more preferably 0 to 15 mol %, based on the total repeating units included in the polymer (C).

The content of the repeating unit (a9) in the polymer (C) is preferably 5 to 75 mol %, more preferably 15 to 65 mol %, and still more preferably 25 to 55 mol %, based on the total repeating units included in the polymer (C). If the content of the structural unit (a9) is 5 mol % or more, the resulting pattern rarely peels off due to sufficient adhesion to a substrate. If the content of the structural unit (a9) is 75 mol % or less, an excellent pattern shape can be obtained since a decrease in contrast after dissolution rarely occurs.

The polymer (C) may further include an additional repeating unit other than the repeating units (a4), (a8), and (a9) as long as the polymer (C) has the above fluorine atom content. Examples of a polymerizable unsaturated monomer that produces such an additional repeating unit include the monomers disclosed in paragraphs [0065] to [0085] of WO2007/116664.

A repeating unit derived from 2-hydroxyethyl (meth)acrylate, 2-hydroxypropyl (meth)acrylate, or 3-hydroxypropyl (meth)acrylate is preferable as the additional repeating unit.

The Mw of the polymer (C) is normally 3000 to 300,000, preferably 4000 to 200,000, and still more preferably 4000 to 100,000. If the Mw of the polymer (C) is less than 3000, the heat resistance of the resulting resist may deteriorate. If the Mw of the polymer (C) exceeds 300,000, the developability of the resulting resist may deteriorate. The ratio "Mw/Mn" of the polymer (C) is preferably 1.0 to 5.0, more preferably 1.0 to 3.0, and still more preferably 1.0 to 2.0.

<Acid Diffusion Controller (D)>

The radiation-sensitive resin composition may optionally include the acid diffusion controller (D). Examples of the acid diffusion controller (D) include a compound shown by the following formula (11) (hereinafter referred to as "nitrogen-containing compound (I)"), a compound that includes two nitrogen atoms in the molecule (hereinafter referred to as "nitrogen-containing compound (II)"), a compound that includes three or more nitrogen atoms in the molecule (hereinafter referred to as "nitrogen-containing compound (III)"), an amide group-containing compound, a urea compound, a nitrogen-containing heterocyclic compound, and the like. The acid diffusion controller improves the pattern shape and the dimensional accuracy of the resulting resist. The acid diffusion controller (D) may be included in the radiation-sensitive resin composition as a compound (described below) and/or an acid diffusion-controlling group included in the polymer (A), the polymer (C), or the like.

[Chemical Formula 53]

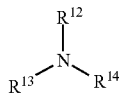

(11)

wherein $R^{12}$ to $R^{14}$ individually represent a hydrogen atom, a substituted or unsubstituted linear, branched, or cyclic alkyl group, an aryl group, or an aralkyl group.

Examples of the nitrogen-containing compound (I) include monoalkylamines such as n-hexylamine; dialkylamines such as di-n-butylamine; trialkylamines such as triethylamine; aromatic amines such as aniline; and the like.

Examples of the nitrogen-containing compound (II) include ethylenediamine, N,N,N',N'-tetramethylethylenediamine, and the like.

Examples of the nitrogen-containing compound (III) include polyethyleneimine, polyallylamine, poly(dimethylaminoethylacrylamide), and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include pyridines such as pyridine and 2-methylpyridine, pyrazine, pyrazole, and the like.

A compound that includes an acid-labile group may also be used as the nitrogen-containing organic compound. Examples of the nitrogen-containing organic compound that includes an acid-labile group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, N-(t-butoxycarbonyl)diphenylamine, N-(t-butoxycarbonyl)-4-hydroxypiperidine, and the like.

A compound shown by the following formula (12) may also be used as the acid diffusion controller.

$$X^+Z^-$$ (12)

wherein $X^+$ represents a cation shown by the following formula (12-1-1) or (12-1-2), and $Z^-$ represents Off, an anion shown by $R^{D1}$—COO$^-$, an anion shown by $R^{D1}$—SO$_3^-$, or an anion shown by $R^{D1}$—N$^-$—SO$_2$—$R^{D2}$ (wherein $R^{D1}$ represents a substituted or unsubstituted alkyl group, a substituted or unsubstituted monovalent alicyclic hydrocarbon group, or a substituted or unsubstituted aryl group, and $R^{D2}$ represents an alkyl group in which some or all of the hydrogen atoms are substituted with a fluorine atom, or a monovalent alicyclic hydrocarbon group).

[Chemical Formula 54]

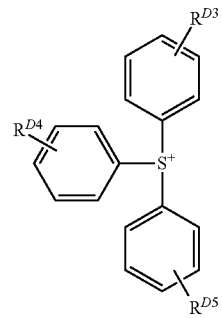

(12-1-1)

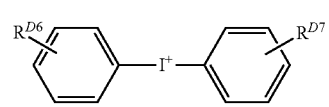

(12-1-2)

wherein $R^{D3}$ to $R^{D5}$ individually represent a hydrogen atom, an alkyl group, an alkoxy group, a hydroxyl group, or a halogen atom, and $R^{D6}$ and $R^{D7}$ individually represent a hydrogen atom, an alkyl group, an alkoxy group, a hydroxyl group, or a halogen atom.

The above compound is used as an acid diffusion controller that loses acid diffusion controllability upon decomposition due to exposure (hereinafter may be referred to as "photodegradable acid diffusion controller"). The above compound allows diffusion of an acid in the exposed area, but controls diffusion of an acid in the unexposed area, so that the contrast between the exposed area and the unexposed area is improved (i.e., the boundary between the exposed area and the unexposed area becomes distinct). This is effective for improving the line width roughness (LWR) and the mask error enhancement factor (MEEF) of the radiation-sensitive resin composition.

$X^+$ in the formula (12) represents the cation shown by the formula (12-1-1) or (12-1-2). $R^{D3}$ to $R^{D5}$ in the formula (12-1-1) individually represent a hydrogen atom, an alkyl group, an alkoxy group, a hydroxyl group, or a halogen atom. $R^{D3}$ to $R^{D5}$ preferably represent a hydrogen atom, an alkyl group, an alkoxy group, or a halogen atom since the solubility of the compound in a developer decreases. $R^{D6}$ and $R^{D7}$ in the formula (12-1-2) individually represent a hydrogen atom, an alkyl group, an alkoxy group, a hydroxyl group, or a halogen atom. $R^{D6}$ and $R^{D7}$ preferably represent a hydrogen atom, an alkyl group, or a halogen atom.

$Z^-$ in the formula (12) represents OH$^-$, an anion shown by $R^{D1}$—COO$^-$, an anion shown by $R^{D1}$—SO$_3^-$, or an anion shown by $R^{D1}$—N$^-$—SO$_2$—$R^{D2}$. $R^{D1}$ represents a substituted or unsubstituted alkyl group, a substituted or unsubstituted alicyclic hydrocarbon group, or a substituted or unsubstituted aryl group. $R^{D1}$ preferably represents an alicyclic hydrocarbon group or an aryl group since the solubility of the compound in a developer decreases.

Examples of the substituted or unsubstituted alkyl group represented by $R^{D1}$ include groups that include one or more substituents such as hydroxyalkyl groups having 1 to 4 carbon atoms such as a hydroxymethyl group; alkoxy groups having 1 to 4 carbon atoms such as a methoxy group; a cyano group; and cyanoalkyl groups having 2 to 5 carbon atoms such as a cyanomethyl group. Among these, a hydroxymethyl group, a cyano group, and a cyanomethyl group are preferable.

Examples of the substituted or unsubstituted alicyclic hydrocarbon group represented by $R^{D1}$ include monovalent groups derived from an alicyclic hydrocarbon such as a cycloalkane skeleton (e.g., hydroxycyclopentane, hydroxycyclohexane, or cyclohexanone), or a bridged alicyclic hydrocarbon skeleton (e.g., 1,7,7-trimethylbicyclo[2.2.1] heptan-2-one (camphor)). Among these, a group derived from 1,7,7-trimethylbicyclo[2.2.1]heptan-2-one is preferable.

Examples of the substituted or unsubstituted aryl group represented by $R^{D1}$ include a phenyl group, a benzyl group, a phenylethyl group, a phenylpropyl group, a phenylcyclohexyl group, and a group obtained by substituting these groups (compounds) with a hydroxyl group, a cyano group, or the like. Among these, a phenyl group, a benzyl group, and a phenylcyclohexyl group are preferable.

$Z^-$ in the formula (12) preferably represents the anion shown by the following formula (12-2-1) (i.e., an anion shown by $R^{D1}$—COO$^-$ wherein $R^{D1}$ represents a phenyl group), the anion shown by the following formula (12-2-2) (i.e., an anion shown by $R^{D1}$—SO$_3^-$ wherein $R^{D1}$ represents a group derived from 1,7,7-trimethylbicyclo[2.2.1]heptan-2-one), or the anion shown by the following formula (12-2-3) (i.e., an anion shown by $R^{D1}$—N$^-$—SO$_2$—$R^{D2}$ wherein $R^{D1}$ represents a butyl group, and $R^{D2}$ represents a trifluoromethyl group).

[Chemical Formula 55]

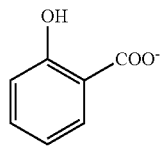

(12-2-1)

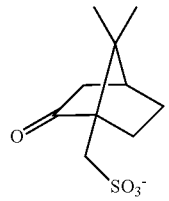

(12-2-2)

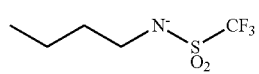

(12-2-3)

The photodegradable acid diffusion controller is shown by the formula (12). Specifically, the photodegradable acid diffusion controller is a sulfonium salt compound or an iodonium salt compound that satisfies the above conditions.

Examples of the sulfonium salt compound include triphenylsulfonium hydroxide, triphenylsulfonium salicylate, triphenylsulfonium 4-trifluoromethyl salicylate, diphenyl-4-hydroxyphenylsulfonium salicylate, triphenylsulfonium 10-camphorsulfonate, 4-t-butoxyphenyl.diphenylsulfonium 10-camphorsulfonate, and the like. These sulfonium salt compounds may be used either individually or in combination.

Examples of the iodonium salt compound include bis(4-t-butylphenyl)iodonium hydroxide, bis(4-t-butylphenyl)iodonium salicylate, bis(4-t-butylphenyl)iodonium 4-trifluoromethyl salicylate, bis(4-t-butylphenyl)iodonium 10-camphorsulfonate, and the like. These iodonium salt compounds may be used either individually or in combination.

These acid diffusion controllers (D) may be used either individually or in combination. The acid diffusion controller (D) is preferably used in an amount of 10 parts by mass or less, and more preferably 5 parts by mass or less, based on 100 parts by mass of the polymers included in the radiation-sensitive resin composition. If the amount of the acid diffusion controller (D) is too large, the sensitivity of the resulting resist film may unduly decrease.

<Solvent (E)>

The radiation-sensitive resin composition normally includes the solvent (E). The solvent is not particularly limited as long as at least the polymer (A), the acid generator (B), the optional polymer (C), and the like can be dissolved therein. Examples of the solvent (E) include linear or branched ketones, cyclic ketones, propylene glycol monoalkyl ether acetates, alkyl 2-hydroxypropionates, alkyl 3-alkoxypropionates, and the like.

Among these, linear or branched ketones, cyclic ketones, propylene glycol monoalkyl ether acetates, alkyl 2-hydroxypropionates, alkyl 3-alkoxypropionates, and the like are preferable, and propylene glycol monomethyl ether acetate and cyclohexanone are more preferable. These solvents may be used either individually or in combination.

<Additive (F)>

The radiation-sensitive resin composition may optionally include an uneven distribution promoter, a surfactant, an alicyclic compound, a sensitizer, a crosslinking agent, and the like as the additive (F).

(Uneven Distribution Promoter)

The uneven distribution promoter causes the polymer (A) to be more efficiently unevenly distributed in the surface layer of the resist film. The amount of the polymer (A) used to produce the radiation-sensitive resin composition can be reduced by adding the uneven distribution promoter to the radiation-sensitive resin composition. This makes it possible to further suppress elution of components from the resist film into an immersion liquid, or implement high-speed liquid immersion lithography via a high-speed scan without impairing the basic resist performance (e.g., LWR, development defect resistance, and pattern collapse resistance), so that the hydrophobicity of the surface of the resist film that suppresses defects (e.g., watermark defects) that may occur due to liquid immersion lithography can be improved. Examples of the uneven distribution promoter include a low-molecular-weight compound having a relative dielectric constant of 30 to 200 and a boiling point at 1 atmosphere of 100° C. or more. Examples of such a compound include lactone compounds, carbonate compounds, nitrile compounds, polyhydric alcohols, and the like.

Specific examples of the lactone compounds include γ-butyrolactone, valerolactone, mevalonic lactone, norbornane lactone, and the like.

Specific examples of the carbonate compounds include propylene carbonate, ethylene carbonate, butylene carbonate, vinylene carbonate, and the like.

Specific examples of the nitrile compounds include succinonitrile and the like. Specific examples of the polyhydric alcohols include glycerol and the like.

The uneven distribution promoter is used in an amount of 10 to 500 parts by mass, and preferably 30 to 300 parts by mass, based on 100 parts by mass of the polymers included in the radiation-sensitive resin composition. The radiation-sensitive resin composition may include only one type of uneven distribution promoter, or may include two or more types of uneven distribution promoter.

(Surfactant)

The surfactant improves the applicability, the developability, and the like of the radiation-sensitive resin composition. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate, commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination. The surfactant is normally used in an amount of 2 parts by mass or less based on 100 parts by mass of the polymers included in the radiation-sensitive resin composition.

(Alicyclic Skeleton-Containing Compound)

The alicyclic skeleton-containing compound further improves the dry etching resistance, the pattern shape, adhesion to a substrate, and the like. Examples of the alicyclic skeleton-containing compound include adamantane derivatives such as 1-adamantanecarboxylic acid, 2-adamantanone, and t-butyl 1-adamantanecarboxylate; deoxycholates such as t-butyl deoxycholate, t-butoxycarbonylmethyl deoxycholate, and 2-ethoxyethyl deoxycholate; lithocholates such as t-butyl lithocholate, t-butoxycarbonylmethyl lithocholate, and 2-ethoxyethyl lithocholate; 3-[2-hydroxy-2,2-bis(trifluoromethyl)ethyl]tetracyclo[4.4.0.1$^{2,5}$.1$^{7,10}$]dodecane; 2-hydroxy-9-methoxycarbonyl-5-oxo-4-oxa-tricyclo[4.2.1.0$^{3,7}$] nonane; and the like. These alicyclic skeleton-containing compounds may be used either individually or in combination. The alicyclic skeleton-containing compound is normally used in an amount of 50 parts by mass or less, and preferably 30 parts by mass or less, based on 100 parts by mass of the polymers included in the radiation-sensitive resin composition.

(Sensitizer)

The sensitizer absorbs energy other than the energy of radiation absorbed by the acid generator (B), and transmits the energy to the acid generator (B) as radicals or the like so that the amount of acid generated increases. The sensitizer thus improves the apparent sensitivity of the radiation-sensitive resin composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination.

(Crosslinking Agent)

When using the radiation-sensitive resin composition as a negative-tone radiation-sensitive resin composition, the radiation-sensitive resin composition may include a compound that crosslinks an alkaline developer-soluble polymer in the presence of an acid (hereinafter referred to as "crosslinking agent"). Examples of the crosslinking agent include a compound that includes at least one functional group (hereinafter referred to as "crosslinkable functional group") that exhibits crosslinking reactivity with an alkaline developer-soluble polymer.

Examples of the crosslinkable functional group include a glycidyl ether group, a glycidyl ester group, a glycidyl amino group, a methoxymethyl group, an ethoxymethyl group, a benzyloxymethyl group, an acetoxymethyl group, a benzoiloxymethyl group, a formyl group, an acetyl group, a vinyl group, an isopropenyl group, a (dimethylamino)methyl group, a (diethylamino)methyl group, a (dimethylamino) methyl group, a (diethylamino)methyl group, a morpholinomethyl group, and the like.

Examples of the crosslinking agent include the crosslinking agents disclosed in paragraphs [0169] to [0172] of WO2009/51088.

A methoxymethyl group-containing compound (e.g., dimethoxymethylurea or tetramethoxy methyl glycoluril) is particularly preferable as the crosslinking agent. The negative-tone radiation-sensitive resin composition may include only one type of crosslinking agent, or may include two or more types of crosslinking agent.

The crosslinking agent is preferably used in an amount of 5 to 95 parts by mass, more preferably 15 to 85 parts by mass, and particularly preferably 20 to 75 parts by mass, based on 100 parts by mass of the alkaline developer-soluble polymer. If the amount of the crosslinking agent is less than 5 parts by mass, the residual ratio may decrease, or the resulting pattern may be curved or may swell, for example. If the amount of the crosslinking agent exceeds 95 parts by mass, the alkali developopability of the composition may deteriorate.

A dye, a pigment, an adhesion improver, and the like may also be used as the additive (F). For example, the dye or pigment visualizes the latent image in the exposed area, and reduces the effect of halation during exposure. The adhesion improver improves adhesion to a substrate. Examples of other additives include an alkali-soluble resin, a low-molecular-weight alkali-solubility controller that includes an acid-labile protecting group, a halation inhibitor, a preservation stabilizer, an anti-foaming agent, and the like.

These additives (F) may be used either individually or in combination.

<Preparation of Radiation-Sensitive Resin Composition Solution>

The radiation-sensitive resin composition is normally prepared as a composition solution by dissolving the components in the solvent so that the total solid content is 1 to 50 mass %, and preferably 3 to 25 mass %, and filtering the solution through a filter having a pore size of about 0.02 µm, for example.

It is preferable that the radiation-sensitive resin composition have an impurity (e.g., halogen ions and metals) content as low as possible. The sensitivity, the resolution, the process stability, the pattern shape, and the like of the resist film can be further improved by reducing the impurity content. Therefore, the polymers (A) and (C) used to produce the radiation-sensitive resin composition are preferably purified by chemical purification (e.g., washing with water or liquid-liquid extraction) or a combination of chemical purification and physical purification (e.g., ultrafiltration or centrifugation).

The resin composition is preferably prepared so that at least the surface layer of a resist film formed by a step described below includes the repeating unit (a1), and the surface area of the resist film has a fluorine atom content higher than that of the substrate-side area (described below) of the resist film. This ensures that the surface of the resist film exhibits improved hydrophobicity during liquid immersion lithography, and the reactivity is improved when the hydrophobicity decreases in the presence of an acid or under alkaline conditions.

The term "surface area" used herein refers to a distribution range of the polymer (A) in the resist film (e.g., an area from the surface of the resist film having a depth corresponding to 1 to 5% of the thickness of the resist film). The term "substrate-side area" used herein refers to a distribution range of the polymer (B) in the resist film. Specifically, the term "substrate-side area" used herein refers to an area that is positioned closer to the substrate than the surface area (e.g., an area from the surface of the substrate (back surface of the resist film)) having a depth (height) corresponding to 1 to 20% of the thickness of the resist film.

<Photoresist Pattern-Forming Method>

A resist pattern-forming method according to the invention includes (1) forming a photoresist (resist) film on a substrate using the radiation-sensitive resin composition (hereinafter may be referred to as "step (1)"), (2) subjecting the resist film to liquid immersion lithography via an immersion liquid provided over the resist film (hereinafter may be referred to as "step (2)"), and (3) developing the resist film subjected to liquid immersion lithography to form a resist pattern (hereinafter may be referred to as "step (3)"). This method makes it possible to form a resist pattern having an excellent pattern shape.

In the step (1), a resist film is formed by applying a solution of the radiation-sensitive composition (radiation-sensitive resin composition solution) to a substrate (e.g., silicon wafer or aluminum-coated wafer) by an appropriate coating method (e.g., rotational coating, cast coating, or roll coating). Specifically, the radiation-sensitive resin composition solution is applied so that the resulting resist film has a given thickness, and prebaked (PB) to volatilize the solvent from the film. A resist film is thus formed.

The thickness of the resist film is not particularly limited, but is preferably 10 to 5000 nm, and more preferably 10 to 2000 nm.

The prebaking temperature is determined depending on the composition of the radiation-sensitive resin composition, but is preferably about 30 to 200° C., and more preferably 50 to 150° C.

In the step (2), radiation is applied to the resist film formed by the step (1) via an immersion liquid provided over the resist film (i.e., the resist film is subjected to liquid immersion lithography).

Purified water, a long-chain or cyclic aliphatic compound, or the like may be used as the immersion liquid.

Visible rays, ultraviolet rays, deep ultraviolet rays, X-rays, electron beams, or the like may be appropriately used as the radiation depending on the type of acid generator. It is preferable to use deep ultraviolet rays such as ArF excimer laser light (wavelength: 193 nm) or KrF excimer laser light (wavelength: 248 nm). It is particularly preferable to use ArF excimer laser light (wavelength: 193 nm).

The exposure conditions (e.g., dose) may be appropriately selected depending on the composition of the radiation-sensitive resin composition, the type of additive, and the like.

It is preferable to perform post-exposure bake (PEB) after exposure. The acid-labile group included in the resin component dissociates smoothly due to PEB. The PEB temperature may be appropriately adjusted depending on the composition of the radiation-sensitive resin composition, but is normally 30 to 200° C., and preferably 50 to 170° C.

In order to maximize the performance of the radiation-sensitive resin composition, an organic or inorganic antireflective film may be formed on the substrate, as disclosed in Japanese Examined Patent Publication (KOKOKU) No. 6-12452 (Japanese Patent Application Publication (KOKAI) No. 59-93448), for example. A protective film may be formed on the resist film so that the resist film is not affected by basic impurities and the like contained in the environmental atmosphere, as disclosed in Japanese Patent Application Publication (KOKAI) No. 5-188598, for example. In order to prevent outflow of the acid generator and the like from the resist film during liquid immersion lithography, a liquid immersion lithography protective film may be formed on the resist film, as disclosed in Japanese Patent Application Publication (KOKAI) No. 2005-352384, for example. Note that these techniques may be used in combination.

When utilizing liquid immersion lithography, a resist pattern can be formed by the resist film obtained using the radiation-sensitive resin composition according to one embodiment of the invention without providing a protective film (upper-layer film) on the resist film. In this case, the throughput is expected to be improved since it is unnecessary to form a protective film (upper-layer film).

In the step (3), the resist film subjected to liquid immersion lithography (i.e., exposed resist film) is developed to form a given resist pattern.

It is preferable to use an alkaline aqueous solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water as a developer used for development.

The concentration of the alkaline aqueous solution is preferably 10 mass % or less. If the concentration of the alkaline aqueous solution exceeds 10 mass %, the unexposed area may be dissolved in the developer.

An organic solvent may be added to the alkaline aqueous solution (developer).

Examples of the organic solvent include ketones such as acetone, methyl ethyl ketone, methyl i-butyl ketone, cyclopentanone, cyclohexanone, 3-methylcyclopentanone, and 2,6-dimethylcyclohexanone, alcohols such as methyl alcohol, ethyl alcohol, n-propyl alcohol, i-propyl alcohol, n-butyl alcohol, t-butyl alcohol, cyclopentanol, cyclohexanol, 1,4-hexanediol, and 1,4-hexanedimethylol, ethers such as tetrahydrofuran and dioxane, esters such as ethyl acetate, n-butyl acetate, and i-amyl acetate, aromatic hydrocarbons such as toluene and xylene, phenol, acetonylacetone, dimethylformamide, and the like.

These organic solvents may be used either individually or in combination.

The organic solvent is preferably used in an amount of 100 parts by volume or less based on 100 parts by volume of the alkaline aqueous solution. If the amount of the organic solvent exceeds 100 parts by volume, the exposed area may remain undeveloped due to a decrease in developability.

An appropriate amount of a surfactant or the like may also be added to the alkaline aqueous solution (developer).

After development using the alkaline aqueous solution (developer), the resist film is normally rinsed with water, and dried.

<Resist Film>

A resist film according to the invention is formed using the radiation-sensitive resin composition according to the invention. The radiation-sensitive resin composition includes the fluorine-containing polymer (A) that includes the repeating unit (a1). When the polymer (A) has a fluorine atom content higher than that of the polymer (C), the polymer (A) tends to be unevenly distributed in the surface layer of a resist film formed on a substrate. Therefore, the surface of the resist film has a high contact angle with a water droplet. For example, the surface of the resist film has a receding contact angle (i.e., contact angle (dynamic contact angle)) with a water droplet of 70° or more when the resist film is tilted. The term "receding contact angle" used herein refers to the contact angle of a water droplet with the resist film at the rear endpoint in the moving direction of the water droplet. The receding contact angle increases as the hydrophobicity of the surface of the resist film increases.

In the polymer (A), a unit that includes an electron-withdrawing group is bonded to the carbon atom at the α-position with respect to the carbon atom of the ester group. Therefore, the ester group included in the polymer (A) exhibits high reactivity, so that the monovalent organic group —$R^P$ dissociates promptly in the presence of an acid or under alkaline conditions to produce a carboxylic acid. When forming a resist film using the composition that includes the polymer (A), the surface of the resist film exhibits hydrophobicity due to the fluorine atom included in the polymer (A), and a carboxylic acid is promptly produced in the presence of an acid or under alkaline conditions. When the monovalent organic group —$R^P$ is an acid-labile group, the resist film exhibits excellent solubility in a developer after exposure, and the exposed area rarely remains undeveloped. As a result, defects such as bridge defects can be advantageously suppressed. When the monovalent organic group —$R^P$ is an alkali-labile group, impurities (e.g., development residue) rarely adhere to the surface of the film during alkali development. Moreover, since the alkaline developer is promptly spread over the surface of the resist film when the alkaline developer has come in contact with the surface of the resist film, the resist film can be advantageously developed. Therefore, the composition makes it possible to form a resist film that can suppress occurrence of development defects as much as possible.

<Evaluation of Rate of Reaction with Alkaline Developer>

The rate of reaction (rate of hydrolysis) of the polymer (A) with an alkaline developer may be evaluated using the contact angle with water (e.g., static contact angle (i.e., the contact angle of the resist film in a horizontal state with a water droplet) or dynamic contact angle (i.e., the contact angle of the resist film in a tilted state with a water droplet)) or the like as an index. The rate of hydrolysis may be evaluated by causing a resist film that includes the polymer (A) to come in contact with the alkaline developer, and measuring a change in contact angle with time after causing the resist film to come in contact with the alkaline developer.

It is preferable to use the dynamic contact angle (e.g., sliding angle, advancing contact angle, or receding contact angle), and it is more preferable to use the receding contact angle. The term "sliding angle" used herein refers to the contact angle when a water droplet has moved, and the term "advancing contact angle" refers to the contact angle of a water droplet with the resist film at the front endpoint in the moving direction of the water droplet. The term "receding contact angle" used herein refers to the contact angle of a water droplet with the resist film at the rear endpoint in the moving direction of the water droplet. The advancing contact angle and the receding contact angle increase and the sliding angle decreases as the hydrophobicity of the resist film increases. Specifically, a decrease in advancing contact angle and receding contact angle increases and an increase in sliding angle increases as the rate of reaction of the polymer (A) with the alkaline developer increases.

EXAMPLES

The invention is further described below by way of examples. Note that the invention is not limited to the following examples. The property values were measured by the following methods.

<Polystyrene-Reduced Weight Average Molecular Weight (Mw)>

The polystyrene-reduced weight average molecular weight (Mn) was determined by gel permeation chromatography (GPC) using GPC columns manufactured by Tosoh Corporation (G2000HXL×2, G3000HXL×1, G4000HXL×1) at a flow rate of 1.0 ml/min and a column temperature of 40° C. (eluant: tetrahydrofuran, standard: monodisperse polystyrene).

<Polystyrene-Reduced Number Average Molecular Weight (Mn)>

The polystyrene-reduced number average molecular weight (Mn) was determined by gel permeation chromatography (GPC) using GPC columns manufactured by Tosoh Corporation (G2000HXL×2, G3000HXL×1, G4000HXL×1) at a flow rate of 1.0 ml/min and a column temperature of 40° C. (eluant: tetrahydrofuran, standard: monodisperse polystyrene).

Synthesis of Monomer

Synthesis of Monomer (M-18)

Synthesis Example 1

Synthesis of ethyl 2-cyano-3-hydroxypropanoate

A reactor was charged with 0.26 g (1 mmol) of acetylacetonatodicarbonylrhodium, 0.52 g (2 mmol) of triphenylphosphine, and 200 ml of tetrahydrofuran (THF). The mixture was stirred for 10 minutes in a nitrogen atmosphere. After the dropwise addition of 10.54 g (130 mmol) of a 37% formaldehyde aqueous solution and 11.31 g (100 mmol) of ethyl 2-cyanoacetate, the mixture was reacted at 25° C. for 16 hours with stirring. After completion of the reaction, the reaction mixture was concentrated under reduced pressure, and the residue was purified by silica gel column chromatography (eluant: hexane/ethyl acetate (=10/1)) to obtain 9.16 g of ethyl 2-cyano-3-hydroxypropanoate shown by the following formula (M-18') (yield: 64%).

[Chemical Formula 56]

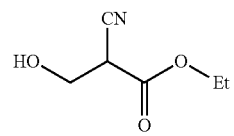

(M-18')

Synthesis Example 2

Synthesis of 2-cyano-3-ethoxy-3-oxopropyl methacrylate

A reactor was charged with 14.31 g (100 mmol) of the compound shown by the formula (M-18') and 200 ml of tetrahydrofuran. 12.1 g (120 mmol) of triethylamine and 12.5 g (120 mmol) of methacryloyl chloride were added dropwise to the mixture in a nitrogen atmosphere while cooling the mixture to 0° C. The mixture was then reacted at 20° C. for 2 hours with stirring. The resulting suspension was filtered under reduced pressure. The filtrate was concentrated under reduced pressure, and the residue was purified by silica gel column chromatography (eluant: hexane/ethyl acetate (=20/1)) to obtain 17.31 g of 2-cyano-3-ethoxy-3-oxopropyl methacrylate shown by the following formula (M-18) (yield: 82%).

[Chemical Formula 57]

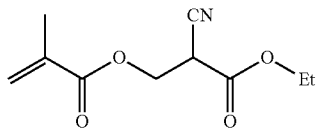

(M-18)

Synthesis of Monomer (M-19)

Synthesis Example 3

Synthesis of ethyl 2-nitro-3-hydroxypropanoate 5.87 g of ethyl 2-nitro-3-hydroxypropanoate shown by the following formula (M-19') was obtained in the same manner as in Synthesis Example 1, except that 13.30 g (100 mmol) of ethyl 2-nitroacetate was used instead of 11.31 g of ethyl 2-cyanoacetate (total yield: 36%).

[Chemical Formula 58]

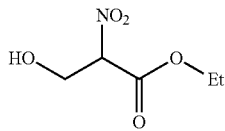

(M-19')

Synthesis Example 4

Synthesis of 2-nitro-3-ethoxy-3-oxopropyl methacrylate 17.57 g of 2-nitro-3-ethoxy-3-oxopropyl methacrylate shown by the following formula (M-19) was obtained in the same manner as in Synthesis Example 2, except that 16.31 g (100 mmol) of the compound shown by the formula (M-19') was used instead of 14.31 g of the compound shown by the formula (M-18') (total yield: 76%).

[Chemical Formula 59]

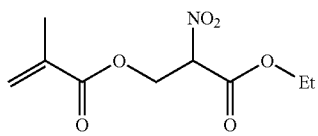

(M-19)

Synthesis of Monomer (M-20)

Synthesis Example 5

Synthesis of 2-bromoethyl Methacrylate

A reactor was charged with 12.50 g (100 mmol) of 2-bromoethanol and 100 ml of tetrahydrofuran (THF) at 0° C. in a nitrogen atmosphere. After the dropwise addition of 10.45 g (100 mmol) of methacrylic chloride and 11.13 g (110 mmol) of triethylamine, the mixture was reacted at 25° C. for 30 minutes with stirring. After completion of the reaction, the reaction mixture was concentrated under reduced pressure, and the residue was purified by distillation to obtain 17.30 g of 2-bromoethyl methacrylate shown by the following formula (M-20') (yield: 90%).

[Chemical Formula 60]

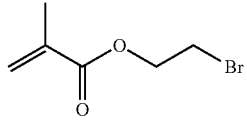

(M-20')

Synthesis Example 6

Synthesis of ethyl 2-cyano-4-(methacryloyloxy)butanoate

A reactor was charged with 13.82 g (100 mmol) of potassium hydrogencarbonate, 19.30 g (100 mmol) of the compound shown by the formula (M-20'), 11.31 g (100 mmol) of ethyl cyanoacetate, and 500 ml of DMF in a nitrogen atmosphere. The mixture was reacted at 100° C. for 8 hours with stirring. The resulting suspension was filtered under reduced pressure. The filtrate was concentrated under reduced pressure, and the residue was purified by silica gel column chromatography (eluant: hexane/ethyl acetate (=20/1)) to obtain 11.35 g of ethyl 2-cyano-4-(methacryloyloxy)butanoate shown by the following formula (M-20) (yield: 50%).

[Chemical Formula 61]

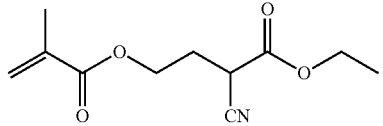

(M-20)

Synthesis of Monomer (M-21)

Synthesis Example 7

Synthesis of 2-cyano-3-(methacryloyloxy)propionic acid 5.13 g of 2-cyano-3-(methacryloyloxy)propionic acid shown by the following formula (M-21') was obtained in the same manner as in Synthesis Examples 1 and 2, except that 8.50 g (100 mmol) of 2-cyanoacetic acid was used instead of 11.31 g of ethyl 2-cyanoacetate (total yield: 28%).

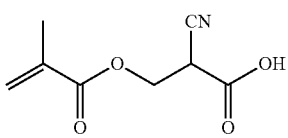

(M-21')

Synthesis Example 8

Synthesis of 2-cyano-3-oxo-3-(2,2,2-trifluoroethoxy)propyl methacrylate

A reactor was charged with 18.32 g (100 mmol) of the compound shown by the formula (M-20') and 200 ml of toluene. A solution prepared by dissolving 13.96 g (110 mmol) of oxalyl chloride in 200 ml of toluene was added dropwise to the mixture in a nitrogen atmosphere while cooling the mixture to 0° C. After the addition of 1 ml of DMF, the mixture was reacted at 25° C. for 1 hour with stirring. After cooling the mixture to 0° C., 20.00 g (200 mmol) of 2,2,2-trifluoroethanol and 20.24 g (200 mmol) of triethylamine were added to the mixture. The mixture was then reacted at 0° C. for 2 hours with stirring. The resulting suspension was filtered under reduced pressure. The filtrate was concentrated under reduced pressure, and the residue was purified by silica gel column chromatography (eluant: hexane/ethyl acetate (=20/1)) to obtain 17.31 g of 2-cyano-3-oxo-3-(2,2,2-trifluoroethoxy)propyl methacrylate shown by the following formula (M-21) (yield: 82%).

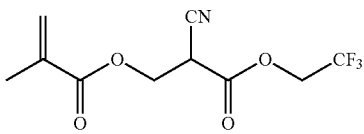

(M-21)

Synthesis of Monomer (M-22)

Synthesis Example 9

Synthesis of 2-cyano-3-oxo-3[3-(trifluoromethyl)phenoxy]propyl methacrylate 25.42 g of 2-cyano-3-oxo-3-[3-(trifluoromethyl)phenoxy]propyl methacrylate shown by the following formula (M-22) was obtained in the same manner as in Synthesis Example 8, except that 16.21 g (100 mmol) of 3-(trifluoromethyl)phenol was used instead of 20.00 g of 2,2,2-trifluoroethanol (yield: 78%).

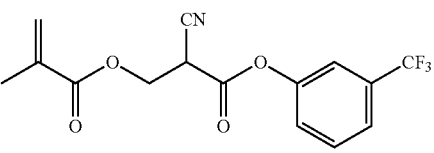

(M-22)

Synthesis of Monomer (M-23)

Synthesis Example 10

Synthesis of 2-cyano-3-oxo-3-phenoxypropyl methacrylate 24.23 g of 2-cyano-3-oxo-3-phenoxypropyl methacrylate shown by the following formula (M-23) was obtained in the same manner as in Synthesis Example 8, except that 9.41 g (100 mmol) of phenol was used instead of 20.00 g of 2,2,2-trifluoroethanol (yield: 71%).

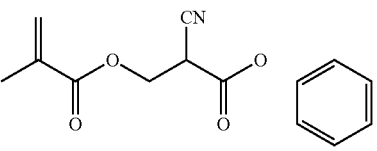

(M-23)

Synthesis of Monomer (M-24)

Synthesis Example 11

Synthesis of 2-cyano-3-oxo-3[4-(trifluoromethyl)benzoyloxy]propyl methacrylate 23.88 g of 2-cyano-3-oxo-3[4-(trifluoromethyl)benzoyloxy]propyl methacrylate shown by the following formula (M-24) was obtained in the same manner as in Synthesis Example 8, except that 17.61 g (100 mmol) of [4-(trifluoromethyl)phenyl]methanol was used instead of 20.00 g of 2,2,2-trifluoroethanol (yield: 70%).

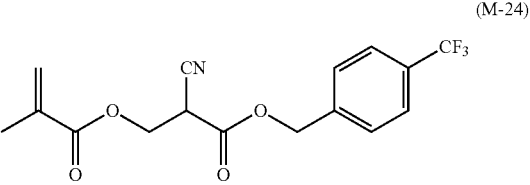

(M-24)

Synthesis of Monomer (M-25)

Comparative Synthesis Example 1

Synthesis 2-(methacryloyloxo)acetic Acid 26 g of 2-(methacryloyloxo)acetic acid shown by the following formula (M-25') was obtained by the synthesis method disclosed in paragraph 0269 of Japanese Patent Application Publication (KOKAI) No. 2010-32994.

[Chemical Formula 67]

(M-25')

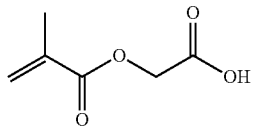

Comparative Synthesis Example 2

Synthesis of 2-oxo-2-(2,2,2-trifluoroethoxy)ethyl methacrylate 25 g of 2-oxo-2-(2,2,2-trifluoroethoxy)ethyl methacrylate shown by the following formula (M-25) was obtained by the synthesis method disclosed in paragraph 0320 of Japanese Patent Application Publication (KOKAI) No. 2010-32994 using 2-(methacryloyloxo)acetic acid shown by the formula (M-25').

[Chemical Formula 68]

(M-25)

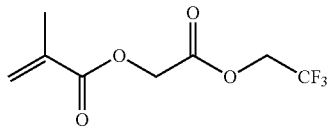

Synthesis of Polymer (A)

Polymers (A-1) to (A-20) (polymer (A)) were synthesized by the following method using a compound selected from the monomers (M-18) to (M-25) and the following monomers (M-1) to (M-17).

[Chemical Formula 69]

(M-1)

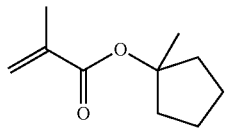

(M-2)

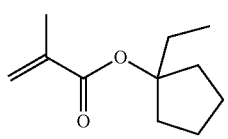

(M-3)

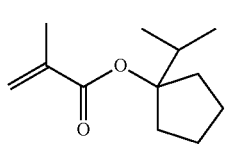

(M-4)

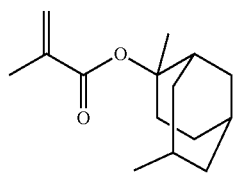

(M-5)

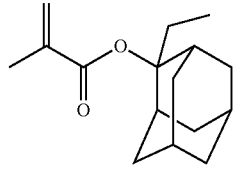

(M-6)

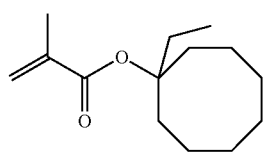

(M-7)

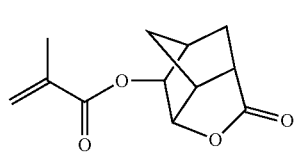

(M-8)

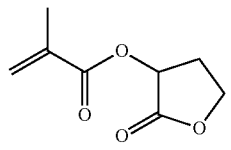

(M-9)

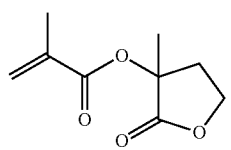

(M-10)

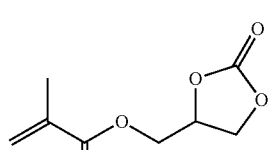

(M-11)

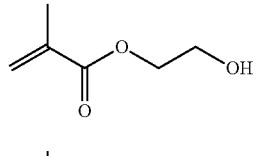

(M-12)

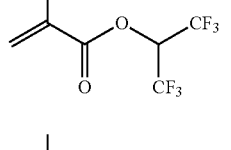

(M-13)

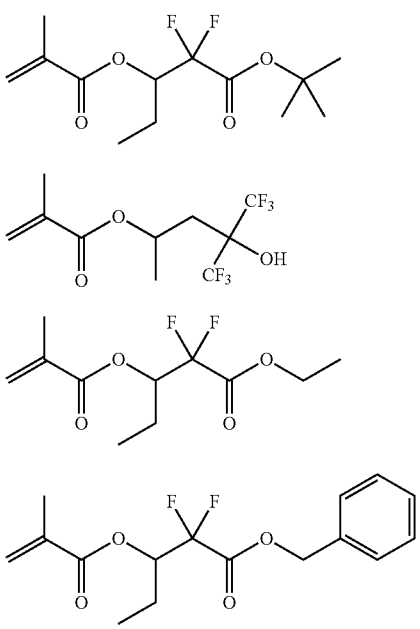

Example 1

A three-necked flask equipped with a thermometer and a reflux condenser was charged with 10 g (37.7 mmol) of the compound (M-21) synthesized in Synthesis Example 8 and 20 g of methyl ethyl ketone. The mixture was stirred to dissolve the compound. 0.32 g (1.96 mmol) of azobisisobutyronitrile (initiator) (manufactured by Wako Pure Chemical Industries, Ltd.) was added to (dissolved in) the solution. The resulting solution was heated at 80° C. for 5 hours with stirring to effect polymerization. The reaction mixture was then cooled to room temperature. The reaction mixture was concentrated under reduced pressure, and slowly added to 150 g of n-hexane. A solid that precipitated by this operation was washed three times with hexane, and dried under reduced pressure to obtain a solid. The resulting polymer is hereinafter referred to as "polymer (A-1)".

The polymer (A-1) had an Mw of 6900 and a dispersity (Mw/Mn) of 1.44. The polymer (A-1) had a fluorine atom content of 21.49 mass %.

Examples 2 to 20

The polymers (A-2) to (A-7) were produced in the same manner as in Example 1, except that the type and the amount of the monomer were changed as shown in Table 1 so that the total number of moles of the monomer was identical (37.7 mmol). The composition, the Mw, the dispersity (Mw/Mn), and the fluorine atom content of the polymers (A-1) to (A-20) are shown in Table 2.

Comparative Synthesis Examples 3 to 8

Polymers (a-1) to (a-6) were produced in the same manner as in Example 1, except that the compounds shown in Table 1 were used instead of the monomers (M-18) to (M-24). The composition, the Mw, the dispersity (Mw/Mn), and the fluorine atom content of the polymers (a-1) to (a-6) are also shown in Table 2.

TABLE 1

| | | Repeating unit (a1) | | Fluorine-containing repeating unit | | Repeating unit (a7) | | Additional repeating unit | |
|---|---|---|---|---|---|---|---|---|---|
| | Polymer | Compound | Content (mol %) | Compound | Content (mol %) | Compound | Content (mol %) | Compound | Content (mol %) |
| Example 1 | A-1 | M-21 | 100 | | | | | | |
| Example 2 | A-2 | M-21 | 80 | | | M-3 | 20 | | |
| Example 3 | A-3 | M-18 | 80 | M-13 | 10 | M-3 | 20 | | |
| Example 4 | A-4 | M-22 | 80 | | | M-3 | 20 | | |
| Example 5 | A-5 | M-23 | 70 | M-13 | 10 | M-3 | 20 | | |
| Example 6 | A-6 | M-24 | 70 | M-13 | 10 | M-3 | 20 | | |
| Example 7 | A-7 | M-20 | 80 | | | M-3 | 20 | | |
| Example 8 | A-8 | M-19 | 80 | | | M-3 | 20 | | |
| Example 9 | A-9 | M-21 | 80 | | | M-5 | 20 | | |
| Example 10 | A-10 | M-21 | 80 | | | M-6 | 20 | | |
| Example 11 | A-11 | M-21 | 90 | | | | | M-11 | 10 |
| Example 12 | A-12 | M-21 | 90 | M-12 | 10 | | | | |
| Example 13 | A-13 | M-21 | 90 | M-13 | 10 | | | | |
| Example 14 | A-14 | M-21 | 80 | M-14 | 20 | | | | |
| Example 15 | A-15 | M-21 | 80 | M-15 | 20 | | | | |
| Example 16 | A-16 | M-21 | 80 | M-16 | 20 | | | | |
| Example 17 | A-17 | M-21 | 80 | M-17 | 20 | | | | |
| Example 18 | A-18 | M-21 | 20 | M-16 | 50 | M-3 | 30 | | |
| Example 19 | A-19 | M-21 | 70 | | | M-5 | 20 | M-11 | 10 |
| Example 20 | A-20 | M-21 | 70 | | | M-6 | 20 | M-7 | 10 |
| Comparative Synthesis Example 3 | a-1 | | | M-13 | 30 | M-2 | 70 | | |
| Comparative Synthesis Example 4 | a-2 | | | M-12 | 40 | | | M-8 | 30 |
| | | | | M-15 | 30 | | | | |
| Comparative Synthesis Example 5 | a-3 | | | M-12 | 40 | | | M-9 | 30 |
| | | | | M-15 | 30 | | | | |
| Comparative Synthesis Example 6 | a-4 | | | M-12 | 40 | M-2 | 30 | M-8 | 30 |
| Comparative Synthesis Example 7 | a-5 | | | | | | | M-25 | 100 |
| Comparative Synthesis Example 8 | a-6 | | | | | M-2 | 30 | M-25 | 70 |

TABLE 2

| | Polymer | Repeating unit (a1) Type | Repeating unit (a1) Amount (mol %) | Fluorine-containing repeating unit Type | Fluorine-containing repeating unit Amount (mol %) | Repeating unit (a7) Type | Repeating unit (a7) Amount (mol %) | Additional repeating unit Type | Additional repeating unit Amount (mol %) | Mw | Mw/Mn | Fluorine atom content (mass %) |
|---|---|---|---|---|---|---|---|---|---|---|---|---|
| Example 1 | A-1 | M-21 | 100.0 | | | | | | | 6900 | 1.44 | 21.49 |
| Example 2 | A-2 | M-21 | 81.4 | | | M-3 | 18.6 | | | 7600 | 1.42 | 18.38 |
| Example 3 | A-3 | M-18 | 80.5 | M-13 | 10 | M-3 | 19.5 | | | 8100 | 1.48 | 2.53 |
| Example 4 | A-4 | M-22 | 81.9 | | | M-3 | 18.1 | | | 7200 | 1.46 | 15.38 |
| Example 5 | A-5 | M-23 | 70.9 | M-13 | 10 | M-3 | 19.1 | | | 7400 | 1.53 | 2.39 |
| Example 6 | A-6 | M-24 | 70 | M-13 | 10 | M-3 | 20 | | | 8000 | 1.43 | 2.30 |
| Example 7 | A-7 | M-20 | 80 | | | M-3 | 20 | | | 7800 | 1.48 | 17.05 |
| Example 8 | A-8 | M-19 | 80 | | | M-3 | 20 | | | 8400 | 1.50 | 18.80 |
| Example 9 | A-9 | M-21 | 81.5 | | | M-5 | 18.5 | | | 8200 | 1.46 | 17.73 |
| Example 10 | A-10 | M-21 | 79.6 | | | M-6 | 20.4 | | | 8700 | 1.48 | 17.66 |
| Example 11 | A-11 | M-21 | 88.5 | | | | | M-11 | 11.5 | 7900 | 1.42 | 20.21 |
| Example 12 | A-12 | M-21 | 90.9 | M-12 | 9.1 | | | | | 8200 | 1.45 | 23.69 |
| Example 13 | A-13 | M-21 | 90.3 | M-13 | 9.7 | | | | | 8600 | 1.51 | 22.29 |
| Example 14 | A-14 | M-21 | 80.4 | M-14 | 19.6 | | | | | 8300 | 1.43 | 19.90 |
| Example 15 | A-15 | M-21 | 78.2 | M-15 | 21.8 | | | | | 7900 | 1.47 | 25.57 |
| Example 16 | A-16 | M-21 | 79.6 | M-16 | 20.4 | | | | | 8300 | 1.52 | 20.27 |
| Example 17 | A-17 | M-21 | 78.7 | M-17 | 21.3 | | | | | 7400 | 1.56 | 19.24 |
| Example 18 | A-18 | M-21 | 21.2 | M-16 | 51.3 | M-3 | 27.5 | | | 8300 | 1.49 | 13.74 |
| Example 19 | A-19 | M-21 | 69.5 | | | M-5 | 18.1 | M-11 | 12.4 | 8100 | 1.45 | 16.14 |
| Example 20 | A-20 | M-21 | 71.2 | | | M-6 | 21.2 | M-7 | 7.6 | 7700 | 1.53 | 12.66 |
| Comparative Synthesis Example 3 | a-1 | | | M-13 | 30.1 | M-2 | 69.9 | | | 7,000 | 1.41 | 9.64 |
| Comparative Synthesis Example 4 | a-2 | | | M-12 | 41.1 | | | M-8 | 29.3 | 6,600 | 1.81 | 25.34 |
| | | | | M-15 | 29.6 | | | | | | | |
| Comparative Synthesis Example 5 | a-3 | | | M-12 | 40.9 | | | M-9 | 29.9 | 6,900 | 1.77 | 24.89 |
| | | | | M-15 | 28.9 | | | | | | | |
| Comparative Synthesis Example 6 | a-4 | | | M-12 | 41.3 | M-2 | 29.1 | M-8 | 29.6 | 6,900 | 1.88 | 23.43 |
| Comparative Synthesis Example 7 | a-5 | | | | | | | M-25 | 100.0 | 7,200 | 1.52 | 25.20 |
| Comparative Synthesis Example 8 | a-6 | | | | | M-2 | 28.8 | M-25 | 71.2 | 7,100 | 1.53 | 19.01 |

Synthesis of Polymer (C)

Synthesis Examples 12 to 16

Polymers (C-1) to (C-5) (polymer (C)) were produced in the same manner as in Example 1, except that the monomers shown in Table 3 were used. The composition, the Mw, the dispersity (Mw/Mn), and the fluorine atom content of the polymers (C-1) to (C-5) are shown in Table 3.

TABLE 3

| | Polymer | Compound Compound | Compound Amount (mol %) | Structural unit in polymer Content (mol %) | Property value Mw | Property value Mw/Mn | Fluorine atom content (mass %) |
|---|---|---|---|---|---|---|---|
| Synthesis Example 12 | C-1 | M-1 | 40 | 39.8 | 5500 | 1.41 | 0.00 |
| | | M-5 | 10 | 8.6 | | | |
| | | M-7 | 40 | 40.5 | | | |
| | | M-11 | 10 | 11.1 | | | |
| Synthesis Example 13 | C-2 | M-2 | 20 | 21.1 | 5500 | 1.43 | 0.00 |
| | | M-4 | 30 | 28.5 | | | |
| | | M-5 | 10 | 8.8 | | | |
| | | M-7 | 40 | 41.6 | | | |
| Synthesis Example 14 | C-3 | M-3 | 30 | 30.8 | 5500 | 1.41 | 0.00 |
| | | M-4 | 30 | 29.1 | | | |
| | | M-7 | 40 | 40.1 | | | |
| Synthesis Example 15 | C-4 | M-1 | 30 | 30.5 | 6000 | 1.39 | 0.00 |
| | | M-4 | 10 | 9.5 | | | |
| | | M-5 | 10 | 8.8 | | | |
| | | M-7 | 30 | 31.1 | | | |
| | | M-10 | 20 | 20.1 | | | |

TABLE 3-continued

| | Compound | | | Structural unit in polymer | Property value | | |
|---|---|---|---|---|---|---|---|
| | Polymer | Compound | Amount (mol %) | Content (mol %) | Mw | Mw/Mn | Fluorine atom content (mass %) |
| Synthesis Example 16 | C-5 | M-3 | 35 | 34.5 | 6000 | 1.42 | 5.11 |
| | | M-7 | 45 | 44.9 | | | |
| | | M-11 | 10 | 11.2 | | | |
| | | M-15 | 10 | 9.4 | | | |

<Preparation of Radiation-Sensitive Resin Composition>

The components (acid generator (B), acid diffusion controller (D), and solvent (E)) of the radiation-sensitive resin composition other than the polymers (A-1) to (A-17), (a-1) to (a-6), and (C-1) to (C-5) synthesized in the examples and the synthesis examples are shown below.

Acid Generator (B)

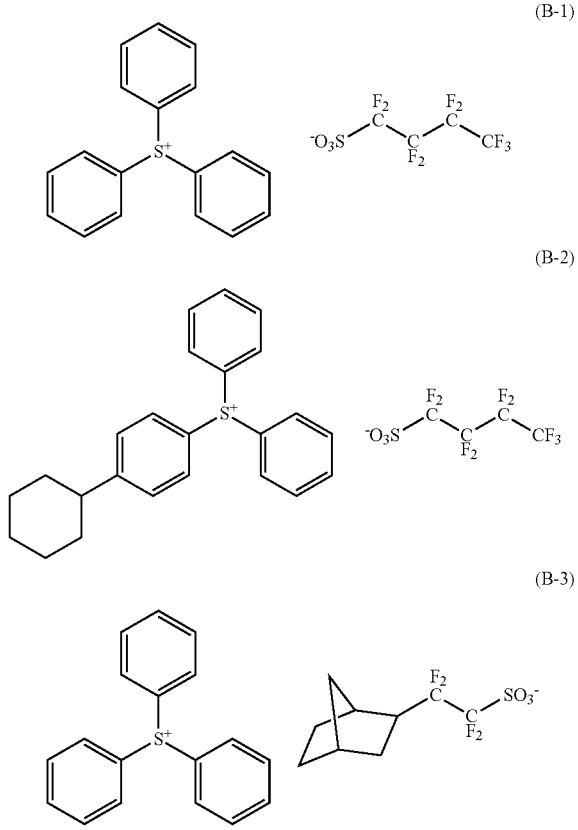

[Chemical Formula 70]

(B-1)
(B-2)
(B-3)

Acid Diffusion Controller (D)

[Chemical Formula 71]

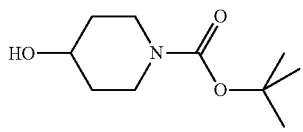

(D-1)

Solvent (E)
(E-1): propylene glycol monomethyl ether acetate
(E-2): cyclohexanone
Additive (F)
(F-1): γ-butyrolactone Example 21

5 parts by mass of the polymer (A-1) obtained in Example 1, 9.9 parts by mass of the acid generator (B-1), 100 parts by mass of the polymer (C-2) obtained in Synthesis Example 13, 1.5 parts by mass of the acid diffusion controller (D-1), 100 parts by mass of the additive (F-1) (γ-butyrolactone), 1500 parts by mass of the solvent (E-1), and 650 parts by mass of the solvent (E-2) were mixed to obtain a solution of a radiation-sensitive resin composition.

Examples 22 to 46 and Comparative Examples 1 to 6

A solution of a radiation-sensitive resin composition was prepared in the same manner as in Example 21, except that the composition was changed as shown in Table 4.

<Production and Evaluation of Resist Film>

A resist film was formed as described below using the radiation-sensitive resin composition obtained in each example or comparative example (Examples 21 to 46 and Comparative Examples 1 to 6), and the rate of reaction with an alkaline developer and development defects were evaluated using the resulting resist film. The rate of reaction was evaluated based on a change in receding contact angle with time upon contact with the alkaline developer. Development defects were evaluated by measuring the number of blob defects. The details are described below.

<Production of Resist Film>

A film was formed on a substrate using the radiation-sensitive resin composition. An 8-inch silicon wafer was used as the substrate when measuring the receding contact angle, and a 12-inch silicon wafer on which an underlayer antireflective film ("ARC66" manufactured by Nissan Chemical Industries, Ltd.) was formed was used as the substrate when measuring the number of blob defects. The thickness of the film was 110 nm.

<Measurement of Receding Contact Angle>

The receding contact angle of the film was measured by the following method at a temperature of 23° C. (room temperature) and a humidity of 45% under atmospheric pressure using a contact angle meter "DSA-10" (manufactured by KRUS).

The needle of the contact angle meter was washed with acetone and isopropyl alcohol before measurement. Water was injected into the needle, and the wafer was placed on the wafer stage. The height of the stage was adjusted so that the distance between the surface of the wafer and the tip of the needle was 1 mm or less. Water was discharged from the needle to form a water droplet (25 μl) on the wafer. The water droplet was sucked via the needle for 180 seconds at a rate of 10 μl/min, and the contact angle was measured every second (180 times in total). The measurement was performed after soft-baking (SB) the film at 120° C. for 50 seconds, and was also performed when 10 seconds or 30 seconds had elapsed after causing the alkaline developer to come in contact with the film. The average value of twenty contact angles after the contact angle became stable was calculated, and taken as the receding contact angle (°) under the respective measurement conditions.

After soft-baking (SB) the film under the above conditions, the film was developed for 10 seconds or 30 seconds using a 2.38 mass % tetramethylammonium hydroxide aqueous solution utilizing the GP nozzle of a developer "Clean Track ACT 8" (manufactured by Tokyo Electron Ltd.), and rinsed with purified water for 15 seconds. The substrate was then spin-dried at 2000 rpm, and the receding contact angle of the dried substrate was measured ("Receding contact angle after development for 10 seconds" and "Receding contact angle after development for 30 seconds").

<Blob defects>

The film was soft-baked (SB) at 120° C. for 50 seconds, and exposed via a line-and-space (1L/1S) mask pattern (target width: 45 nm) using an ArF immersion scanner ("NSR-5610C" manufactured by Nikon Corporation) (NA=1.3, ratio=0.800, Dipole). The exposed film was subjected to PEB at 95° C. for 50 seconds.

The film was then developed for 10 seconds using a 2.38 mass % tetramethylammonium hydroxide aqueous solution utilizing the GP nozzle of a developer "Clean Track ACT 8" (manufactured by Tokyo Electron Ltd.), and rinsed with purified water for 15 seconds. The substrate was then spin-dried at 2000 rpm to form a positive-tone resist pattern. A dose at which a 1L/1S pattern having a width of 45 nm was formed was determined to be an optimum dose. A 1L/1S pattern having a width of 45 nm was formed over the entire wafer at the optimum dose to obtain a defect inspection wafer. The measurement was performed using a scanning electron microscope ("CC-4000" manufactured by Hitachi High-Technologies Corporation). The number of defects on the defect inspection wafer was measured using a system "KLA2810" (manufactured by KLA-Tencor). Defects measured using the system "KLA2810" were classified into a defect due to the resist and a defect due to foreign matter.

The evaluation results are shown in Table 4.

TABLE 4

| | Polymer (A) | | Acid generator (B) | | Polymer (C) | | Receding contact angle (°) | | | | |
|---|---|---|---|---|---|---|---|---|---|---|---|
| | Type | Parts by mass | Type | Parts by mass | Type | Parts by mass | After SB | After development for 10 seconds | After development for 30 seconds | Difference between receding contact angle after SB and receding contact angle after development for 30 seconds | Number of development defects |
| Example 21 | A-1 | 5 | B-1 | 9.9 | C-2 | 100 | 82 | 25 | 25 | 57 | 0 |
| Example 22 | A-2 | 5 | B-1 | 9.9 | C-1 | 100 | 80 | 44 | 44 | 36 | 0 |
| Example 23 | A-2 | 5 | B-1 | 9.9 | C-2 | 100 | 76 | 51 | 51 | 25 | 0 |
| Example 24 | A-3 | 3 | B-1 | 9.9 | C-2 | 100 | 76 | 50 | 50 | 26 | 0 |
| Example 25 | A-4 | 3 | B-1 | 9.9 | C-2 | 100 | 81 | 48 | 48 | 33 | 0 |
| Example 26 | A-5 | 3 | B-1 | 9.9 | C-2 | 100 | 74 | 51 | 51 | 23 | 0 |
| Example 27 | A-6 | 3 | B-1 | 9.9 | C-2 | 100 | 73 | 50 | 50 | 23 | 0 |
| Example 28 | A-7 | 3 | B-1 | 9.9 | C-2 | 100 | 81 | 49 | 49 | 32 | 0 |
| Example 29 | A-8 | 3 | B-1 | 9.9 | C-2 | 100 | 81 | 33 | 33 | 48 | 0 |
| Example 30 | A-9 | 3 | B-1 | 9.9 | C-2 | 100 | 84 | 52 | 52 | 32 | 0 |
| Example 31 | A-10 | 3 | B-1 | 9.9 | C-2 | 100 | 83 | 46 | 46 | 37 | 0 |
| Example 32 | A-11 | 1 | B-1 | 9.9 | C-2 | 100 | 75 | 45 | 45 | 30 | 0 |
| Example 33 | A-2 | 1 | B-1 | 9.9 | C-2 | 100 | 79 | 51 | 51 | 28 | 0 |
| Example 34 | A-2 | 2 | B-1 | 9.9 | C-2 | 100 | 81 | 48 | 48 | 33 | 0 |
| Example 35 | A-2 | 2 | B-2 | 11.4 | C-2 | 100 | 81 | 46 | 46 | 35 | 0 |
| Example 36 | A-2 | 2 | B-3 | 9.5 | C-2 | 100 | 78 | 50 | 50 | 28 | 0 |
| Example 37 | A-2 | 2 | B-2 | 11.4 | C-3 | 100 | 80 | 44 | 44 | 36 | 0 |
| Example 38 | A-2 | 3 | B-2 | 11.4 | C-4 | 100 | 82 | 45 | 45 | 37 | 0 |
| Example 39 | A-2 | 3 | B-2 | 11.4 | C-5 | 100 | 80 | 40 | 40 | 40 | 0 |
| Example 40 | A-11 | 3 | B-1 | 9.9 | C-2 | 100 | 81 | 40 | 40 | 41 | 0 |
| Example 41 | A-12 | 3 | B-2 | 11.4 | C-4 | 100 | 88 | 51 | 51 | 37 | 0 |
| Example 42 | A-13 | 3 | B-2 | 11.4 | C-4 | 100 | 81 | 42 | 42 | 39 | 0 |
| Example 43 | A-14 | 3 | B-2 | 11.4 | C-4 | 100 | 81 | 45 | 45 | 36 | 0 |
| Example 44 | A-15 | 3 | B-2 | 11.4 | C-4 | 100 | 84 | 48 | 48 | 36 | 0 |
| Example 45 | A-16 | 3 | B-2 | 11.4 | C-4 | 100 | 80 | 51 | 51 | 29 | 0 |
| Example 46 | A-17 | 3 | B-2 | 11.4 | C-4 | 100 | 83 | 53 | 53 | 30 | 0 |
| Comparative Example 1 | a-1 | 3 | B-1 | 9.9 | C-2 | 100 | 78 | 78 | 76 | 2 | 62 |
| Comparative Example 2 | a-2 | 5 | B-1 | 9.9 | C-2 | 100 | 72 | 72 | 70 | 2 | 132 |
| Comparative Example 3 | a-3 | 5 | B-1 | 9.9 | C-2 | 100 | 68 | 66 | 65 | 3 | 215 |
| Comparative Example 4 | a-4 | 5 | B-1 | 9.9 | C-2 | 100 | 79 | 78 | 78 | 1 | 95 |
| Comparative Example 5 | a-5 | 5 | B-1 | 9.9 | C-2 | 100 | 89 | 70 | 60 | 29 | 2543 |
| Comparative Example 6 | a-6 | 5 | B-1 | 9.9 | C-2 | 100 | 86 | 80 | 65 | 21 | 356 |

As shown in Table 4, a high receding contact angle with water was obtained after SB when using the resist films of Examples 21 to 46 and Comparative Examples 1 to 6. It was thus confirmed that the resist films of Examples 21 to 46 will exhibit sufficiently high hydrophobicity during liquid immersion lithography.

When using the resist films of Comparative Examples 1 to 4, the receding contact angle changed to only a small extent when the resist film was developed for 10 seconds, and decreased by only about 1 to 3° when the resist film was developed for 30 seconds. When using the resist films of Comparative Examples 5 and 6, the receding contact angle changed slightly from 89° to 70° or from 86° to 80° when the resist film was developed for 10 seconds, and was 60° or more even when the resist film was developed for 30 seconds.

When using the resist films of Examples 21 to 46, the receding contact angle significantly decreased from 73 to 88° to less than 54° when the resist film was developed for 10 seconds. It was thus confirmed that the surface of the resist film formed using the composition including the polymer (A) promptly changed from a hydrophobic surface to a hydrophilic surface (surface wettability) upon contact with the alkaline developer. Specifically, it was confirmed that the surface of the resist film formed using the composition including the polymer (A) had a high rate of reaction with the alkaline developer. It is conjectured that the hydrophobic group included in the polymer (A) dissociated promptly under the alkaline conditions, so that COOH groups (hydrophilic group) were unevenly distributed in the surface layer of the film.

The number of blob defects was 60 or more when using the resist films of Comparative Examples 1 to 6, while the number of blob defects was 0 when using the resist films of Examples 21 to 46. This suggests that a high rate of reaction with the alkaline developer was achieved when using the resist films of Examples 21 to 46 as compared with the resist films of Comparative Examples 1 to 6, so that adhesion of impurities (e.g., development residue) to the surface of the film could be suppressed.

Obviously numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising (A) a polymer that includes a repeating unit (a1) and a fluorine atom, and (B) a photoacid generator, the repeating unit (a1) including a group shown by any of formulas (1-1) to (1-3),

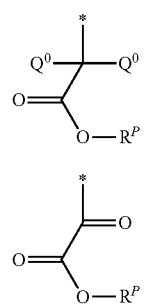

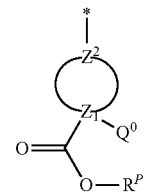

wherein $R^P$ represents a monovalent organic group, $Z^1$ represents a carbon atom, $Z^2$ represents a trivalent group that forms a cyclic hydrocarbon group together with $Z^1$, $Q^0$ in the formula (1-1) individually represent a hydrogen atom or a monovalent group, provided that at least one of $Q^0$ represents a monovalent organic group that includes an electron-withdrawing group, $Q^0$ in the formula (1-3) represents a monovalent organic group that includes an electron-withdrawing group, provided that a case where all of $Q^0$ in the formula (1-1) represent a fluorine atom or a fluorine-substituted hydrocarbon group is excluded, and "*" indicates a bonding hand, wherein the repeating unit (a1) includes at least one electron-withdrawing group as $Q^0$, the at least one electron-withdrawing group being other than a fluorine atom or a fluorine-substituted hydrocarbon group, and being bonded directly to a carbon atom at an α-position with respect to an ester group.

2. The radiation-sensitive resin composition according to claim 1, wherein the polymer (A) includes at least one repeating unit among repeating units shown by formulas (1p) to (3p) as the repeating unit (a1),

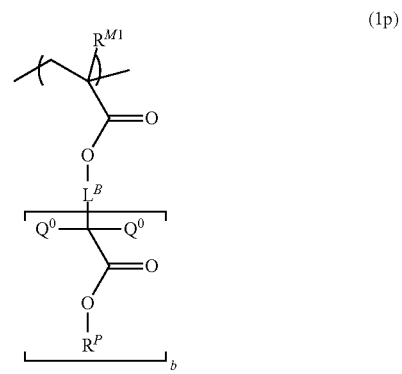

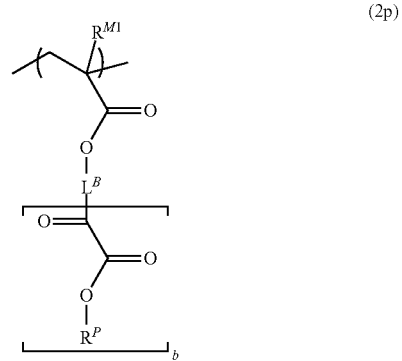

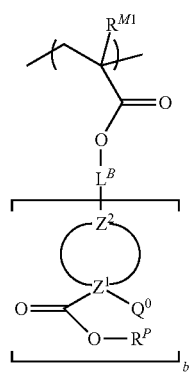

(3p)

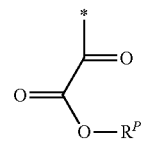

(1-2)

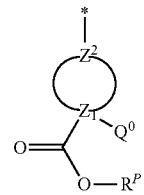

(1-3)

wherein $R^{M1}$ represents a hydrogen atom, a fluorine atom, an alkyl group having 1 to 5 carbon atoms, or a fluoroalkyl group having 1 to 5 carbon atoms, $L^B$ represents a single bond or a (b+1)-valent linking group, $R^P$ represents a monovalent organic group, $Z^1$ represents a carbon atom, $Z^2$ represents a trivalent group that forms a cyclic hydrocarbon group together with $Z^1$, $Q^0$ in the formula (1p) individually represent a hydrogen atom or a monovalent group, provided that at least one of $Q^0$ represents a monovalent organic group that includes an electron-withdrawing group, $Q^0$ in the formula (3p) represents a monovalent organic group that includes an electron-withdrawing group, provided that a case where all of $Q^0$ in the formula (1p) represent a fluorine atom or a fluorine-substituted hydrocarbon group is excluded, and b is 1 when $L^B$ represents a single bond, and is an integer from 1 to 5 when $L^B$ does not represent a single bond, provided that a plurality of $R^P$, a plurality of $Z^2$, and a plurality of $Q^0$ may respectively be either the same or different when b is an integer from 2 to 5.

3. The radiation-sensitive resin composition according to claim 1, wherein $R^P$ represents a monovalent hydrocarbon group that includes a fluorine atom.

4. The radiation-sensitive resin composition according to claim 1, wherein $R^P$ represents a monovalent aromatic hydrocarbon group that may include a fluorine atom.

5. The radiation-sensitive resin composition according to claim 1, further comprising (C) a polymer that has a fluorine atom content lower than that of the polymer (A), the polymer (C) including an acid-labile group.

6. The radiation-sensitive resin composition according to claim 1, wherein the group shown by the formula ($Q^0$-1) is —$NO_2$ or —CN.

7. A radiation-sensitive resin composition comprising (A) a polymer that includes a repeating unit (a1) and a fluorine atom, and (B) a photoacid generator, the repeating unit (a1) including a group shown by any of formulas (1-1) to (1-3), wherein the polymer (A) includes at least one repeating unit among repeating units shown by formulas (1p-1) to (1p-3) and (2p) as the repeating unit (a1), (1-1)

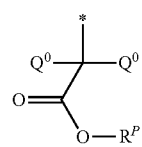

wherein $R^P$ represents a monovalent organic group, $Z^1$ represents a carbon atom, $Z^2$ represents a trivalent group that forms a cyclic hydrocarbon group together with $Z^1$, $Q^0$ in the formula (1-1) individually represent a hydrogen atom or a monovalent group, provided that at least one of $Q^0$ represents a monovalent organic group that includes an electron-withdrawing group, $Q^0$ in the formula (1-3) represents a monovalent organic group that includes an electron-withdrawing group, provided that a case where all of $Q^0$ in the formula (1-1) represent a fluorine atom or a fluorine-substituted hydrocarbon group is excluded, and "*" indicates a bonding hand, (1p-1)

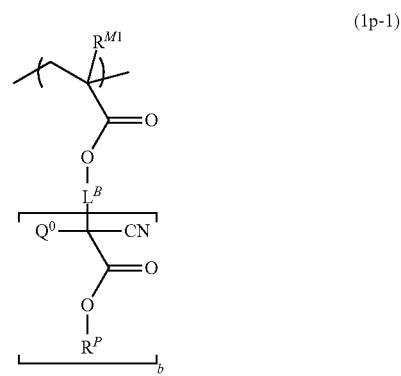

(1p-2)

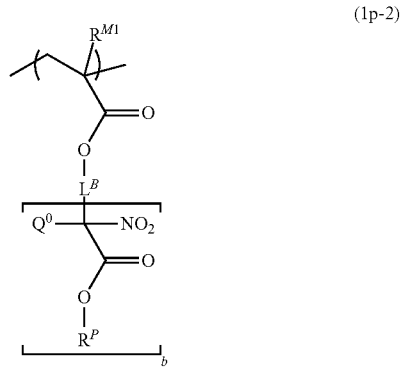

-continued (1p-3)

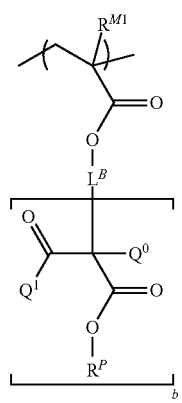

(2p)

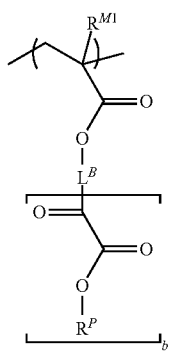

wherein $R^{M1}$ represents a hydrogen atom, a fluorine atom, an alkyl group having 1 to 5 carbon atoms, or a fluoroalkyl group having 1 to 5 carbon atoms, $L^B$ represents a single bond or a (b+1)-valent linking group, $R^P$ represents a monovalent organic group, $Q^0$ represents a hydrogen atom or a monovalent group, $Q^1$ represents a hydrogen atom or a monovalent hydrocarbon group, and b is 1 when $L^B$ represents a single bond, and is an integer from 1 to 5 when $L^B$ does not represent a single bond, provided that a plurality of $R^P$, a plurality of $Q^0$, and a plurality of $Q^1$ may respectively be either the same or different when b is an integer from 2 to 5.

8. The radiation-sensitive resin composition according to claim 7, wherein $R^P$ represents a monovalent hydrocarbon group that includes a fluorine atom.

9. The radiation-sensitive resin composition according to claim 7, wherein $R^P$ represents a monovalent aromatic hydrocarbon group that may include a fluorine atom.

10. The radiation-sensitive resin composition according to claim 7, further comprising (C) a polymer that has a fluorine atom content lower than that of the polymer (A), the polymer (C) including an acid-labile group.

11. The radiation-sensitive resin composition according to claim 7, wherein $Q^0$ represents a hydrogen atom.

* * * * *